(12) United States Patent
Tomašič et al.

(10) Patent No.: US 12,258,342 B2
(45) Date of Patent: Mar. 25, 2025

(54) CLASS OF DNA GYRASE AND/OR TOPOISOMERASE IV INHIBITORS WITH ACTIVITY AGAINST GRAM-POSITIVE AND GRAM-NEGATIVE BACTERIA

(71) Applicants: Univerza v Ljubljani, Ljubljana (SI); Szegedi Biológiai Kutatóközpont, Szeged (HU)

(72) Inventors: Tihomir Tomašič, Trzin (SI); Nace Zidar, Ljubljana (SI); Martina Durcik, Dutovlje (SI); Janez Ilaš, Škofljica (SI); Anamarija Zega, Ljubljana (SI); Cristina Durante Cruz, Helsinki (FI); Päivi Tammela, Helsinki (FI); Csaba Pál, Szeged (HU); Ákos József Nyerges, Szekesfehervar (HU); Danijel Kikelj, Ljubljana (SI); Lucija Peterlin Mašič, Medvode (SI)

(73) Assignees: Univerza v Ljubljani, Ljubljana (SI); Szegedi Biológiai Kutatóközpont, Szeged (HU)

( * ) Notice: Subject to any disclaimer, the term of this patent is extended or adjusted under 35 U.S.C. 154(b) by 884 days.

(21) Appl. No.: 17/272,871

(22) PCT Filed: Sep. 3, 2019

(86) PCT No.: PCT/EP2019/073412
§ 371 (c)(1),
(2) Date: Mar. 2, 2021

(87) PCT Pub. No.: WO2020/048949
PCT Pub. Date: Mar. 12, 2020

(65) Prior Publication Data
US 2021/0323957 A1    Oct. 21, 2021

(30) Foreign Application Priority Data
Sep. 3, 2018   (LU) .......................... 100918

(51) Int. Cl.
C07D 417/12    (2006.01)
A61P 31/04     (2006.01)
C07D 417/14    (2006.01)

(52) U.S. Cl.
CPC ............ *C07D 417/12* (2013.01); *A61P 31/04* (2018.01); *C07D 417/14* (2013.01)

(58) Field of Classification Search
CPC .............................. C07D 417/14; A61P 31/04
See application file for complete search history.

(56) References Cited

U.S. PATENT DOCUMENTS

| 6,608,087 B1 | 8/2003 | Charifson et al. |
| 2014/0073622 A1 | 3/2014 | Tsuyoshi et al. |
| 2017/0216252 A1 | 8/2017 | Young et al. |

FOREIGN PATENT DOCUMENTS

| WO | 9935155 | 7/1999 | |
| WO | 2001052845 | 7/2001 | |
| WO | 02060879 | 8/2002 | |
| WO | 2005026149 | 3/2005 | |
| WO | WO-2005037845 A1 * | 4/2005 | ........... A61K 31/428 |
| WO | 2006087543 | 8/2006 | |
| WO | 2006087544 | 8/2006 | |
| WO | 2006087548 | 8/2006 | |
| WO | 2006092608 | 8/2006 | |
| WO | 2006092599 | 9/2006 | |
| WO | 2007071965 | 6/2007 | |
| WO | 2008020222 | 2/2008 | |
| WO | 2008020227 | 2/2008 | |
| WO | 2008020229 | 2/2008 | |
| WO | 2008152418 | 12/2008 | |
| WO | 2009084614 | 7/2009 | |
| WO | 2009147431 | 12/2009 | |
| WO | 2010067123 | 6/2010 | |
| WO | 2010067125 | 6/2010 | |
| WO | 2017056012 | 4/2017 | |

OTHER PUBLICATIONS

Aurora Fine Chemicals, RN 901731-71-3, 2006, CHEMCATS (Year: 2006).*
ChemSpider, RN 1062114-99-1, 2008, CHEMCATS (Year: 2008).*
FCH Group, RN 1302350-88-4, 2011, CHEMCATS (Year: 2011).*
Interchim, RN 1371249-58-9, 2012, CHEMCATS (Year: 2012).*
Kugelberg Enorstrom Tpetersen Tkduvold Tandersson Dihughes D, "Establishment of a superficial skin infection model in mice by using *Staphylococcus aureus* and *Streptococcus pyogenes*", Antimicrob. Agents Chemother, (20050000), vol. 49, pp. 3435-3441.
Alt S., J. Antimicrob. Chemoth., (20110000), vol. 66, pp. 2061-2096.
Strachan, C.R. et al., Cold Spring Harb Perspect Med, (20170000), p. 7.
Brown, E.D. et al., Nature, (20160000), vol. 529, p. 336.
Klahn, P. et al., Curr Top Microbiol Immunol, (20160000), vol. 398, p. 365.

(Continued)

*Primary Examiner* — Brenda L Coleman
*Assistant Examiner* — Madeline E Braun
(74) *Attorney, Agent, or Firm* — Renner, Otto, Boisselle & Sklar, LLP

(57) ABSTRACT

The present invention relates to compounds having a structure of general formula (I), processes for their preparation, pharmaceutical compositions containing them as the active ingredient, to their use as medicaments and to their use in the manufacture of medicaments for use in the treatment of bacterial infections in humans and warm-blooded animals.

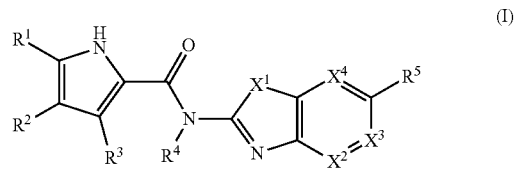

(I)

22 Claims, 1 Drawing Sheet

(56) References Cited

OTHER PUBLICATIONS

Tommasi, R. et al., Nat Rev Drug Discov, (20150000), vol. 14, p. 529.
Mayer, C. et al., Chem Rev, (20140000), vol. 114, p. 2313.
Tomasic, T. et al., Curr Top Med Chem, (20140000), vol. 14, p. 130.
Collin, F. et al., Appl Microbiol Biotechnol, (20110000), vol. 92, p. 479.
Gjorgjieva, M. et al., J Med Chem, (20160000), vol. 59, p. 8941.
Trzoss, M. et al., Bioorg Med Chem Lett, (20130000), vol. 23, p. 1537.
Zhang, J. et al., ACS Med Chem Lett, (20150000), vol. 6, p. 1080.
Durcik, M. et al., ChemMedChem, (20180000), vol. 113, p. 186.
Tari, L.W. et al., PLoS One, (20130000), vol. 8, p. e84409.
Zhang, J. et al., J Med Chem, (20150000), vol. 58, p. 8503.
Bisacchi, G.S. et al., ACS Infect Dis, (20150000), vol. 1, p. 4.
Gjorgjieva, M. et al., J. Med. Chem., (20160000), vol. 59, pp. 8941-8954.
Berge, S. M. et al., "Pharmaceutical Salts", Journal of Pharmaceutical Science,(19770000), vol. 66, doi: doi:10.1002/jps.2600660104, pp. 1-19, XP002675560 DOI: http://dx.doi.org/10.1002/jps.2600660104.
Marina Gjorgjieva et al, "Discovery of Benzothiazole Scaffold-Based DNA Gyrase B Inhibitors", Journal of Medicinal Chemistry, (Sep. 20, 2016), vol. 59, No. 19, doi: 10.1021/acs.jmedchem.6b00864, ISSN 0022-2623, pp. 8941-8954, XP055528262 [A] 1-24 * abstract * * p. 8942; figures 1-3 * * p. 8944; table 1 * * p. 8945; table 2 * DOI: http://dx.doi.org/10.1021/acs.jmedchem.6b00864.
Labrière Christophe et al, "Further investigation of inhibitors of MRSA pyruvate kinase: Towards the conception of novel antimicrobial agents", European Journal of Medicinal Chemistry, Editions Scientifique Elsevier, Paris, FR, (Sep. 9, 2016), vol. 125, doi: 10.1016/J.EJMECH.2016.09.018, ISSN 0223-5234, pp. 1-13, XP029842383 [A] 1-24 * abstract * * p. 3; table 1 *p. 4; table 2 * DOI: http://dx.doi.org/10.1016/j.ejmech.2016.09.018.
International Search Report and Written Opinion issued by the European Patent Office for corresponding in International Patent Application No. PCT/EP2019/073412.

* cited by examiner

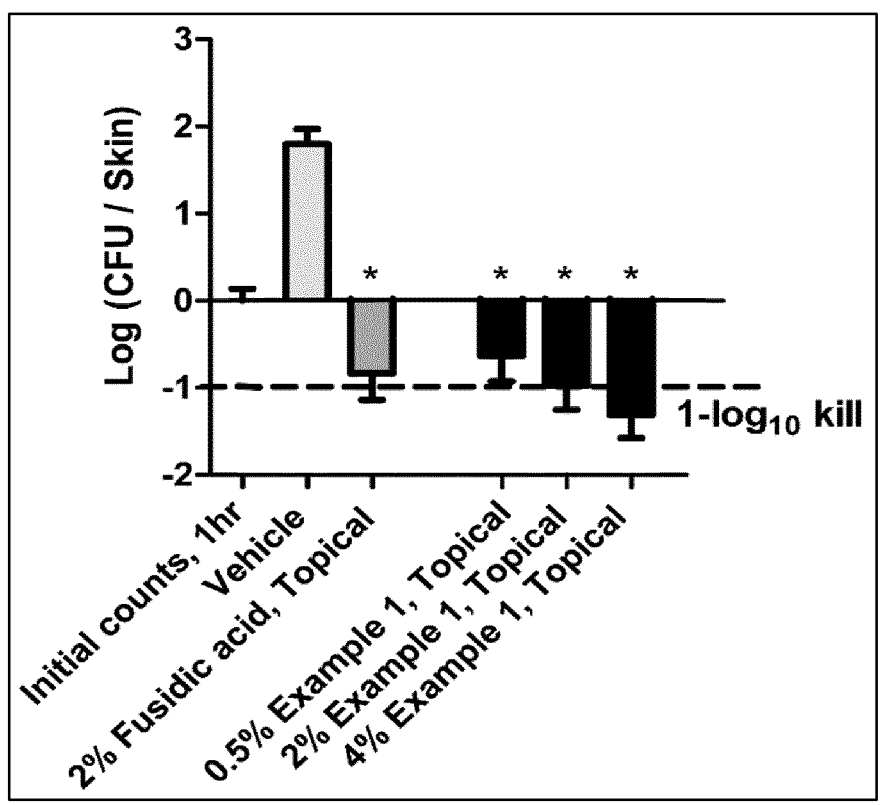

CLASS OF DNA GYRASE AND/OR TOPOISOMERASE IV INHIBITORS WITH ACTIVITY AGAINST GRAM-POSITIVE AND GRAM-NEGATIVE BACTERIA

This application is a national phase of International Application No. PCT/EP2019/073412 filed Sep. 3, 2019 and published in the English language, which claims priority to Luxembourg application LU100918 filed Sep. 3, 2018, both of which are hereby incorporated herein by reference.

TECHNICAL FIELD

The present invention relates to compounds that demonstrate antibacterial activity, processes for their preparation, pharmaceutical compositions containing them as the active ingredient, to their use as medicaments and to their use in the manufacture of medicaments for use in the treatment of bacterial infections in humans and warm-blooded animals. In particular, this invention relates to compounds useful for the treatment of bacterial infections in humans, more particularly to the use of these compounds in the manufacture of medicaments for use in the treatment of bacterial infections in humans and warm-blooded animals.

BACKGROUND ART

The increasing number of life-threatening infections due to resistant Gram-positive and Gram-negative pathogens is becoming more and more alarming (Strachan, C. R. et al. Cold Spring Harb Perspect Med, 2017, 7; Brown, E. D. et al. *Nature*, 2016, 529, 336). In last 50 years, only a small number of new chemical classes of antibacterial agents have reached clinical practice, while at the same time, the number of multi-drug resistant (MDR) bacteria is rising (Klahn, P. et al. *Curr Top Microbiol Immunol*, 2016, 398, 365). Examples of such difficult-to-treat bacteria include pathogens of the "ESKAPE" group (*Enterococcus faecium, Staphylococcus aureus, Klebsiella pneumoniae, Acinetobacter baumannii, Pseudomonas aeruginosa*, and *Enterobacter* species) (Tommasi, R., et al., Nat Rev Drug Discov, 2015, 14, 529).

Bacterial topoisomerases, DNA gyrase and topoisomerase IV, are enzymes that catalyse changes in DNA topology during DNA replication, transcription and recombination and are essential for bacterial growth. They are absent in higher eukaryotes, which makes them suitable targets for antibacterial drug discovery. DNA gyrase regulates the supercoiling of DNA and relieves the stress that results after unwinding of the DNA double strand. DNA gyrase is a tetrameric protein that consists of two A subunits (GyrA) and two B subunits (GyrB). The main function of GyrA is to cleave and reunite the DNA molecule, while GyrB possesses the ATP-binding site that provides the energy for the catalytic process. The binding and hydrolysis of ATP cause a change in the structure of the DNA-bound DNA gyrase, which enables the supercoiling reaction. The structure of topoisomerase IV is similar to DNA gyrase with two ParC subunits that are similar in amino acid sequence and function to GyrA and two ParE subunits that are similar to GyrB. The main function of topoisomerase IV is to decatenate the two daughter chromosomes after replication (Mayer, C. et al. *Chem Rev*, 2014, 114, 2313; Tomašič, T. et al., *Curr Top Med Chem*, 2014, 14, 130).

Drugs targeting DNA gyrase and topoisomerase IV act by two main mechanisms (Collin, F. et al., *Appl Microbiol Biotechnol*, 2011, 92, 479). The first is stabilizing the complex between the DNA molecule and the DNA gyrase/topoisomerase IV through binding to the GyrA/ParC active site of the enzyme. This is the mechanism by which fluoroquinolones inhibit DNA replication and induce cell death and consequently antibacterial activity. The second mechanism, which is so far less exploited, is inhibiting the ATPase activity of the ParE/GyrB subunit. The first representatives of this mechanistic class were aminocoumarins e.g. novobiocin and clorobiocin. Novobiocin remains the only ATP-competitive GyrB/ParE inhibitor that has reached the clinic but it was withdrawn due to its toxicity and low effectiveness. Subsequent studies of many co-crystal structures of ParE and GyrB subunits with small ligands and fragment-based design campaigns have led to several new classes of GyrB/ParE inhibitors, such as benzothiazoles (Gjorgjieva, M. et al., *J Med Chem*, 2016, 59, 8941), pyrrolopyrimidines (Trzoss, M. et al., *Bioorg Med Chem Lett*, 2013, 23, 1537), indazoles (Zhang, J., et al., *ACS Med Chem Lett*, 2015, 6, 1080), p-aminobenzoates (Durcik, M. et al., *Chem Med Chem*, 2018, 13, 186), pyrimidoindoles (Tari, L. W. et al., *PLoS One*, 2013, 8, p. e84409) and azaindole ureas (Zhang, J. et al., *J Med Chem*, 2015, 58, 8503). However, none of them has advanced beyond phase I clinical trials, and most are only active against Gram-positive bacteria (Bisacchi, G. S. et al., *ACS Infect Dis*, 2015, 1, 4). Many of these compounds have problems of insufficient activity, low water solubility, cytotoxicity, or production of reactive metabolites. Therefore, there is a need for the development of novel effective GyrB/ParE inhibitors that do not possess the disadvantages of the known inhibitors. Such new inhibitors are urgently needed in the fight against the spread of resistant bacteria.

Synthetic DNA gyrase inhibitors that target the GyrB subunit of DNA gyrase and/or ParE subunit of topoisomerase IV are known in the previous art. For example, coumarin-containing compounds are described in patent application WO 99/35155, 5,6-bicyclic heteroaromatic compounds are described in patent application WO 02/060879, pyrazole compounds are described in patent application WO 01/52845 (U.S. Pat. No. 6,608,087) as well as in Daiichi Sankyo patents WO 2017/056012 A1 and WO2009084614A1. AstraZeneca has also published many applications describing antibacterial compounds, e.g. WO2005/026149, WO2006/087544, WO2006/087548, WO2006/087543, WO/2006/092599, WO2006/092608, WO 2007071965, WO2008/020227, WO2008/020229, WO2008/020222, WO2008/152418, WO2009/147431, WO2010/067125 and WO2010/067123. We have also previously published a paper describing benzothiazole-based DNA gyrase and topoisomerase IV inhibitors, but these were inactive in antibacterial assays (Gjorgjieva, M. et al., *J. Med. Chem.*, 2016, 59, 8941-8954).

The present invention relates to the discovery of new DNA gyrase/topoisomerase IV inhibitors with antibacterial activity against Gram-positive and/or Gram-negative bacterial strains.

SUMMARY

We have discovered a new class of compounds that are useful for inhibiting ATPase domains of DNA gyrase and/or topoisomerase IV. The compounds of the present invention are effective against both Gram-positive and Gram-negative pathogens.

The present invention relates to a compound of formula (I):

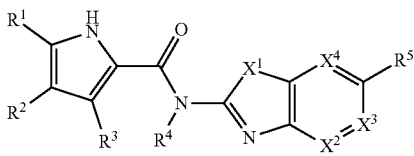

wherein $R^1$, $R^2$, $R^3$, $R^4$, $R^5$, $X^1$, $X^2$ and $X^3$ are as defined herein, and their pharmaceutically acceptable salts, racemates, diastereomers, enantiomers, esters, carbamates, sulphates, phosphates and prodrugs thereof.

Particularly, the present invention can be summarized by the following items:

1. A compound of formula (I):

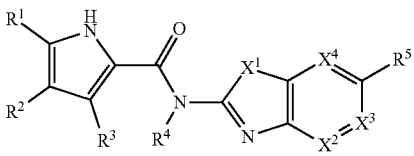

wherein:

$R^1$, $R^2$ and $R^3$ are each independently selected from H, halogen, —CN, $CF_3$, amino, methylamino, ethylamino, optionally substituted $C_{1-6}$ alkyl, optionally substituted $C_{1-6}$ alkoxy, and optionally substituted $C_{3-6}$ cycloalkyl;

$R^4$ is $(CH_2)_{0-6}$-A wherein A is H, carboxyl, $NR^6R^7$ or is selected from optionally substituted monocyclic $C_{3-7}$ cycloalkyl, optionally substituted monocyclic $C_{3-7}$ cycloalkenyl, optionally substituted saturated or unsaturated monocyclic 3-7 membered heterocycle, optionally substituted saturated or unsaturated fused bicyclic 8-10 membered-heterocycle, optionally substituted $C_6$-10 aryl and optionally substituted 5-10 membered heteroaryl;

$R^5$ is (hydroxyimino)methyl, —CO—$C_{2-6}$ alkyl, —CO—$C_{2-6}$ alkenyl, —CO—$C_{2-6}$ alkynyl, carboxyl, —COO—$C_{2-6}$ alkyl, —CONR$^6$R$^7$, —OCONR$^6$R$^7$, —OCO—$C_{2-6}$ alkyl, —COO—$C_{2-6}$ alkyl (optionally substituted with —COO—$C_{2-6}$ alkyl), —CONHCH(CO$_2$R$^7$)R$^6$, —(CH$_2$)$_{0-6}$OH, —O—$C_{2-6}$ alkyl, hydroxyl-$C_{1-6}$ alkyl, heterocyclyl, aryl, —C(=NOR$^7$)$C_{2-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or $C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and optionally substituted $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-6}$ alkyl, $C_2$-6 alkenyl, $C_2$-6 alkynyl, hydroxyl, $C_{1-6}$ alkoxy, halogen, cyano, nitro, carboxyl, hydroxy-$C_{1-6}$ alkyl-, $C_{1-6}$ alkoxy-$C_{1-6}$ alkyl, halogen-$C_{1-6}$ alkyl-, difluoromethyl, trifluoromethyl, formyl, —CO—$C_{1-6}$ alkyl, —COO—$C_{2-6}$ alkyl, —C(O)NH$_2$, —C(O)NH—$C_{1-6}$ alkyl, —C(O)N[$C_{2-6}$ alkyl]$_2$, —SO$_2$NH$_2$, —SO$_2$NH—$C_{1-6}$ alkyl, —SO$_2$N[$C_{2-6}$alkyl]$_2$ and S(O)p-$C_{1-6}$ alkyl;

p is (independently at each occurrence) 0, 1 or 2;

$X^1$ is S, O or NH;

$X^2$ is N or $CR^8$, preferably $CR^8$;

$X^3$ is N or $CR^8$, preferably $CR^8$;

$X^4$ is N or $CR^8$, preferably $CR^8$;

$R^8$ is H, hydroxy, halogen, carboxyl, $C_{1-6}$ alkyl, $C_2$-6 alkenyl, $C_2$-6 alkynyl, $(CH_2)_mO$—$C_{1-6}$ alkyl, $(CH_2)_mS$—$C_{1-6}$ alkyl, $(CH_2)_mS(=O)$—$C_{1-6}$ alkyl, $(CH_2)_mO(CH_2)_m$—$C_{3-2}$ cycloalkyl, $(CH_2)_m$—$C_{3-2}$ cycloalkyl, $(CH_2)_mO(CH_2)_m$aryl, $(CH_2)_mO(CH_2)_m$-5-10-membered heterocycle, $(CH_2)_m$-5-10-membered heterocycle, halogen-$C_{1-6}$ alkyl, cyano or $(CH_2)_mNR^9R^{10}$, wherein each m is an integer independently selected from 0, 1, 2 and 3, and wherein any alkyl, alkenyl, alkynyl, cycloalkyl, heterocycle or aryl may be optionally substituted;

$R^9$ and $R^{10}$ are each independently selected from H or $C_{1-6}$ alkyl, $C_3$-6 cycloalkyl and 4-6-membered heterocyclyl, wherein any alkyl, cycloalkyl or heterocyclyl may be optionally substituted, or $R^9$ and $R^{10}$ join together to form an optionally substituted 4-6-membered heterocyclyl and where each m is an integer independently selected from 0, 1, 2 and 3;

or a pharmaceutically acceptable salt, racemate, diastereomer, enantiomer, ester, carbamate, sulphate, phosphate or prodrug thereof.

2. The compound of according to item 1, wherein $R^1$, $R^2$ and $R^3$ are each independently selected from H, halogen, —CN, —CF$_3$, optionally substituted $C_{1-4}$ alkyl, optionally substituted $C_{1-4}$ alkoxy and optionally substituted $C_{3-6}$ cycloalkyl;

$R^4$ is $(CH_2)_{0-6}$-A wherein A is H, carboxyl, $NR^6R^7$ or is selected from optionally substituted monocyclic $C_{3-7}$ cycloalkyl, optionally substituted monocyclic $C_{3-7}$ cycloalkenyl, optionally substituted saturated or unsaturated monocyclic 3-7 membered heterocycle, optionally substituted saturated or unsaturated fused bicyclic 8-10 membered-heterocycle, optionally substituted $C_{6-10}$ aryl and optionally substituted 5-10 membered heteroaryl;

$R^5$ is (hydroxyimino)methyl, —CO—$C_{1-6}$ alkyl, —CO—$C_{2-4}$ alkenyl, —CO—$C_{2-4}$ alkynyl, carboxyl, —COO—$C_{1-4}$ alkyl, —CONR$^6$R$^7$, —OCONR$^6$R$^7$, —OCO—$C_{1-4}$ alkyl, —COO—$C_{1-4}$ alkyl (optionally substituted with —COO—$C_{1-4}$ alkyl), —CONHCH(CO$_2$R$^7$)R$^6$, —(CH$_2$)$_{0-6}$OH, —O—$C_{1-4}$ alkyl, hydroxyl-$C_{1-4}$ alkyl, heterocyclyl, aryl, —C(=NOR$^7$)$C_{1-4}$ alkyl, —C(=NOR$^7$)NR$^6$R$^7$, —S(O)pNR$^6$R$^7$, —S(O)p-$C_{1-4}$ alkyl-CONHR$^7$, —C(O)NHS(O)p-$C_{1-4}$ alkyl, —C(O)NHS(O)p-aryl, —CH$_2$CH(COOR$^6$)OH, —$C_{1-4}$ alkyl-CH(NR$^6$R$^7$)COOR$^6$ or —$C_{1-4}$ alkyl-CH(NR$^6$R$^7$)CONR$^6$R$^7$), wherein any alkyl, alkenyl, alkynyl, heterocyclyl or aryl may be optionally substituted;

$R^6$ and $R^5$ are independently at each occurrence selected from H and optionally substituted $C_{1-4}$ alkyl;

or $R^6$ and $R^7$ may together with the nitrogen to which they are attached form a 5 or 6-membered heterocyclic ring, optionally substituted with 1 or 2 substituents independently selected from $C_{1-4}$ alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-4}$ alkyl-, $C_{1-4}$ alkoxy-$C_{1-4}$ alkyl, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-6}$ alkyl, —SO$_2$N[$C_{1-4}$ alkyl]$_2$ and —S(O)p-$C_{1-4}$ alkyl;

p is (independently at each occurrence) 0, 1 or 2;
$X^1$ is S, O or NH;
$X^2$ is N or C—$R^8$, preferably C—$R^8$;
$X^3$ is N or C—$R^8$, preferably C—$R^8$;
$X^4$ is N or C—$R^8$, preferably C—$R^8$;
$R^8$ is H, hydroxy, halogen, carboxyl, $C_{1-6}$ alkyl, $C_{2-6}$ alkenyl, $C_{2-6}$ alkynyl, $(CH_2)_mO$—$C_{1-6}$ alkyl, $(CH_2)_m$S—$C_{1-6}$ alkyl, $(CH_2)_mS(=O)$—$C_{1-6}$ alkyl, $(CH_2)_mO(CH_2)_m$—$C_{3-7}$ cycloalkyl, $(CH_2)_m$—$C_{3-7}$ cycloalkyl, $(CH_2)_mO(CH_2)_m$aryl, $(CH_2)_mO(CH_2)_m$-5-10-membered heterocycle, $(CH_2)_m$-5-10-membered heterocycle, halogen-$C_{1-6}$ alkyl, cyano or $(CH_2)_mNR^9R^{10}$, wherein each m is an integer independently selected from 0, 1, 2 and 3, and wherein any alkyl, alkenyl, alkynyl, cycloalkyl, heterocycle or aryl may be optionally substituted;
$R^9$ and $R^{10}$ are each independently selected from H or $C_{1-4}$ alkyl, $C_{3-6}$ cycloalkyl and 4-6-membered heterocyclyl, wherein any alkyl, cycloalkyl or heterocyclyl may be optionally substituted, or $R^9$ and $R^{10}$ join together to form an optionally substituted 4-6-membered heterocyclyl and where each m is an integer independently selected from 0, 1, 2 and 3.

3. The compound of item 1 or 2, wherein one of $R^1$, $R^2$ and $R^3$ is not H.
4. The compound of any one of items 1 to 3, wherein two of $R^1$, $R^2$ and $R^3$ are halogen, preferably selected from bromo and chloro.
5. The compound of any one of items 1 to 4, wherein $R^1$ is methyl.
6. The compound of any one of items 1 to 5, wherein $R^2$ and $R^3$ are chloro.
7. The compound of any one of items 1 to 5, wherein $R^2$ and $R^3$ are fluoro.
8. The compound of any one of items 1 to 5, wherein only one of $R^2$ and $R^3$ is chloro.
9. The compound of any one of items 1 to 5, wherein only one of $R^2$ and $R^3$ is fluoro.
10. The compound of any one of items 1 to 4, wherein $R^1$ and $R^2$ are bromo.
11. The compound of any one of items 1 to 10, wherein $R^4$ is H.
12. The compound of any one of items 1 to 10, wherein $R^4$ is $(CH_2)_{1-6}$-A.
13. The compound of any one of items 1 to 12, wherein only one of $X^2$, $X^3$ and $X^4$ can be N.
14. The compound of any one of items 1 to 13, wherein $X^2$ is C—$R^8$.
15. The compound of any one of items 1 to 14, wherein $X^3$ and $X^4$ are CH, or $X^2$, $X^3$ and $X^4$ are CH.
16. The compound of any one of items 1 to 15, wherein $X^1$ is sulphur.
17. The compound of any one of items 1 to 16, wherein $R^5$ is carboxyl.
18. The compound of item 1, wherein:
   $R^1$ is methyl;
   $R^2$ and $R^3$ are each independently selected from chloro, bromo or fluoro;
   $R^4$ is hydrogen;
   $R^5$ is carboxyl;
   $X^1$ is S or NH or O;
   $X^2$, $X^3$ and $X^4$ are CH.
19. The compound of item 1, wherein:
   $R^1$ is methyl;
   $R^2$ and $R^3$ are each independently selected from chloro, bromo or fluoro;
   $R^4$ is selected from hydrogen, —$(CH_2)_{1-6}$-A, wherein A is optionally substituted aryl or optionally substituted heterocyclyl;
   $R^5$ is carboxyl;
   $X^1$ is S or NH or O;
   $X^2$, $X^3$ and $X^4$ are CH.
20. The compound of item 1, wherein:
   $R^1$ is methyl;
   $R^2$ and $R^3$ are each independently selected from chloro, bromo or fluoro;
   $R^4$ is hydrogen;
   $R^5$ is carboxyl;
   $X^1$ is S, NH or O;
   $X^2$ is C—$R^8$, wherein $R^3$ is selected from —O—$(CH_2)_{0-4}$—$CH_3$, fluoro, hydroxyl, optionally substituted —O—$(CH_2)_{0-4}$ aryl or optionally substituted —O—$(CH_2)_{0-4}$ heterocyclyl;
   $X^3$ and $X^4$ are CH.
21. A compound according to item 1, which is selected from the group consisting of:
2-(3,4-dichloro-5-methyl-1H-pyrrole-2-carboxamido)benzo[d]thiazole-6-carboxylic acid,
2-(4,5-dibromo-1H-pyrrole-2-carboxamido)benzo[d]thiazole-6-carboxylic acid,
2-(4,5-dichloro-1H-pyrrole-2-carboxamido)benzo[d]thiazole-6-carboxylic acid,
2-(3,4-dichloro-5-methyl-1H-pyrrole-2-carboxamido)benzo[d]thiazole-5-carboxylic acid,
2-(3,4-dichloro-5-methyl-1H-pyrrole-2-carboxamido)-4-fluorobenzo[d]thiazole-6-carboxylic acid,
2-(4,5-dibromo-1H-pyrrole-2-carboxamido)-4-hydroxybenzo[d]thiazole-6-carboxylic acid,
2-(3,4-dichloro-5-methyl-1H-pyrrole-2-carboxamido)-4-hydroxybenzo[d]thiazole-6-carboxylic acid,
2-(3,4-dichloro-5-methyl-1H-pyrrole-2-carboxamido)-4-methoxybenzo[d]thiazole-6-carboxylic acid,
4-(benzyloxy)-2-(3,4-dichloro-5-methyl-1H-pyrrole-2-carboxamido)benzo[d]thiazole-6-carboxylic acid,
4-(2-((6-carboxy-2-(3,4-dichloro-5-methyl-1H-pyrrole-2-carboxamido)benzo[d]thiazol-4-yl)oxy)ethyl)morpholin-4-ium chloride,
2-((6-carboxy-2-(3,4-dichloro-5-methyl-1H-pyrrole-2-carboxamido)benzo[d]thiazol-4-yl)oxy)ethan-1-aminium chloride,
4-((4-carboxybenzyl)oxy)-2-(3,4-dichloro-5-methyl-1H-pyrrole-2-carboxamido)benzo[d]thiazole-6-carboxylic acid,
2-(3,4-dichloro-5-methyl-1H-pyrrole-2-carboxamido)-5-hydroxybenzo[d]thiazole-6-carboxylic acid,
7-chloro-2-(3,4-dichloro-5-methyl-1H-pyrrole-2-carboxamido)benzo[d]thiazole-6-carboxylic acid,
2-(N-benzyl-4,5-dibromo-1H-pyrrole-2-carboxamido)benzo[d]thiazole-6-carboxylic acid,
2-(N-benzyl-3,4-dichloro-5-methyl-1H-pyrrole-2-carboxamido)benzo[d]thiazole-6-carboxylic acid,
N-(6-(1H-tetrazol-5-yl)benzo[d]thiazol-2-yl)-3,4-dichloro-5-methyl-1H-pyrrole-2-carboxamide,
2-(3,4-dichloro-5-methyl-1H-pyrrole-2-carboxamido)benzo[d]thiazole-6-carboxamide,
2-(4,5-dibromo-1H-pyrrole-2-carboxamido)-N-hydroxybenzo[d]thiazole-6-carboxamide,
2-(3,4-dichloro-5-methyl-1H-pyrrole-2-carboxamido)-N-hydroxybenzo[d]thiazole-6-carboxamide,
3-(2-(4,5-dibromo-1H-pyrrole-2-carboxamido)benzo[d]thiazole-6-carboxamido)propanoic acid,
3-(2-(3,4-dichloro-5-methyl-1H-pyrrole-2-carboxamido)benzo[d]thiazole-6-carboxamido)propanoic acid, (2-(3,4-dichloro-5-methyl-1H-pyrrole-2-carboxamido)
benzo[d]thiazole-6-carbonyl)glycine,
4-((3-carboxybenzyl)oxy)-2-(3,4-dichloro-5-methyl-1H-
pyrrole-2-carboxamido)benzo[d]thiazole-6-carboxylic
acid,
4-(2-((6-((cyanomethyl)carbamoyl)-2-(3,4-dichloro-5-
methyl-1H-pyrrole-2-carboxamido)benzo[d]thiazol-4-yl)
oxy)ethyl)morpholin-4-ium chloride,
N-(cyanomethyl)-2-(3,4-dichloro-5-methyl-1H-pyrrole-2-
carboxamido)benzo[d]thiazole-6-carboxamide,
4-(benzyloxy)-N-(cyanomethyl)-2-(3,4-dichloro-5-methyl-
1H-pyrrole-2-carboxamido)benzo[d]thiazole-6-carbox-
amide,
4-(benzyloxy)-2-(3,4-dichloro-5-methyl-1H-pyrrole-2-car-
boxamido)benzo[d]thiazole-6-carboxamide,
N-(4-(benzyloxy)-6-(1H-tetrazol-5-yl)benzo[d]thiazol-2-
yl)-3,4-dichloro-5-methyl-1H-pyrrole-2-carboxamide,
2-(3,4-dichloro-5-methyl-1H-pyrrole-2-carboxamido)-4-
((3-fluorobenzyl)oxy)benzo[d]thiazole-6-carboxylic acid,
2-(3,4-dichloro-5-methyl-1H-pyrrole-2-carboxamido)-4-
(thiophen-3-ylmethoxy)benzo[d]thiazole-6-carboxylic
acid,
2-(3,4-dichloro-5-methyl-1H-pyrrole-2-carboxamido)-4-
(thiophen-2-ylmethoxy)benzo[d]thiazole-6-carboxylic
acid,
methyl (S)-4-(3-((tert-butoxycarbonyl)amino)pyrrolidin-1-
yl)-2-(3,4-dichloro-5-methyl-1H-pyrrole-2-carboxamido)
benzo[d]thiazole-6-carboxylate,
(S)-1-(2-(3,4-dichloro-5-methyl-1H-pyrrole-2-carbox-
amido)-6-(methoxycarbonyl)benzo[d]thiazol-4-yl)pyrro-
lidin-3-aminium chloride,
(S)-4-(3-((tert-butoxycarbonyl)amino)pyrrolidin-1-yl)-2-(3,
4-dichloro-5-methyl-1H-pyrrole-2-carboxamido)benzo
[d]thiazole-6-carboxylic acid,
(S)-1-(6-carboxy-2-(3,4-dichloro-5-methyl-1H-pyrrole-2-
carboxamido)benzo[d]thiazol-4-yl)pyrrolidin-3-aminium
chloride,
2-(3,4-dichloro-5-methyl-1H-pyrrole-2-carboxamido)-4-
(pyrrolidin-1-yl)benzo[d]thiazole-6-carboxylic acid,
2-(4,5-dibromo-1H-pyrrole-2-carboxamido)-4-((5-hydroxy-
4-oxo-1,4-dihydropyridin-2-yl)methoxy)benzo[d]thiaz-
ole-6-carboxylic acid,
(5-hydroxy-4-oxo-4H-pyran-2-yl)methyl 2-(4,5-dibromo-
1H-pyrrole-2-carboxamido)benzo[d]thiazole-6-carboxy-
late,
(5-hydroxy-4-oxo-1,4-dihydropyridin-2-yl)methyl 2-(4,5-
dibromo-1H-pyrrole-2-carboxamido)benzo[d]thiazole-6-
carboxylate,
2-(3,4-dichloro-N-isopropyl-5-methyl-1H-pyrrole-2-car-
boxamido)benzo[d]thiazole-6-carboxylic acid,
2-(3,4-dichloro-N-cyclopropyl-5-methyl-1H-pyrrole-2-car-
boxamido)benzo[d]thiazole-6-carboxylic acid,
2-(3,4-dichloro-N-ethyl-5-methyl-1H-pyrrole-2-carbox-
amido)benzo[d]thiazole-6-carboxylic acid,
2-(3,4-dichloro-5-methyl-1H-pyrrole-2-carboxamido)-4-
phenylbenzo[d]thiazole-6-carboxylic acid and
2-(4-bromo-3-chloro-5-methyl-1H-pyrrole-2-carboxamido)
benzo[d]thiazole-6-carboxylic acid;
22. The compound of any one of items 1 to 21 for use in
medicine.
23. The compound of any one of items 1 to 22 for use in
the treatment of a bacterial infection in a warm-blooded
animal.
24. The compound for use of item 23, wherein the
warm-blooded animal is a human.
25. The compound for use of item 23 or 24, wherein the
bacterial infection is selected from the group consisting
of community-acquired pneumonia, hospital-acquired
pneumonia, skin and skin structure infections, acute
exacerbation of chronic brionchitis, conjunctivitis,
meningitis, gastrointestinal tract infections, pelvic
inflammatory disease, acute sinusitis, acute otitis
media, bloodstream infections (bacteraemia), catheter-
related sepsis, febrile neutropenia, osteomyelitis, endo-
carditis, urinary tract infections and infections caused
by drug resistant bacteria.
26. The compound for use of any one of items 23 to 25,
wherein the bacterial infection is caused by a Gram-
negative, a Gram-positive, or a Gram-variable bacte-
rium.
27. The compound for use of any one of items 23 to 25,
wherein the bacterial infection is caused by a Gram-
negative bacterium.
28. The compound for use of any one of items 23 to 25,
wherein the bacterial infection is caused by a a Gram-
positive bacterium.
29. The compound for use of any one of items 23 to 25,
wherein the bacterial infection is caused by a Gram-
variable bacterium.
30. The compound for use of any one of items 23 to 25,
wherein the bacterial infection is caused by a patho-
genic bacterium, an opportunistic bacterial pathogen,
or other bacterium.
31. The compound for use of any one of items 23 to 25,
wherein the bacterial infection is caused by any of the
bacteria selected from the group of *Clostridium* spe-
cies, including *Clostridium difficile, Clostridium per-
fringens* and *Clostridium tetani, Bacillus* species,
including *Bacillus anthracis, Haemophilus* species
including *Haemophilus influenzae, Helicobacter* spe-
cies, including *Helicobacter pylori, Neisseria* species,
including *Neisseria gonorrhoeae* and including drug-
resistant *Neisseria gonorrhoeae*, the Enterobacteri-
aceae family, including Carbapenem-resistant Entero-
bacteriaceae (CRE), extended spectrum β-lactamase
producing Enterobacteriaceae (ESBLs), *Enterobacter*
species, including *Enterobacter cloacae, Enterobacter
aerogenes, Salmonella* species, including drug-resis-
tant Non-typhoidal *Salmonella* and *Salmonella Typhi,
Shigella*, including drug-resistant *Shigella, Citrobacter*
species, *Escherichia* species, including *Escherichia
coli*, including Enterotoxigenic *E. coli* (ETEC),
Enteropathogenic *E. coli* (EPEC), uropathogenic *E.
coli* (UPEC), Enteroinvasive *E. coli* (EIEC), Enterohe-
morrhagic *E. coli* (EHEC), *Acinetobacter* species,
including *Acinetobacter baumannii*, drug- and multi-
drug-resistant *Acinetobacter, Enterococcus* species,
including Vancomycin-resistant *Enterococcus* (VRE),
*Enterococcus faecium, Enterococcus faecalis,
Pseudomonas* species, including *Pseudomonas aerugi-
nosa*, including drug- and multidrug-resistant
*Pseudomonas aeruginosa, Staphylococcus aureus*,
including methicillin-resistant *Staphylococcus aureus*
(MRSA) and Vancomycin-resistant *Staphylococcus
aureus* (VRSA), *Staphylococcus epidermidis* and
methicillin-resistant *Staphylococcus epidermidis*
(MRSE), *Staphylococcus haemolyticus, Staphylococ-
cus saprophyticus, Streptococcus* species and their
drug-resistant variants, including *Streptococcus aga-
lactiae, Streptococcus pyogenes, Streptococcus pneu-
moniae* and including their drug-resistant variants.
32. The compound for use of any one of items 23 to 25,
wherein the bacterial infection is caused by any of the
ESKAPE pathogens, including *Enterococcus faecium*,

*Staphylococcus aureus, Klebsiella pneumoniae, Acinetobacter baumannii, Pseudomonas aeruginosa, Enterobacter* species or any of their drug-resistant variants.

33. A pharmaceutical composition comprising a compound of any one of items 1 to 21 and a pharmaceutically acceptable excipient or carrier.
34. A method of inhibiting bacterial DNA gyrase and/or bacterial topoisomerase IV in a warm-blooded animal in need of such treatment, comprising administering to the animal an effective amount of compound of any one of items 1 to 21.
35. A method of producing an antibacterial effect in a warm-blooded animal in need of such treatment, comprising administering to the animal an effective amount of compound of any one of claims 1 to 21.
36. A method of treating a bacterial infection in a warm-blooded animal in need thereof, comprising administering to the animal an effective amount of compound of any one of items 1 to 21.
37. The method of item 36, wherein the bacterial infection is selected from the group consisting of community-acquired pneumonia, hospital-acquired pneumonia, skin and skin structure infections, acute exacerbation of chronic brionchitis, conjunctivitis, meningitis, gastro-intestinal tract infections, pelvic inflammatory disease, acute sinusitis, acute otitis media, bloodstream infections (bacteraemia), catheter-related sepsis, febrile neutropenia, osteomyelitis, endocarditis, urinary tract infections and infections caused by drug resistant bacteria.
38. The method of item 36, wherein the bacterial infection is caused by a Gram-negative, a Gram-positive, or a Gram-variable bacterium.
39. The method of item 36, wherein the bacterial infection is caused by a Gram-negative bacterium.
40. The method of item 36, wherein the bacterial infection is caused by a Gram-positive bacterium.
41. The method of item 36, wherein the bacterial infection is caused by a Gram-variable bacterium.
42. The method of item 36, wherein the bacterial infection is caused by a pathogenic bacterium, an opportunistic bacterial pathogen, or other bacterium.
43. The method of item 36, wherein the bacterial infection is caused by any of the bacteria selected from the group of *Clostridium* species, including *Clostridium difficile, Clostridium perfringens* and *Clostridium tetani, Bacillus* species, including *Bacillus anthracis, Haemophilus* species including *Haemophilus influenzae, Helicobacter* species, including *Helicobacter pylori, Neisseria* species, including *Neisseria gonorrhoeae* and including drug-resistant *Neisseria gonorrhoeae*, the Enterobacteriaceae family, including Carbapenem-resistant Enterobacteriaceae (CRE), extended spectrum β-lactamase producing Enterobacteriaceae (ESBLs), *Enterobacter* species, including *Enterobacter cloacae, Enterobacter aerogenes, Salmonella* species, including drug-resistant Non-typhoidal *Salmonella* and *Salmonella Typhi, Shigella*, including drug-resistant *Shigella, Citrobacter* species, *Escherichia* species, including *Escherichia coli*, including Enterotoxigenic *E. coli* (ETEC), Enteropathogenic *E. coli*, Enteroinvasive *E. coli* (EIEC), Enterohemorrhagic *E. coli* (EHEC), *Acinetobacter* species, including *Acinetobacter baumannii*, drug- and multidrug-resistant *Acinetobacter, Enterococcus* species, including Vancomycin-resistant *Enterococcus* (VRE), *Enterococcus faecium, Enterococcus faecalis, Pseudomonas* species, including *Pseudomonas aeruginosa*, including drug- and multidrug-resistant *Pseudomonas aeruginosa, Staphylococcus aureus*, including methicillin-resistant *Staphylococcus aureus* (MRSA) and Vancomycin-resistant *Staphylococcus aureus* (VRSA), *Staphylococcus epidermidis* and methicillin-resistant *Staphylococcus epidermidis* (MRSE), *Staphylococcus haemolyticus, Staphylococcus saprophyticus, Streptococcus* species and their drug-resistant variants, including *Streptococcus agalactiae, Streptococcus pyogenes, Streptococcus pneumoniae* and including their drug-resistant variants.
44. The method of item 36, wherein the bacterial infection is caused by any of the ESKAPE pathogens, including *Enterococcus faecium, Staphylococcus aureus, Klebsiella pneumoniae, Acinetobacter baumannii, Pseudomonas aeruginosa, Enterobacter* species or any of their drug-resistant variants.
45. The method of any one of items 34 to 44, wherein the warm-blooded animal is a human.
46. The use of a compound of any one of items 1 to 21 for the manufacture of a medicament for use for the production of an antibacterial effect in a warm-blooded animal.
47. The use of a compound of any one of items 1 to 21 for the manufacture of a medicament for use in inhibition of bacterial DNA gyrase and/or topoisomerase IV in a warm-blooded animal.
48. The use of a compound of any one of items 1 to 21 for the manufacture of a medicament for use for the treatment of a bacterial infection in a warm-blooded animal.
49. The use of item 48, wherein the bacterial infection is selected from the group consisting of community-acquired pneumonia, hospital-acquired pneumonia, skin and skin structure infections, acute exacerbation of chronic brionchitis, conjunctivitis, meningitis, gastro-intestinal tract infections, pelvic inflammatory disease, acute sinusitis, acute otitis media, bloodstream infections (bacteraemia), catheter-related sepsis, febrile neutropenia, osteomyelitis, endocarditis, urinary tract infections and infections caused by drug resistant bacteria.
50. The use of item 48 or 49, wherein the bacterial infection is caused by a Gram-negative, a Gram-positive, or a Gram-variable bacterium.
51. The use of item 48 or 49, wherein the bacterial infection is caused by a Gram-negative bacterium.
52. The use of item 48 or 49, wherein the bacterial infection is caused by a Gram-positive bacterium.
53. The use of item 48 or 49, wherein the bacterial infection is caused by a Gram-variable bacterium.
54. The use of item 48 or 49, wherein the bacterial infection is caused by a pathogenic bacterium, an opportunistic bacterial pathogen, or other bacterium.
55. The use of item 48 or 49, wherein the bacterial infection is caused by any of the bacteria selected from the group of *Clostridium* species, including *Clostridium difficile, Clostridium perfringens* and *Clostridium tetani, Bacillus* species, including *Bacillus anthracis, Haemophilus* species including *Haemophilus influenzae, Helicobacter* species, including *Helicobacter pylori, Neisseria* species, including *Neisseria gonorrhoeae* and including drug-resistant *Neisseria gonorrhoeae*, the Enterobacteriaceae family, including Carbapenem-resistant Enterobacteriaceae (CRE), extended spectrum β-lactamase producing Enterobacteriaceae (ESBLs), *Enterobacter* species, including Enterobacter cloacae, Enterobacter aerogenes, Salmonella species, including drug-resistant Non-typhoidal Salmonella and Salmonella Typhi, Shigella, including drug-resistant Shigella, Citrobacter species, Escherichia species, including Escherichia coli, including Enterotoxigenic E. coli (ETEC), Enteropathogenic E. coli, Enteroinvasive E. coli (EIEC), Enterohemorrhagic E. coli (EHEC), Acinetobacter species, including Acinetobacter baumannii, drug- and multidrug-resistant Acinetobacter, Enterococcus species, including Vancomycin-resistant Enterococcus (VRE), Enterococcus faecium, Enterococcus faecalis, Pseudomonas species, including Pseudomonas aeruginosa, including drug- and multidrug-resistant Pseudomonas aeruginosa, Staphylococcus aureus, including methicillin-resistant Staphylococcus aureus (MRSA) and Vancomycin-resistant Staphylococcus aureus (VRSA), Staphylococcus epidermidis and methicillin-resistant Staphylococcus epidermidis (MRSE), Staphylococcus haemolyticus, Staphylococcus saprophyticus, Streptococcus species and their drug-resistant variants, including Streptococcus agalactiae, Streptococcus pyogenes, Streptococcus pneumoniae and including their drug-resistant variants.

56. The use of item 48 or 49, wherein the bacterial infection is caused by any of the ESKAPE pathogens, including Enterococcus faecium, Staphylococcus aureus, Klebsiella pneumoniae, Acinetobacter baumannii, Pseudomonas aeruginosa, Enterobacter species or any of their drug-resistant variants.

57. The use of according to any one of items 46 to 56, wherein the warm-blooded animal is a human.

58. A process for preparing a compound as defined in any one of items 1 to 21 (with the variable groups being as defined in any of items 1 to 20), which process comprises:

Process step a) transformation of a compound of formula (II)

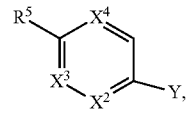

wherein Y is selected from nitro or amino or protected amino group,
to a compound of formula (III)

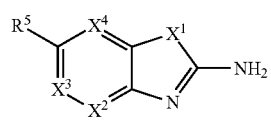

and
Process step b) coupling a compound of formula (III):

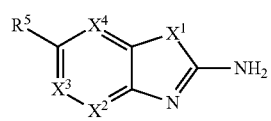

with a compound of formula (IV):

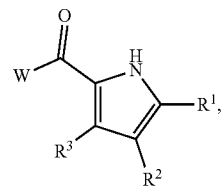

wherein W is selected from hydroxyl, halogen (preferably Cl, Br or I) and 1,1,1-trichloromethyl,
to a compound of formula (I):

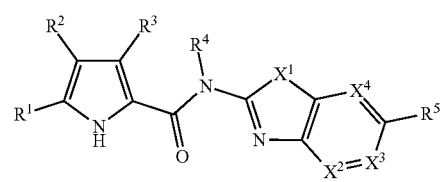

or

Process step c) for compounds of formula (Ia); reacting a compound of formula (I), wherein $R^6$ is —COO—$C_{1-6}$ alkyl (compound of formula (Ia)):

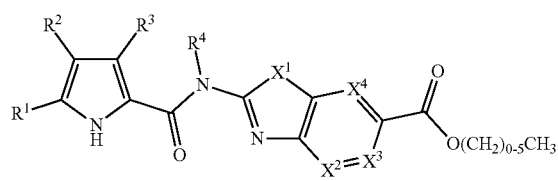

to a compound of formula (V).

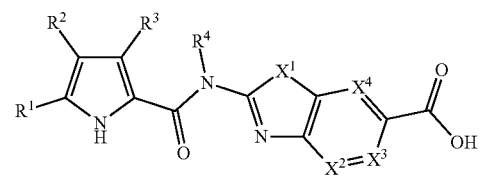

or

Process step d) reacting a compound of formula (V) with a compound of formula (VI):

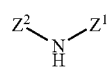

to a compound of formula (VII):

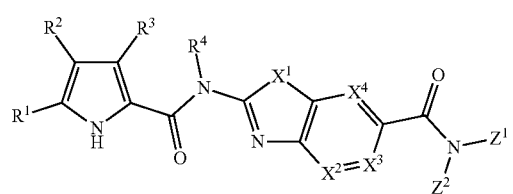

wherein $Z^1$ and $Z^2$ are independently selected from H, —$R^6R^7$, —$CH(CO_2R^7)R^6$, heterocyclyl, aryl.

BRIEF DESCRIPTION OF THE DRAWING

The FIGURE. In vivo activity of the compound of Example 1 against the USA300 mupirocin-resistant, methicillin-resistant *Staphylococcus aureus* (MRSA) (ATCC BAA-1556 bacterial strain) in a dermal model of animal infection. Y axis indicates bacterial cell count within the wound as log 10 colony forming unit (CFU)/skin wound.

DETAILED DESCRIPTION OF THE INVENTION

Definitions

In this specification the term alkyl includes both straight and branched chain alkyl groups but references to individual alkyl groups such as propyl are specific for the straight chain version only. An analogous convention applies to other generic terms. Unless otherwise stated the term alkyl advantageously refers to chains with 1-6 carbon atoms, preferably 1-4 carbon atoms. In this specification, the terms alkenyl, alkynyl and cycloalkenyl include all positional and geometrical isomers.

In this specification the term alkoxy means an alkyl group as defined herein before linked to an oxygen atom.

Where optional substituents are chosen from 0, 1, 2 or 3 groups it is to be understood that this definition includes all substituents being chosen from one of the specified groups or the substituents being chosen from two or more of the specified groups. An analogous convention applies to substituents chosen from 0, 1 or 2 groups; 1, 2 or 3 substituents; and 1 or 2 groups.

It is to be understood that where substituents contain two substituents on an alkyl chain, in which both are linked by a heteroatom (for example two alkoxy substituents), then these two substituents are not substituents on the same carbon atom of the alkyl chain. It will be understood that unstable compounds are not contemplated as part of this invention.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

Where "$R^6$ and $R^7$ may together with the nitrogen to which they are attached form a 5 or 6-membered heterocyclyl ring" said "5 or 6-membered heterocyclyl ring" is a saturated, partially saturated or fully unsaturated, monocyclic ring containing one nitrogen atom to which $R^6$ and $R^5$ are attached, and the other atoms are either all carbon atoms or they are carbon atoms and 1, 2 or 3 heteroatoms chosen from nitrogen, sulphur or oxygen, wherein a —$CH_2$— group can optionally be replaced by a —C(O)—, and a ring nitrogen atom or a ring sulphur atom may be optionally oxidised to form the N- and/or S-oxide(s). Examples and suitable values of "$R^6$ and $R^7$ may together with the nitrogen to which they are attached form a 5 or 6-membered heterocyclyl ring" are piperazinyl and morpholino.

Heterocyclyl is a saturated, partially saturated or unsaturated, optionally substituted monocyclic ring containing 5 to 7 atoms of which 1, 2, 3 or 4 ring atoms are chosen from nitrogen, sulphur or oxygen, which may, unless otherwise specified, be carbon or nitrogen linked, wherein a —$CH_2$— group can optionally be replaced by a —C(O)—, a ring sulphur atom may be optionally oxidised to form the S-oxide (s), and a ring nitrogen atom may be optionally oxidised to form the N-oxide. Examples and suitable values of the term heterocyclyl are morpholino, morpholinyl, piperidino, piperidyl, pyridyl, pyridyl-N-oxide, pyranyl, pyrrolyl, imidazolyl, thiazolyl, thienyl, dioxolanyl, thiadiazolyl, piperazinyl, isothiazolidinyl, triazolyl, tetrazolyl, pyrrolidinyl, 2-oxazolidinonyl, 5-isoxazolonyl, thiomorpholino, pyrrolinyl, homopiperazinyl, 3,5-dioxapiperidinyl, 3-oxopyrazolin-5-yl, tetrahydropyranyl, tetrahydrothiopyranyl, 1-oxotetrahydrothiopyranyl, 1,1-dioxotetrahydrothiopyranyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, oxadiazolyl, 2-[(5-oxo)-[oxa-3,4-diazolyl] and 3-[oxa-2,4-diazolyl].

Suitably a heterocyclyl is morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, 1,2,4-oxadiazolyl 2-[(5-oxo)-[oxa-3,4-diazolyl] and 3-[oxa-2,4-diazolyl].

Conveniently heterocyclyl is oxazolyl, 1,3,4-oxadiazolyl, 1,2,4-oxadiazolyl, 2-[(5-oxo)-[oxa-3,4-diazolyl], 3-[oxa-2,4-diazolyl], tetrazolyl, thiazolyl, thiadiazolyl, pyridyl, imidazolyl, furyl, thienyl, morpholine, pyrimidyl, pyrazinyl, pyridazinyl, pyrazolyl, pyrazolinyl, and piperazinyl.

Suitable optional substituents for heterocyclyl as a saturated or partially saturated ring are, unless otherwise defined, 1, 2 or 3 substituents independently selected from halogen, cyano, hydroxy, $C_{1-4}$ alkyl, $C_{1-4}$ alkoxy and $C_{1-4}$ alkylS(O)$_b$ (wherein b is 0, 1 or 2). Further suitable substituents for "heterocyclyl" as a saturated or partially saturated ring are 1, 2 or 3 substituents independently selected from fluoro, chloro, cyano, hydroxy, amino, carboxyl, methyl, ethyl, methoxy, methylthio, methylsulfinyl and methylsulfonyl.

Suitable optional substituents for heterocyclyl as an unsaturated ring are, unless otherwise defined, 1, 2 or 3 substituents independently selected from halogen, cyano, nitro, amino, hydroxy, $C_{1-4}$ alkyl, $C_{1-4}$ alkoxy, $C_{1-4}$ alkylS(O)$_b$ (wherein b is 0, 1 or 2), N—($C_{1-4}$ alkyl)amino and NN—($C_{1-4}$ alkyl)$_2$amino. Further suitable optional substituents for "heterocyclyl" as an unsaturated ring are 1, 2 or 3 substituents independently selected from fluoro, chloro, cyano, nitro, amino, carboxyl, methylamino, dimethylamino, hydroxy, methyl, ethyl, methoxy, methylthio, methylsulfinyl and methylsulfonyl.

For the avoidance of doubt, optional substituents on heterocyclyl groups are generally substituents on carbon atoms of the ring, but may where appropriate be on an N atom, for example N-alkylpyridine.

In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocyclyl", as used herein, pertains to a heterocyclyl group having 3, 4, 5, 6, 7, 8, 9 or 10 ring atoms or a range comprising any of two of those integers. Examples of heterocyclyl groups include 5-6-membered monocyclic heterocyclyls and 9-10 membered fused bicyclic heterocyclyls. Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring). Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O. "Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to four heteroatoms typically selected from nitrogen, sulfur and oxygen. The heteroaryl ring will contain up to 4 heteroatoms, more typically up to 3 heteroatoms, more usually up to 2, for example a single heteroatom. In one case, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered heteroaryl groups containing nitrogen include pyridyl (1 nitrogen), pyrazinyl, pyrimidinyl and pyridazinyl (2 nitrogens). It will be understood that, such as in the case of pyridyl when substituted with an oxo (=O) substituent the group may be interchangeably referred to as a pyridinone group.

Aromatic heterocyclyl groups may also be bicyclic or polycyclic heteroaromatic ring systems such as fused ring systems (including purinyl, pteridinyl, napthyridinyl, 1H-thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, naphthyl, indenyl, azulenyl, fluorenyl, anthracenyl and the like, such as 5- or 6-membered aromatic heterocyclyls fused to a phenyl ring including 5-membered aromatic heterocyclyls containing nitrogen fused to a phenyl ring, 5-membered aromatic heterocyclyls containing 1 or 2 nitrogens fused to a phenyl ring and such as 5- or 6-membered aromatic heteroaryls fused to a 6-membered aromatic or non-aromatic heterocyclyls.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms. Particular examples of bicyclic heteroaryl groups containing a five membered ring fused to another five membered ring i.e. 8-membered fused bicyclic rings include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring, i.e. 9-membered fused bicyclic rings include but are not limited to benzofuran, benzothiophene, benzimidazole, benzoxazole, isobenzoxazole, benzisoxazole, benzothiazole, benzoisothiazole, isobenzofuran, indole, isoindole, indolizine, indoline, isoindoline, purine (e.g. adenine, guanine), indazole, imidazopyridine (e.g. imidazo[1,2-a]pyridine and imidazo[4,5-b]pyridine], pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings i.e. 10-membered fused bicyclic rings include but are not limited to quinoline, isoquinoline, chroman, thiochroman, chromene (including those optionally substituted with oxo (=O) group e.g. oxochromene), isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from N, S and O.

Non-aromatic heterocyclyls may be 3-7 membered monocyclic rings. The term "3-7 membered monocyclic", as used herein, pertains to a mono-cyclic group having 3, 4, 5, 6 or 7 ring atoms or a range comprising any of two of those integers. Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihydropyranyl, tetrahydropyranyl, 2H-pyranyl, 4H-pyranyl, thianyl, thianyl oxide, thianyl dioxide, piperazinyl, dioxanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, naphthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like. The term "spiro ring system" means a bicyclic ring system in which the rings are connected via a single shared atom or "spiroatom" more particularly a quaternary carbon ("spiro carbon") and encompasses spiro bicyclic 7-11-membered carbocyclic rings and spiro bicyclic 7-11-membered heterocyclic rings containing one, two, three or four heteroatoms independently selected from O, N and S.

Examples of heterocyclyl-$C_{14}$ alkyl are morpholinomethyl, morpholinoethyl, morpholinylmethyl, morpholinylethyl, piperidinomethyl, piperidinoethyl, piperidylmethyl, piperidylethyl, imidazolylmethyl, imidazolylethyl, tetrazolylmethyl, tetrazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl.

Aryl is a partially saturated or unsaturated, mono or bicyclic carbon ring that contains 3-12 atoms; wherein a —CH$_2$— group can optionally be replaced by a —C(O)—. Particularly aryl is a monocyclic ring containing 5 or 6 atoms or a bicyclic ring containing 9 or 10 atoms. In another aspect aryl is a totally unsaturated ring. Suitable values for aryl include cyclopentenyl, cyclohexenyl, phenyl, naphthyl, indanyl or 1-oxoindanyl. Examples of aryl are optionally substituted phenyl and naphthyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated or partially saturated carbocycles having two carbon atoms in common. Particular cycloalkyl groups are cyclopropyl, cyclobutyl, cyclopentyl, cyclohexyl, cycloheptenyl, bicyclo[2.2.2]heptanyl, bicyclo[2.2.2]octanyl, cyclohexenyl, substituted bycyclo[2.2.2]heptanyl and substituted bicyclo[2.2.2]octenyl.

The term "halogengen" and "halogen" are used interchangeably herein and denote fluoro, chloro, bromo, or iodo. Particular halogengens are chloro and bromo. More particular halogengen is chloro.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydropyridinyl, or dihydropyranyl. Further particular examples of heterocycloalkyl group are 4,5-dihydro-oxazolyl and pyrrolidinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at carboxylic or hydroxy groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) can contain several asymmetric centers and can be present in the form of pure enantiomers, mixtures of enantiomers such as, for example, racemates, pure diastereoisomers, and mixtures of diastereoisomers.

The term "sulfate" refers to the group OS(O)$_2$OH and includes groups having the hydrogen replaced with, for example a $C_{1-6}$ alkyl group ("alkylsulfates"), an aryl ("arylsulfate"), an aralkyl ("aralkylsulfate") and so on. $C_{1-3}$ sulfates are preferred, such as for example, OS(O)$_2$OMe, OS(O)$_2$OEt and OS(O)$_2$OPr. The term "sulfonate" refers to the group SO$_3$H and includes groups having the hydrogen replaced with, for example a $C_{1-6}$ alkyl group ("alkylsulfonate"), an aryl ("arylsulfonate"), an aralkyl ("aralkylsulfonate") and so on. $C_{1-3}$ sulfonates are preferred, such as for example, SO$_3$Me, SO$_3$Et and SO$_3$Pr.

The term "phosphate" refers to a group —OP(O)(OH)$_2$ and includes groups having each hydrogen independently optionally replaced with, for example a $C_{1-6}$ alkyl group ("alkylphosphate"), an aryl ("arylphosphate"), an aralkyl ("aralkylphosphate") and so on.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$ alkyl, $C_{2-6}$ alkenyl, $C_{2-6}$ alkynyl, $C_{3-8}$ cycloalkyl, hydroxyl, oxo, $C_{1-6}$ alkoxy, aryloxy, $C_{1-6}$ alkoxyaryl, halogen, $C_{1-6}$ alkylhalogen (such as CF$_3$ and CHF$_2$), $C_{1-6}$ alkoxyhalogen (such as OCF$_3$ and OCHF$_2$), carboxyl, alkoxycarbonyl, cyano, nitro, amino, mono substituted amino, disubstituted amino, acyl, amides, aminoacyl, substituted amides, disubstituted amides, carbamic acid, carbamates, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, phosphates, phosphonates, aryl, aryl-$C_{1-6}$alkyl, heterocyclyl, heteroaryl and spiro ring systems wherein each alkyl, alkenyl, alkynyl, cycloalkyl, aryl, heterocyclyl, heteroaryl and spiro ring system and groups containing them may be further optionally substituted. Unless otherwise defined, particularly preferred optional substituents in one case include 1, 2, 3 or 4, preferably 1 or 2 substituents each independently selected from the group consisting of $C_{1-4}$ alkyl (particularly methyl), halogen (particularly F), halogen-$C_{1-3}$ alkyl (particularly CHF$_2$ and CF$_3$), OH, $C_{1-4}$ alkoxyl (particularly OCH$_3$), COOH, COO—$C_{1-4}$ alkyl (particularly COOCH$_3$), NH$_2$, NH—$C_{1-4}$ alkyl (particularly NHCH$_3$), N($C_{1-4}$ alkyl)$_2$ (particularly N(CH$_3$)$_2$), NHC(=O)—$C_{1-4}$ alkyl, NHC(=O)-4-6-membered heterocyclyl, OP(=O)(OR)$_2$ (where each R is independently H or $C_{1-4}$ alkyl), P(=O)(OR)$_2$ (where each R is independently H or $C_{1-4}$ alkyl), $C_{3-6}$ cycloalkyl (particularly cyclopropyl, cyclobutyl, cyclopenyl and cyclohexyl), phenyl, 4-6-membered heterocylyl (particularly oxetanyl, azetidinyl, tetrahydrofuranyl, pyrrolidinyl, tetrahydropyranyl, morpholinyl, thiomorpholinyl, oxothiazinyl, dioxothiazinyl, thianyl (also known as tetrahydrothiopyranyl), oxothianyl, dioxothianyl, piperidinyl, and piperazinyl) and further where $C_{1-4}$alkyl either alone or as part of a substituent group includes methyl, ethyl, n-propyl, isopropyl, n-butyl, iso-butyl, sec-butyl and tert-butyl and may be further optionally substituted.

Optional substituents in the case of heterocycles, heteroaryls and spiro bicyclic heterocyclic ring systems containing N may also include but are not limited to alkyl, e.g. N—$C_{1-3}$ alkyl, more preferably methyl, particularly N-methyl. It will be understood that suitable derivatives of aromatic heterocyclyls containing nitrogen include N-oxides thereof.

Examples of $C_{1-4}$ alkyl include methyl, ethyl, propyl, butyl, tert-butyl and isopropyl; examples of $C_{1-6}$ alkyl include $C_{1-4}$ alkyl, pentyl and hexyl; examples of $C_{2-4}$ alkenyl include vinyl, propenyl, allyl, but-2-enyl and but-3-enyl; examples of $C_{2-6}$ alkenyl include $C_{2-4}$ alkenyl, pent-2-enyl, pent-3-enyl, and hex-5-enyl; examples of $C_{2-4}$ alkynyl include ethynyl, prop-2-ynyl, but-2-ynyl and but-3-ynyl; examples of $C_{2-6}$ alkynyl include $C_{2-4}$ alkynyl, pent-3-ynyl and hex-4-ynyl; examples of $C_{1-6}$ alkoxy and —O—$C_{1-6}$ alkyl include methoxy, ethoxy, propoxy, iso-propoxy, butoxy, tert-butoxy, pentoxy and hexoxy; examples of $C_{1-4}$ alkoxy include methoxy, ethoxy and propoxy; examples of $C_{1-4}$ alkoxy-$C_{1-4}$ alkyl include methoxymethyl, ethoxymethyl, methoxyethyl and propoxy methyl; examples of $C_{3-6}$ cycloalkyl include cyclopropyl, cyclobutyl, cyclopentyl and cyclohexyl; examples of halogen groups include fluoro, chloro and bromo; examples of halogen-$C_{1-4}$ alkyl groups include fluoromethyl, fluoroethyl, chloromethyl, chloroethyl and bromomethyl; examples of hydroxyl-$C_{1-4}$ alkyl and hydroxyl-$C_{1-6}$ alkyl include hydroxymethyl, 1-hydroxyethyl, 2-hydroxyethyl and 3-hydroxypropyl; examples of —CO—$C_{1-4}$ alkyl include methylcarbonyl, ethylcarbonyl, propyl carbonyl, isopropylcarbonyl and tert-butylcarbonyl; examples of —CO—$C_{1-6}$ alkyl include —CO—$C_{1-4}$ alkyl and pentylcarbonyl; examples of —COO—$C_{1-4}$ alkyl include methoxycarbonyl, ethoxycarbonyl, propoxycarbonyl, isopropoxy carbonyl and tert-butoxycarbonyl; examples of —COO—$C_{1-6}$ alkyl include —COO—$C_{1-4}$ alkyl and pentoxycarbonyl; examples of —OCO—$C_{1-4}$ alkyl include methylcarbonyloxy, ethylcarbonyloxy, propylcarbonyloxy, isopropylcarbonyloxy and tert-butylcarbonyloxy; examples of —OCO—$C_{1-6}$ alkyl include —OCO—$C_{1-4}$ alkyl and pentylcarbonyloxy; examples of —$C_{1-4}$ alkyl-COO—$C_{1-4}$ alkyl include methoxycarbonylmethyl, ethoxycarbonylmethyl, methoxycarbonylethyl, propoxycarbonylmethyl, isopropoxycarbonylmethyl and tert-butoxycarbonylmethyl; examples of —C(O)NH—$C_{1-4}$ alkyl include methylaminocarbonyl, ethylaminocarbonyl, propylaminocarbonyl, isopropylaminocarbonyl and tert-butylaminocarbonyl; examples of —C(O)N[$C_{1-4}$ alkyl]$_2$ include N-dimethylaminocarbonyl and N-methyl-N-ethylaminocarbonyl; examples of —S(O)$_2$NH—$C_{1-4}$ alkyl include N-methylaminosulfonyl and N-ethylaminosulfonyl; examples of —S(O)$_2$N[$C_{1-4}$ alkyl]$_2$ include N,N-dimethylaminosulfonyl, N,N-diethylaminosulfonyl and N-methyl-N-ethylaminosulfonyl; examples of —S(O)p-$C_{1-4}$ alkyl include methylthio, methylsulfinyl, methylsulfonyl, ethylthio, propylthio, isopropylthio, ethylsulfinyl and ethylsulfonyl.

Another embodiment of the invention provides a compound selected from the group consisting of any one or more of the compounds described in the Examples section, or a pharmaceutically acceptable salt thereof. Moreover, if such compound is represented as a salt, the present invention is intended to include free bases, free acids, or alternative salts of these particular compounds. Additional embodiments comprise compositions and medicaments containing the same (including aforementioned free bases, free acids, or alternative salts, as well as processes for the preparation and use of such compounds, compositions and medicaments. Moreover, it should be noted that each of these compounds and salts thereof, are also intended to be separate embodiments, and in this regard, each species listed in Examples, and salt thereof, should be considered to be an individual embodiment. Moreover, it should be understood that the present invention is intended to include any novel compound or pharmaceutical composition described herein.

Unless otherwise stated, variables in the embodiments below are defined as for formula (I).

According to certain embodiments, $R^1$ is hydrogen.
According to certain embodiments, $R^1$ is methyl.
According to certain embodiments, $R^1$ is ethyl.
According to certain embodiments, $R^1$ is propyl.
According to certain embodiments, $R^1$ is butyl.
According to certain embodiments, $R^1$ is isopropyl.
According to certain embodiments, $R^1$ is cyclopropyl.
According to certain embodiments, $R^1$ is aminomethyl.
According to certain embodiments, $R^1$ is trifluoromethyl.
According to certain embodiments, $R^1$ is hydroxymethyl.
According to certain embodiments, $R^1$ is amino.
According to certain embodiments, $R^1$ is methylamino.
According to certain embodiments, $R^1$ is ethylamino.
According to certain embodiments, $R^1$ is chloro.
According to certain embodiments, $R^1$ is bromo.
According to certain embodiments, $R^1$ is fluoro.
According to certain embodiments, $R^1$ is iodo.
According to certain embodiments, $R^1$ is cyano.
According to certain embodiments, $R^2$ is hydrogen.
According to certain embodiments, $R^2$ is chloro.
According to certain embodiments, $R^2$ is bromo.
According to certain embodiments, $R^2$ is fluoro.
According to certain embodiments, $R^2$ is iodo.
According to certain embodiments, $R^2$ is cyano.
According to certain embodiments, $R^2$ is trifluoromethyl.
According to certain embodiments, $R^3$ is hydrogen.
According to certain embodiments, $R^3$ is chloro.
According to certain embodiments, $R^3$ is bromo.
According to certain embodiments, $R^3$ is fluoro.
According to certain embodiments, $R^3$ is iodo.
According to certain embodiments, $R^3$ is cyano.
According to certain embodiments, $R^3$ is trifluoromethyl.
According to certain embodiments, $R^4$ is hydrogen.
According to certain embodiments, $R^4$ is represented by formula $(CH_2)_{0-6}$-A and A is hydrogen and may be optionally substituted.
According to certain embodiments, $R^4$ is represented by formula $(CH_2)_{0-6}$-A and A is monocyclic $C_{3-7}$ cycloalkyl and may be optionally substituted.
According to certain embodiments, $R^4$ is represented by formula $(CH_2)_{0-6}$-A and A is monocyclic $C_{3-7}$ cycloalkenyl and may be optionally substituted.
According to certain embodiments, $R^4$ is represented by formula $(CH_2)_{0-6}$-A and A is saturated or unsaturated monocyclic 3-7 membered heterocycle and may be optionally substituted.
According to certain embodiments, $R^4$ is represented by formula $(CH_2)_{0-6}$-A and A is saturated or unsaturated fused bicyclic 8-10 membered-heterocycle and may be optionally substituted.
According to certain embodiments, $R^4$ is represented by formula $(CH_2)_{0-6}$-A and A is $C_{6-10}$ aryl and may be optionally substituted.
According to certain embodiments, $R^4$ is represented by formula $(CH_2)_{0-6}$-A and A is 5-10 membered heteroaryl and may be optionally substituted.
According to certain embodiments, $R^5$ is (hydroxyimino)methyl.
According to certain embodiments, $R^5$ is selected from optionally substituted —CO—$C_{1-6}$ alkyl.
According to certain embodiments, $R^5$ is selected from optionally substituted —CO—$C_{2-6}$ alkenyl.
According to certain embodiments, $R^5$ is selected from optionally substituted —CO—$C_{2-6}$ alkynyl.
According to certain embodiments, $R^5$ is carboxyl.
According to certain embodiments, $R^5$ is selected from optionally substituted —COO—$C_{1-6}$ alkyl.
According to certain embodiments, $R^5$ is selected from optionally substituted —COO—$C_{1-6}$ alkyl (optionally substituted with —COO—$C_{1-6}$ alkyl).
According to certain embodiments, $R^5$ is selected from —CONR$^6$R$^7$.
According to certain embodiments, $R^5$ is selected from —O(CO)NR$^6$R$^7$.
According to certain embodiments, $R^5$ is selected from —CONHCH(CO$_2$R$^7$)R$^6$.
According to certain embodiments, $R^5$ is selected from optionally substituted —(CH$_2$)$_{1-6}$OH.

According to certain embodiments, $R^5$ is selected from optionally substituted heterocyclyl.

According to certain embodiments, $R^5$ is selected from optionally substituted aryl.

According to certain embodiments, $R^5$ is selected from optionally substituted —C(=NOR$^7$)—C$_{1-4}$ alkyl.

According to certain embodiments, $R^5$ is selected from —C(=NOR$^7$)NR$^6$R$^7$ According to certain embodiments, $R^5$ is selected from —S(O)pNR$^6$R$^7$.

According to certain embodiments, $R^5$ is selected from optionally substituted —S(O)p-C$_{1-4}$ alkyl-CONHR$^7$.

According to certain embodiments, $R^5$ is selected from optionally substituted —C(O)NHS(O)p-C$_{1-4}$ alkyl.

According to certain embodiments, $R^5$ is selected from optionally substituted —C(O)NHS(O)p-aryl.

According to certain embodiments, $R^5$ is selected from —CH$_2$CH(COOR$^6$)OH.

According to certain embodiments, $R^5$ is selected from optionally substituted —C$_{1-4}$ alkyl-CH(NR$^6$R$^7$)COOR$^6$.

According to certain embodiments, $R^5$ is selected from optionally substituted —C$_{1-4}$ alkyl-CH(NR$^6$R$^7$)CONR$^6$R$^7$).

According to certain embodiments, $R^6$ is hydrogen.

According to certain embodiments, $R^6$ is selected from optionally substituted C$_{1-6}$ alkyl.

According to certain embodiments, $R^7$ is hydrogen.

According to certain embodiments, $R^7$ is selected from optionally substituted C$_{1-6}$ alkyl.

According to certain embodiments, $R^6$ and $R^7$ may together with the nitrogen to which they are attached form a 5 or 6-membered heterocyclic ring, optionally substituted with 1 or 2 substituents independently selected from C$_{1-4}$ alkyl, C$_{2-4}$ alkenyl, (C$_{2-4}$ alkynyl, hydroxy, C$_{1-4}$ alkoxy, halogen, cyano, nitro, carboxyl, hydroxyl-C$_{1-4}$ alkyl-, C$_{1-4}$ alkoxy-C$_{1-4}$ alkyl-, halogen-C$_{1-4}$ alkyl-, difluoromethyl, trifluoromethyl, formyl, —CO—C$_{1-4}$ alkyl, —COO—C$_{1-4}$ alkyl, —C(O)NH$_2$, —C(O)NH—C$_{1-4}$ alkyl, —C(O)N[C$_{1-4}$ alkyl]$_2$, —SO$_2$NH$_2$, —SO$_2$NH—C$_{1-4}$ alkyl, —SO$_2$[C$_{1-4}$ alkyl]$_2$ and —S(O)p-C$_{1-4}$ alkyl, wherein p is (independently at each occurrence) 0, 1 or 2.

According to certain embodiments, $X^1$ is S.

According to certain embodiments, $X^1$ is O.

According to certain embodiments, $X^1$ is NH.

According to certain embodiments, $X^2$ is N.

According to certain embodiments, $X^2$ is C—R$^8$, wherein $R^3$ is selected from a group consisting of H, hydroxy, halogengen, carboxyl, optionally substituted C$_{1-6}$ alkyl, optionally substituted C$_{2-6}$alkenyl, optionally substituted C$_{2-6}$ alkynyl, optionally substituted (CH$_2$)$_m$O—C$_{1-6}$ alkyl, optionally substituted (CH$_2$)$_m$S—C$_{1-6}$ alkyl, optionally substituted (CH$_2$)$_m$S(=O)—C$_{1-6}$ alkyl, optionally substituted (CH$_2$)$_m$O(CH$_2$)$_m$—C$_{3-7}$ cycloalkyl, optionally substituted (CH$_2$)$_m$—C$_{3-7}$ cycloalkyl, optionally substituted (CH$_2$)$_m$O(CH$_2$)$_m$aryl, optionally substituted (CH$_2$)$_m$O(CH$_2$)$_m$-5-10-membered heterocycleheterocycle, optionally substituted (CH$_2$)$_m$-5-10-membered heterocycleheterocycle, optionally substituted halogen-C$_{1-6}$ alkyl, cyano or optionally substituted (CH$_2$)$_m$NR$^9$R$^{10}$ and where each m is an integer independently selected from 0, 1,2 and 3.

According to certain embodiments, $X^3$ is N.

According to certain embodiments, $X^3$ is C—R$^8$, wherein $R^3$ is selected from a group consisting of H, hydroxy, halogengen, carboxyl, optionally substituted C$_{1-6}$ alkyl, optionally substituted C$_{2-6}$ alkenyl, optionally substituted C$_{2-6}$ alkynyl, optionally substituted (CH$_2$)$_m$O—C$_{1-6}$ alkyl, optionally substituted (CH$_2$)$_m$S—C$_{1-6}$ alkyl, optionally substituted (CH$_2$)$_m$S(=O)—C$_{1-6}$ alkyl, optionally substituted (CH$_2$)$_m$O(CH$_2$)$_m$—C$_{3-7}$ cycloalkyl, optionally substituted (CH$_2$)$_m$—C$_{3-7}$ cycloalkyl, optionally substituted (CH$_2$)$_m$O(CH$_2$)$_m$aryl, optionally substituted (CH$_2$)$_m$O(CH$_2$)$_m$-5-10-membered heterocycleheterocycle, optionally substituted (CH$_2$)$_m$-5-10-membered heterocycleheterocycle, optionally substituted halogen-C$_{1-6}$ alkyl, cyano or optionally substituted (CH$_2$)$_m$NR$^9$R$^{10}$ and where each m is an integer independently selected from 0, 1,2 and 3.

According to certain embodiments, $R^9$ and $R^{10}$ are each independently selected from H or optionally substituted C$_{1-6}$ alkyl, optionally substituted C$_{3-6}$ cycloylkyl and optionally substituted 4-6-membered heterocyclyl or $R^9$ and $R^{10}$ join together to form an optionally substituted 4-6-membered heterocyclyl and where each m is an integer independently selected from 0, 1, 2 and 3.

According to certain embodiments, $X^4$ is N.

According to certain embodiments, $X^4$ is C—R$^8$, wherein $R^3$ is selected from a group consisting of H, hydroxy, halogengen, carboxyl, optionally substituted C$_{1-6}$ alkyl, optionally substituted C$_{2-6}$ alkenyl, optionally substituted C$_{2-6}$ alkynyl, optionally substituted (CH$_2$)$_m$O—C$_{1-6}$ alkyl, optionally substituted (CH$_2$)$_m$S—C$_{1-6}$ alkyl, optionally substituted (CH$_2$)$_m$S(=O)—C$_{1-6}$ alkyl, optionally substituted (CH$_2$)$_m$O(CH$_2$)$_m$—C$_{3-7}$ cycloalkyl, optionally substituted (CH$_2$)$_m$—C$_{3-7}$ cycloalkyl, optionally substituted (CH$_2$)$_m$O(CH$_2$)$_m$aryl, optionally substituted (CH$_2$)$_m$O(CH$_2$)$_m$-5-10-membered heterocycleheterocycle, optionally substituted (CH$_2$)$_m$-5-10-membered heterocycleheterocycle, halogen-(1-3C)alkyl, cyano or optionally substituted (CH$_2$)$_m$NR$^9$R$^{10}$ and where each m is an integer independently selected from 0, 1,2 and 3.

According to certain embodiments, only one of $X^2$, $X^3$ or $X^4$ can be N.

According to certain embodiments, a compound of formula (I) (as described above) is provided, wherein:

$R^1$ is selected from methyl, chloro and bromo;

$R^2$ and $R^3$ are each independently selected from chloro, bromo or fluoro;

$R^4$ is (CH$_2$)$_{0-6}$-A wherein A is H, carboxyl, NR$^6$R$^7$ or is selected from optionally substituted monocyclic C$_{3-7}$ cycloalkyl, optionally substituted monocyclic C$_{3-7}$ cycloalkenyl, optionally substituted saturated or unsaturated monocyclic 3-7 membered heterocycle, optionally substituted saturated or unsaturated fused bicyclic 8-10 membered-heterocycle, optionally substituted C$_{6-10}$ aryl and optionally substituted 5-10 membered heteroaryl;

$R^5$ is (hydroxyimino)methyl, —CO—C$_{1-6}$ alkyl, —CO—C$_{2-6}$ alkenyl, —CO—C$_{2-6}$ alkynyl, carboxyl, —COO—C$_{1-6}$ alkyl, —CONR$^6$R$^7$, —OCONR$^6$R$^7$, —OCO—C$_{1-6}$ alkyl, —COO—C$_{1-6}$ alkyl (optionally substituted with —COO—C$_{1-6}$ alkyl), —CONHCH(CO$_2$R$^7$)R$^6$, —(CH$_2$)$_{0-6}$OH, —O—C$_{1-6}$ alkyl, hydroxyl-C$_{1-6}$ alkyl, heterocyclyl, aryl, —C(=NOR$^7$)C$_{1-6}$ alkyl, —C(=NOR$^7$)NR$^6$R$^7$, —S(O)pNR$^6$R$^7$, —S(O)p-C$_{1-6}$ alkyl-CONHR$^7$, —C(O)NHS(O)p-C$_{1-6}$ alkyl, —C(O)NHS(O)p-aryl, —CH$_2$CH(COOR$^6$)OH, —C$_{1-6}$ alkyl-CH(NR$^6$R$^7$)COOR$^6$ or —C$_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and C$_{1-6}$ alkyl;

or $R^6$ and $R^7$ may together with the nitrogen to which they are attached form a 5 or 6-membered heterocyclic ring, optionally substituted with 1 or 2 substituents independently selected from C$_{1-4}$alkyl, C$_{2-4}$ alkenyl, C$_{2-4}$ alkynyl, hydroxyl, C$_{1-4}$ alkoxy, halogen, cyano, nitro, carboxyl, hydroxy-$C_{1-4}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{14}$ alkyl; p is (independently at each occurrence) 0, 1 or 2;

$X^1$ is S, O or NH;

$X^2$ or $X^3$ is N or C—$R^8$, preferably C—$R^8$;

$R^3$ is selected from a group consisting of H, hydroxy, halogengen, carboxyl, optionally substituted $C_{1-6}$ alkyl, optionally substituted $C_{2-6}$ alkenyl, optionally substituted $C_{2-6}$ alkynyl, optionally substituted $(CH_2)_mO$—$C_{1-6}$ alkyl, optionally substituted $(CH_2)_mS$—$C_{1-6}$alkyl, optionally substituted $(CH_2)_mS(=O)$—$C_{1-6}$alkyl, optionally substituted $(CH_2)_mO(CH_2)_m$—$C_{3-7}$ cycloalkyl, optionally substituted $(CH_2)_m$—$C_{3-7}$ cycloalkyl, optionally substituted $(CH_2)_mO(CH_2)_m$aryl, optionally substituted $(CH_2)_mO(CH_2)_m$-5-10-membered heterocycleheterocycle, optionally substituted $(CH_2)_m$-5-10-membered heterocycleheterocycle, optionally substituted halogen $C_{3-7}$ alkyl, cyano or optionally substituted $(CH_2)_mNR^9R^{10}$ and where each m is an integer independently selected from 0, 1, 2 and 3.

$R^9$ and $R^{10}$ are each independently selected from H or optionally substituted $C_{1-6}$alkyl, optionally substituted $C_{3-6}$cycloylkyl and optionally substituted 4-6-membered heterocyclyl or $R^9$ and $R^{10}$ join together to form an optionally substituted 4-6-membered heterocyclyl and where each m is an integer independently selected from 0, 1, 2 and 3;

$X^1$ is S, O or NH;

$X^2$, $X^3$ and $X^4$ are each independently selected from N and C—$R^8$, preferably with the proviso that only one of $X^2$, $X^3$ or $X^4$ can be N.

According to certain embodiments, a compound of formula (I) (as described above) is provided, wherein:

$R^1$ is selected from methyl and halogen.

$R^2$ and $R^3$ are each independently selected from halogen, preferably from chloro, fluoro or bromo.

$R^4$ is $(CH_2)_{0-6}$-A wherein A is H, carboxyl, $NR^6R^7$ or is selected from optionally substituted monocyclic $C_{3-7}$ cycloalkyl, optionally substituted monocyclic $C_{3-7}$ cycloalkenyl, optionally substituted saturated or unsaturated monocyclic 3-7 membered heterocycle, optionally substituted saturated or unsaturated fused bicyclic 8-10 membered-heterocycle, optionally substituted $C_{6-10}$ aryl and optionally substituted 5-10 membered heteroaryl;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$) $C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S, O or NH;

$X^2$, $X^3$ and $X^4$ are each independently selected from N and CH, preferably with the proviso that only one of $X^2$, $X^3$ or $X^4$ can be N.

According to certain embodiments, a compound of formula (I) (as described above) is provided, wherein:

$R^1$ is selected from methyl and halogen;

$R^2$ and $R^3$ are each independently selected from halogen, preferably from chloro and bromo;

$R^4$ is H;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$) $C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S, O or NH;

$X^2$ is C—$R^8$;

$R^8$ is selected from a group consisting of H, hydroxy, halogengen, carboxyl, optionally substituted $C_{1-6}$ alkyl, optionally substituted $C_{2-6}$ alkenyl, optionally substituted $C_{2-6}$ alkynyl, optionally substituted $(CH_2)_mO$—$C_{1-6}$alkyl, optionally substituted $(CH_2)_mS$—$C_{1-6}$alkyl, optionally substituted $(CH_2)_mS(=O)$—$C_{1-6}$alkyl, optionally substituted $(CH_2)_mO(CH_2)_m$—$C_{3-7}$ cycloalkyl, optionally substituted $(CH_2)_m$—$C_{3-7}$ cycloalkyl, optionally substituted $(CH_2)_mO(CH_2)_m$aryl, optionally substituted $(CH_2)_mO(CH_2)_m$-5-10-membered heterocycleheterocycle, optionally substituted $(CH_2)_m$-5-10-membered heterocycleheterocycle, optionally substituted halogen-$C_{1-6}$ alkyl, cyano or optionally substituted $(CH_2)_mNR^9R^{10}$ and where each m is an integer independently selected from 0, 1,2 and 3.

$R^9$ and $R^{10}$ are each independently selected from H or optionally substituted $C_{1-6}$alkyl, optionally substituted $C_{3-6}$ cycloylkyl and optionally substituted 4-6-membered heterocyclyl or $R^9$ and $R^{10}$ join together to form an optionally substituted 4-6-membered heterocyclyl and where each m is an integer independently selected from 0, 1, 2 and 3; $X^3$ and $X^4$ are each independently selected from N and CH, preferably with the proviso that only one of $X^3$ or $X^4$ can be N.

According to certain embodiments, a compound of formula (I) (as described above) is provided, wherein:

$R^1$ is selected from methyl and halogen.

$R^2$ and $R^3$ are each independently selected from halogen, preferably from chloro and bromo.

$R^4$ is H;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$)$C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S, O or NH;

$X^3$ is C—$R^8$;

$R^8$ is selected from a group consisting of H, hydroxy, halogengen, carboxyl, optionally substituted $C_{1-6}$ alkyl, optionally substituted $C_{2-6}$ alkenyl, optionally substituted $C_{2-6}$ alkynyl, optionally substituted (CH$_2$)$_m$O—$C_{1-6}$alkyl, optionally substituted (CH$_2$)$_m$S—$C_{1-6}$alkyl, optionally substituted (CH$_2$)$_m$S(=O)—$C_{1-6}$alkyl, optionally substituted (CH$_2$)$_m$O(CH$_2$)$_m$—$C_{3-7}$ cycloalkyl, optionally substituted (CH$_2$)$_m$—$C_{3-7}$ cycloalkyl, optionally substituted (CH$_2$)$_m$O(CH$_2$)$_m$aryl, optionally substituted (CH$_2$)$_m$O(CH$_2$)$_m$-5-10-membered heterocycleheterocycle, optionally substituted (CH$_2$)$_m$-5-10-membered heterocycleheterocycle, optionally substituted halogen-$C_{1-6}$ alkyl, cyano or optionally substituted (CH$_2$)$_m$NR$^9$R$^{10}$ and where each m is an integer independently selected from 0, 1,2 and 3.

$X^2$ and $X^4$ are each independently selected from N and CH, preferably with the proviso that only one of $X^2$ and $X^4$ can be N.

According to certain embodiments, a compound of formula (I) (as described above) is provided, wherein:

$R^1$ is selected from methyl and halogen.

$R^2$ and $R^3$ are each independently selected from halogen, preferably from chloro and bromo;

$R^4$ is H;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$)$C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$ alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S, O or NH;

$X^2$, $X^3$ and $X^4$ are each independently selected from N and CH, preferably with the proviso that only one of $X^2$, $X^3$ and $X^4$ can be N.

According to certain embodiments, a compound of formula (I) (as described above) is provided, wherein:

$R^1$ is selected from methyl, chloro and bromo;

$R^2$ and $R^3$ are each independently selected from Cl or Br;

$R^4$ is H;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$)$C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S;

$X^2$, $X^3$ and $X^4$ are each independently selected from N and CH, preferably with the proviso that only one of $X^2$, $X^3$ and $X^4$ can be N.

According to certain embodiments, a compound of formula (I) (as described above) is provided, wherein:

$R^1$ is selected from methyl, chloro and bromo;

$R^2$ and $R^3$ are each independently selected from Cl and Br;

$R^4$ is (CH$_2$)$_{0-6}$-A wherein A selected from optionally substituted monocyclic $C_{3-7}$ cycloalkyl, optionally substituted monocyclic $C_{3-7}$ cycloalkenyl, optionally substituted saturated or unsaturated monocyclic 3-7 membered heterocycle, optionally substituted saturated or unsaturated fused bicyclic 8-10 membered-heterocycle, optionally substituted $C_{6-10}$ aryl and optionally substituted 5-10 membered heteroaryl;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$)$C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S;

$X^2$ is CH;

$X^3$ is CH;

$X^4$ is CH.

According to certain embodiments, a compound of formula (I) (as described above) is provided, wherein:

$R^1$ is selected from methyl, chloro and bromo;

$R^2$ and $R^3$ are each independently selected from Cl and Br;

$R^4$ is H;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$)$C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;

$X^1$ is S;

$X^2$ is CH;

$X^3$ is CH;

$X^4$ is CH.

According to certain embodiment, a compound of formula (I) (as described above) is provided, wherein:

$R^1$ is selected from methyl, chloro and bromo;
$R^2$ and $R^3$ are each independently selected from Cl and Br;
$R^4$ is H;
$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl (optionally substituted with —COO—$C_{1-6}$ alkyl), —CONHCH($CO_2R^7$)$R^6$, —$(CH_2)_{0-6}$OH, —O—$C_{1-6}$ alkyl, hydroxyl-$C_{1-6}$ alkyl, heterocyclyl, aryl, —C(=NOR$^7$)$C_{1-6}$ alkyl, —C(=NOR$^7$)NR$^6$R$^7$, —S(O)pNR$^6$R$^7$, —S(O)p-$C_{1-6}$ alkyl-CONHR$^7$, —C(O)NHS(O)p-$C_{1-6}$ alkyl, —C(O)NHS(O)p-aryl, —$CH_2CH$(COOR$^6$)OH, —$C_{1-6}$ alkyl-CH(NR$^6$R$^7$)COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;
$R^6$ and $R^7$ are independently at each occurrence selected from H and $C_{1-6}$ alkyl;
or $R^6$ and $R^7$ may together with the nitrogen to which they are attached form a 5 or 6-membered heterocyclic ring, optionally substituted with 1 or 2 substituents independently selected from $C_{1-4}$alkyl, $C_{2-4}$ alkenyl, $C_{2-4}$ alkynyl, hydroxyl, $C_{1-4}$ alkoxy, halogen, cyano, nitro, carboxyl, hydroxy-$C_{1-6}$ alkyl-, $C_{1-4}$ alkoxy-$C_{1-4}$ alkyl-, halogen-$C_{1-4}$ alkyl-, difluoromethyl, trifluoromethyl, formyl, —CO—$C_{1-4}$ alkyl, —COO—$C_{1-4}$ alkyl, —C(O)NH$_2$, —C(O)NH—$C_{1-4}$ alkyl, —C(O)N[$C_{1-4}$ alkyl]$_2$, —SO$_2$NH$_2$, —SO$_2$NH—$C_{1-4}$ alkyl, —SO$_2$[$C_{1-4}$ alkyl] and —S(O)p-$C_{1-4}$alkyl; p is (independently at each occurrence) 0, 1 or 2;
$X^1$ is S;
$X^2$ and $X^3$ are each C—R$^8$;
$R^8$ is selected from a group consisting of H, hydroxy, halogengen, carboxyl, optionally substituted $C_{1-6}$ alkyl, optionally substituted $C_{2-6}$ alkenyl, optionally substituted $C_{2-6}$ alkynyl, optionally substituted $(CH_2)_m$O—$C_{1-6}$alkyl, optionally substituted $(CH_2)_m$S—$C_{1-6}$alkyl, optionally substituted $(CH_2)_m$S(=O)—$C_{1-6}$alkyl, optionally substituted $(CH_2)_m$O$(CH_2)_m$—$C_{3-7}$ cycloalkyl, optionally substituted $(CH_2)_m$—$C_{3-7}$ cycloalkyl, optionally substituted $(CH_2)_m$O$(CH_2)_m$aryl, optionally substituted $(CH_2)_m$O$(CH_2)_m$-5-10-membered heterocycleheterocycle, optionally substituted $(CH_2)_m$-5-10-membered heterocycleheterocycle, optionally substituted halogen-$C_{1-6}$ alkyl, cyano or optionally substituted $(CH_2)_m$NR$^9$R$^{10}$ and where each m is an integer independently selected from 0, 1, 2 and 3.
$X^4$ is CH.

According to certain embodiments, a compound of formula (I) (as depicted above) is provided, wherein:
$R^1$ is methyl, bromo or chloro;
$R^2$ and $R^3$ are each independently selected from chloro, fluoro or bromo;
$R^4$ is hydrogen;
$R^5$ is carboxyl;
$X^1$ is S or NH or O;
$X^2$, $X^3$ and $X^4$ are each CH.

According to certain embodiments, a compound of formula (I) (as depicted above) is provided, wherein:
$R^1$ is methyl, bromo or chloro;
$R^2$ and $R^3$ are each independently selected from chloro, fluoro or bromo;
$R^4$ is hydrogen;
$R^5$ is carboxyl;
$X^1$ is sulphur;
$X^2$, $X^3$ and $X^4$ are each CH.

According to certain embodiments, a compound of formula (I) (as depicted above) is provided, wherein:
$R^1$ is methyl;
$R^2$ and $R^3$ are each chloro or fluoro;
$R^4$ is hydrogen;
$R^5$ is carboxyl;
$X^1$ is sulphur;
$X^2$, $X^3$ and $X^4$ are each CH.

According to certain embodiments, a compound of formula (I) (as depicted above) is provided, wherein:
$R^1$ is methyl;
$R^2$ and $R^3$ are each chloro or fluoro;
$R^4$ is hydrogen, —$(CH_2)_{1-6}$-A, wherein A is optionally substituted aryl or optionally substituted heterocyclyl;
$R^5$ is carboxyl;
$X^1$ is sulphur;
$X^2$, $X^3$ and $X^4$ are each CH.

According to certain embodiments, a compound of formula (I) (as depicted above) is provided, wherein:
$R^1$ is methyl;
$R^2$ and $R^3$ are each chloro or fluoro;
$R^4$ is hydrogen;
$R^5$ is carboxyl;
$X^1$ is sulphur;
$X^2$ is C—R$^8$, wherein R$^8$ is —O—$(CH_2)_{0-4}$—CH$_3$, fluoro, hydroxyl, optionally substituted —O—$(CH_2)_{0-4}$ aryl or optionally substituted —O—$(CH_2)_{0-4}$ heterocyclyl;
$X^3$ and $X^4$ are each CH.

A compound of formula (I) may form stable acid or basic salts, and in such cases administration of a compound as a salt may be appropriate, and pharmaceutically acceptable salts may be made by conventional methods such as those described below.

Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, dibenzylamine, morpholine, N-ethylmorpholine, N-methylpiperidine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine (i.e., 2-amino-2-hydroxymethyl-propane-1,3-diol), tris-(2-hydroxyethyl)amine, and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, malonic, salicyclic, ascorbic, benzoic, succinic, suberic, fumaric, mandelic, phthalic, α-glycerophosphoric, benzenesulfonic, p-tolylsulfonic, citric, tartaric, methanesulfonic, and the like. Also included are salts of amino acids such as argininate and the like, and salts of organic acids like glucuronic or galactunoric acids and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DNA gyrase and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which posses properties useful in the inhibition of DNA gyrase, it being well known in the art how to prepare optically-active forms (for example, by resolution of the racemic form by recrystallization techniques, by synthesis from optically-active starting materials, by stereoselective synthesis, by enzymatic resolution, by biotransformation, or by chromatographic separation using a chiral stationary phase).

It is also to be understood that certain compounds of the formula (I) and salts thereof can exist in solvated as well as unsolvated forms such as, for example, hydrated forms. It is to be understood that the invention encompasses all such solvated forms which inhibit DNA gyrase.

In addition to salt forms, the invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. A prodrug may improve the physical properties of the parent drug and/or it may also improve overall drug efficacy, for example through the reduction of toxicity and unwanted effects of a drug by controlling its absorption, blood levels, metabolic distribution and cellular uptake.

As stated before, we have discovered a range of compounds that are good inhibitors of DNA gyrase. They have good physical and/or pharmacokinetic properties in general. The following compounds possess preferred pharmaceutical and/or physical and/or pharmacokinetic properties.

Process

In a further aspect the present invention provides a process of preparing a compound of formula (I) or a pharmaceutically-acceptable salt thereof.

If not commercially available, the necessary starting materials for the procedures such as those described below may be made by procedures which are selected from standard organic chemistry techniques, techniques which are analogous to the synthesis of known structurally similar compounds, or techniques, which are analogous to the procedures described in the examples.

It will also be appreciated that in some of the reactions mentioned herein it may be necessary/desirable to protect any sensitive groups in compounds. The instances where protection is necessary or desirable are known to those skilled in the art, as are suitable methods for such protection.

Example of a suitable protecting group for a hydroxy group is, for example, an acyl group, for example an alkanol group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanol or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris (trifluoroacetate). A suitable alternative protecting group for a primary amino group is, for example, a phthalogenyl group which may be removed by treatment with an alkylamine, for example dimethylaminopropylamine or 2-hydroxyethylamine, or with hydrazine.

The protecting groups may be removed at any convenient stage in the synthesis using conventional techniques well known in the chemical art, or they may be removed during a later reaction step or work-up.

Thus, the present invention also provides that the compounds of the formula (I) and pharmaceutically-acceptable salts thereof can be prepared by a process comprising (wherein the variables are as defined above unless otherwise stated):

Process step a) reacting a compound of formula (II)

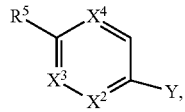

wherein Y is selected from nitro or amino or protected amino group, to a compound of formula (III)

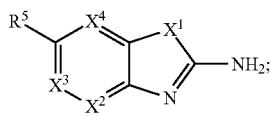

or

Process step b) coupling a compound of formula (III):

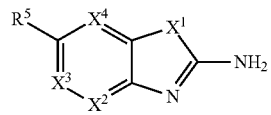

with a compound of formula (IV):

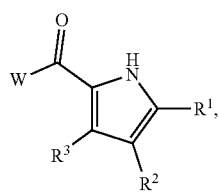

wherein W is selected from hydroxyl, halogen (preferably Cl, Br or I) and 1,1,1-trichloromethyl, to a compound of formula (I):

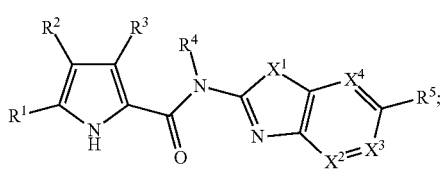

or

Process step c) for compounds of formula (Ia); reacting a compound of formula (I), wherein $R^6$ is —COO—$C_{1-6}$ alkyl (compound of formula (Ia)):

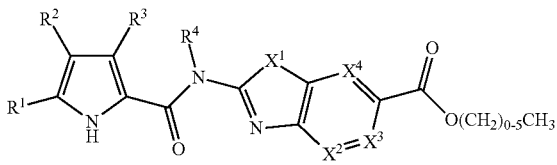

to a compound of formula (V).

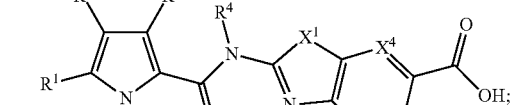

or

Process step d) reacting a compound of formula (V) with a compound of formula (VI):

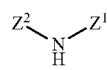

to a compound of formula (VII):

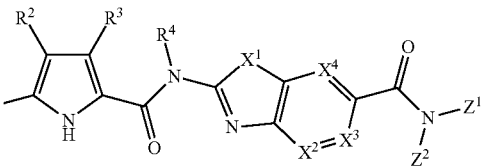

wherein $Z^1$ and $Z^2$ are independently selected from H, —$R^6R^7$, —$CH(CO_2R^7)R^6$, heterocyclyl, aryl.

Description of the Target Species of the Present Invention

The invention herein provides a method or ingredient for treatment or the prevention of bacterial infection in a human or animal comprising administering the human or animal a therapeutically effective amount of a compound of formula (I) of the present invention, and more specifically any one of Examples 1-45 disclosed below.

Specifically, the bacterium is a Gram-negative, a Gram-positive, or a Gram-variable bacterium.

Specifically, the bacterium is a pathogenic bacterium, an opportunistic bacterial pathogen, or other bacterium.

The bacteria in accordance to the present invention may be one selected from the group consisting of, but not limited to, the Proteobacteria phylum, including the family of Pseudomonodaceae, including the *Pseudomonas* genus and the unclassified Pseudomonads, the family of Moraxellaceae, including the *Acinetobacter* genus, the Gammaproteobacteria class, including the Enterobacteriaceae family, including *Citrobacter, Edwardsiella, Enterobacillus,*

*Enterobacter, Cronobacter, Erwinia, Hafnia, Escherichia, Klebsiella, Pantoea, Proteus, Salmonella, Serratia, Shigella, Yersinia* genus and species, Alphaproteobacteria class, including Magnetococcidae, Rickettsidae, Caulobacteridae with Rhizobiales, the Betaproteobacteria class, including Burkholderiale, Neisseriales, including the Neisseriaceae family, *Vibrio*, including *Vibrio cholera*, the Epsilonproteobacteria class, including the *Campylobacter* and *Helicobacter* genus, the Spirochaetes phylum, the Firmicutes phylum, including Clostridia and Bacilli, the Fusobacteria phylum, the Tenericutes phylum, including the *Mycoplasma, Spiroplasma*, and *Ureaplasma* genera, the Actinobacteria phylum, including Mycobacteriaceae and the *Mycobacterium* genus, Pasteurellaceae family, including the *Haemophilus* and *Pasteurella* genus, Legionellaceae family, including *Legionella*, the Bacteroidetes phylum, including the family of Bacteroidetes and Porphyromonadaceae, or any of their drug-resistant, synthetic or engineered variants.

Specifically, the bacterium is a pathogen (disease-causing), e.g. a human, animal or plant pathogen.

Specifically, the pathogen is selected from the group consisting of *Clostridium* species, including *Clostridium difficile, Clostridium perfringens* and *Clostridium tetani, Bacillus* species, including *Bacillus anthracis, Haemophilus* species including *Haemophilus influenzae, Helicobacter* species, including *Helicobacter pylori, Bacteroides* species, including *Bacteroides fragilis, Bordetella pertussis, Borrelia* species, including *Borrelia burgdorferi, Borrelia garinii, Borrelia afzelii, Brucella* species, including *Brucella abortus, Brucella canis, Brucella melitensis, Brucella suis, Chlamydia* species, *Coxiella* species, *Legionella* species, including *Legionella pneumophila, Corynebacterium diphtheriae, Ehrlichia* species, including *Ehrlichia canis, Ehrlichia chaffeensis, Leptospira* species, *Treponema* species, including *Treponema pallidum, Neisseria* species, including *Neisseria gonorrhoeae* and including drug-resistant *Neisseria gonorrhoeae, Listeria* species including *Listeria monocytogenes*, the Enterobacteriaceae family, including Carbapenem-resistant Enterobacteriaceae (CRE), extended spectrum β-lactamase producing Enterobacteriaceae (ESBLs), *Enterobacter* species, including *Enterobacter cloacae, Enterobacter aerogenes, Proteus* species, *Providencia* species, *Salmonella* including drug-resistant Non-typhoidal *Salmonella* and *Salmonella Typhi, Shigella*, including drug-resistant *Shigella, Citrobacter* species, *Escherichia* species, including drug- and multidrug resistant *Escherichia coli*, including Enterotoxigenic *E. coli* (ETEC), Enteropathogenic *E. coli* (EPEC), uropathogenic *E. coli* (UPEC), Enteroinvasive *E. coli* (EIEC), Enterohemorrhagic *E. coli* (EHEC), *Acinetobacter* species, including *Acinetobacter baumannii*, drug- and multidrug-resistant *Acinetobacter, Campylobacter*, including drug-resistant *Campylobacter, Enterococcus* species, including Vancomycin-resistant *Enterococcus* (VRE), *Enterococcus faecium, Enterococcus faecalis, Enterococcus gallinarum, Pseudomonas* species, including *Pseudomonas aeruginosa*, including drug- and multidrug-resistant *Pseudomonas aeruginosa, Staphylococcus aureus*, including methicillin-resistant *Staphylococcus aureus* (MRSA) and Vancomycin-resistant *Staphylococcus aureus* (VRSA), *Staphylococcus epidermidis* and methicillin-resistant *Staphylococcus epidermidis* (MRSE), *Staphylococcus haemolyticus, Staphylococcus saprophyticus, Streptococcus intermedius, Streptococcus* species and their drug-resistant variants, including *Streptococcus agalactiae, Streptococcus bovis, Streptococcus constellatus, Streptococcus mitis, Streptococcus mutans, Streptococcus pyogenes, Streptococcus oralis, Streptococcus sanguis, Streptococcus pneumoniae* and including any of their drug-resistant variants, *Stenotrophomonas maltophilia, Pasteurella multocida, Burkholderia* species and their drug-resistant variants, including *Burkholderia cepacia, Burkholderia mallei, Burkholderia pseudomalilei, Burkholderia thailandensis, Propionibacterium* species including *Propionibacterium acnes, Yersinia* species, including *Yersinia pestis, Mycobacterium tuberculosis*, including drug-resistant and extremely-drug-resistant *Mycobacterium tuberculosis, Mycobacterium leprae, Mycoplasma* species including *Mycoplasma pneumoniae, Nocardia asteroids, Vibrio* species or any of the ESKAPE pathogens, including *Enterococcus faecium, Staphylococcus aureus, Klebsiella pneumoniae, Acinetobacter baumannii, Pseudomonas aeruginosa, Enterobacter* species or any of their drug-resistant variants.

Specifically, the drug is an antibacterial agent, which is a chemotherapeutic agent that has the capacity to inhibit the growth of or to kill, one or more microorganism. Antibiotics are well-known to those skilled in the art. Classes of antibiotics include, but are not limited to, aminoglycosides (e.g., amikacin, gentamicin, kanamycin, neomycin, netilmicin, streptomycin, tobramycin, paromomycin and the like), ansamycins (e.g., geldanamycin, herbimycin and the like), carbacephem (e.g., loracarbef), carbapenems (e.g., ertapenem, doripenem, imipenem/cilastatin, meropenem and the like) cephalogensporins (e.g., first generation (e.g., cefadroxil, cefazolin, cefalotin, cefalexin and the like), second generation (e.g., cefaclor, cefamandole, cefoxitin, cefprozil, cefuroxime and the like), third generation (e.g., cefixime, cefdinir, cefditoren, cefoperazone, cefotaxime, cefpodoxime, ceftazidime, ceftibuten, ceftizoxime, ceftriaxone and the like), fourth generation (e.g., cefepime and the like) and fifth generation (e.g., ceftobiprole and the like)), glycopeptides (e.g., teicoplanin, vancomycin and the like), macrolides (e.g., azithromycin, clarithromycin, dirithromycin, erythromycin, roxithromycin, troleandomycin, telithromycin, spectinomycin and the like), monobatams (e.g., aztreonam and the like), penicillins (e.g., amoxicillin, ampicillin, azlocillin, carbenicillin, cloxacillin, dicloxacillin, flucloxacillin, mezlocillin, methicillin, nafcillin, oxacillin, penicillin, piperacillin, ticacillin and the like), polypeptides (e.g., bacitracin, colistin, nisin, polymyxin B, PGLA, TPII and the like) quinolones (e.g., ciprofloxacin, enoxacin, gatifloxacin, delafloxacin, levofloxacin, lomefloxacin, moxifloxacin, norfloxacin, ofloxacin, trovafloxacin and the like), sulfonamides (e.g., mafenide, prontosil, sulfacetamide, sulfamethizole, sulfanilamide, sulfasalazine, sulfisoxazole, trimethoprim, trimethoprim-sulfamethoxazole and the like), tetracyclines (e.g., demeclocycline, doxycycline, minocycline, oxytetracycline, tetracycline and the like) and others (e.g., arsphenamine, chloramphenicol, clindamycin, lincomycin, ethambutol, fosfomycin, fusidic acid, furazolidone, novobiocin, isoniazid, linezolid, metronidazole, mupirocin, nitrofurantoin, platensimycin, pyrazinamide, quinupristin, dalfopristin, rifampin, tinidazol and the like) (See e.g., Robert Berkow (ed.) The Merck Manual of Medical Information—Home Edition. Pocket (September 1999), ISBN 0-671-02727-1). Other antibiotics will be readily apparent to those skilled in the art.

Biological Data

Enzyme Inhibition Assays

Inhibitory activities for compounds of the present invention were determined on *E. coli* and *S. aureus* DNA gyrase and topoisomerase IV in an assay from Inspiralis on streptavidin-coated 96-well microtiter plates from Thermo scientific Pierce. First, the plates were rehydrated with buffer (20 mM Tris-HCl with pH 7.6, 0.01% w/v BSA, 0.05% v/v Tween 20, 137 mM NaCl) and the biotinylated oligonucleotide was then immobilized. After washing off the unbound oligonucleotide, the enzyme test was performed. The reaction volume of 30 μL in buffer (35 mM Tris×HCl with pH 7.5, 4 mM $MgCl_2$, 24 mM KCl, 2 mM DTT, 1.8 mM spermidine, 1 mM ATP, 6.5% w/v glycerol, 0.1 mg/mL albumin for DNA gyrase assays or 40 mM HEPES KOH with pH 7.6, 100 mM potassium glutamate, 10 mM magnesium acetate, 10 mM DTT, 1 mM ATP, 0.05 mg/mL albumin for topoisomerase IV assays) contained 1.5 U of DNA gyrase or topoisomerase IV from *E. coli* or *S. aureus*, 0.75 μg of relaxed pNO1 plasmid, and 3 μL solution of the inhibitor in 10% DMSO and 0.008% Tween 20. Reaction solutions were incubated at 37° C. for 30 min. After that, the TF buffer (50 mM NaOAc with pH 5.0, 50 mM NaCl and 50 mM $MgCl_2$) was added to terminate the enzymatic reaction. After additional incubation for 30 min at rt, during which biotin-oligonucleotide-plasmid triplex was formed, the unbound plasmid was washed off using TF buffer and SybrGOLD in T10 buffer (10 mM Tris HCl with pH 8.0 and 1 mM EDTA) was added. The fluorescence was measured with a microplate reader (BioTek Synergy H4, excitation: 485 nm, emission: 535 nm). Initial screening was done at 100 or 10 nM concentration of inhibitors against *E. coli* DNA gyrase or 1 μM or 100 nM concentration against *S. aureus* DNA gyrase and *E. coli* and *S. aureus* topo IV. For the most active inhibitors $IC_{50}$ was determined using seven concentrations of tested compounds. GraphPad Prism 6.0 software was used to calculate the $IC_{50}$ values. The result is given as the average value of three independent measurements. As the positive control novobiocin ($IC_{50}$=0.168 μM and 0.041 μM (lit. 0.08 μM and 0.01 μM (Alt S. et. al. *J. Antimicrob. Chemoth.* 66, 2061-2096 (2011))) for *E. coli* and *S. aureus* gyrase and $IC_{50}$=11.1 μM and 26.7 μM (lit. 10 μM and 20 μM (Alt S. et. al. *J. Antimicrob. Chemoth.* 66, 2061-2096 (2011))) for *E. coli* and *S. aureus* topoisomerase IV) was used.

Inhibitory activities of compounds described in examples 1-45 of the present invention against DNA gyrase from *E. coli* (Table 1).

TABLE 1

$IC_{50}$ values of example compounds 1-45.

| Example No. | $IC_{50}$ [nM] *E. coli* DNA gyrase |
|---|---|
| Example 1 | 10 ± 1 |
| Example 2 | 12 ± 7 |
| Example 3 | 19 ± 1 |
| Example 4 | 830 ± 150 |
| Example 5 | <5 |
| Example 6 | 46 ± 33 |
| Example 7 | <5 |
| Example 8 | 7.6 ± 3.4 |
| Example 9 | <5 |
| Example 10 | <5 |
| Example 11 | <5 |
| Example 12 | <5 |
| Example 13 | <5 |
| Example 14 | 310 ± 30 |
| Example 15 | 5.1 ± 1.3 |
| Example 16 | <5 |
| Example 17 | <5 |
| Example 18 | 11 ± 2 |
| Example 19 | 89 ± 20 |
| Example 20 | 280 ± 10 |
| Example 21 | 12 ± 5 |
| Example 22 | 7.0 ± 0.9 |
| Example 23 | 7.1 ± 3.2 |
| Example 24 | <5 |
| Example 25 | <5 |
| Example 26 | 16 ± 4 |
| Example 27 | 5.4 ± 2.0 |
| Example 28 | 11 ± 2 |
| Example 29 | <5 |
| Example 30 | <5 |
| Example 31 | <5 |
| Example 32 | <5 |
| Example 33 | >10000 |
| Example 34 | 48 ± 9 |
| Example 35 | <5 |
| Example 36 | <5 |
| Example 37 | <5 |
| Example 38 | 12 ± 5 |
| Example 39 | 1400 ± 20 |
| Example 40 | 1700 ± 360 |
| Example 41 | 320 ± 70 |
| Example 42 | 24 ± 1 |
| Example 43 | 7.2 ± 2.0 |
| Example 44 | <5 |
| Example 45 | <5 |

The compounds of Examples generally had an $IC_{50}$ of less than 10 μM for DNA gyrase from *S. aureus* and for DNA topoisomerase IV from *E. coli* or *S. aureus*. The compounds of Examples 9, 10, 12, 23, 24, 30, 31, 32, 37 and 44 had an $IC_{50}$ of less than 0.02 μM for DNA gyrase from *S. aureus* and less than 0.4 μM for DNA topoisomerase IV from *E. coli* or *S. aureus*.

Antimicrobial Activity Results

The chemical entities described in the present invention were assessed for their antimicrobial activity using a microbroth dilution assay as recommended by the CLSI (Methods for Dilution Antimicrobial Susceptibility Tests for Bacteria That Grow Aerobically, and Methods for Antimicrobial Susceptibility Testing of Anaerobic Bacteria, Clinical and Laboratory Standards Institute, Document M07-A8, and M11-A8, Wayne, PA 19087, USA, 2012.). Compounds were dissolved by using 100% DMSO. Serial two-fold dilutions of each compound were made by using 100% DMSO as the diluent.

A library of Gram-negative and Gram-positive microbes and their drug- and multidrug-resistant variants were employed as test organisms. The MIC (minimum inhibitory concentration) was determined as the lowest concentration of an individual drug that lead to no visible growth.

The compounds of the invention have showed activity against a number of different bacterial pathogens and opportunistic bacterial pathogens (Table 2).

TABLE 2

MIC values of example compounds against *Staphylococcus aureus*, *Enterococcus faecium*, *Enterococcus faecalis* and *Escherichia coli*.

| Example No. | MIC (μg/mL) *S. aureus* ATCC 29213 | MIC (μg/mL) *E. faecium* ATCC 35667 | MIC (μg/mL) *E. faecalis* ATCC 29212 | MIC (μg/mL) *E. coli* ATCC 25922 |
|---|---|---|---|---|
| Example 1 | 0.5 | 0.58 | 0.125 | 4 |
| Example 2 | >64 | 5.56 | 2.78 | >64 |
| Example 3 | >64 | 17.8 | 8.90 | >64 |
| Example 4 | >64 | >64 | >64 | >64 |
| Example 5 | 1.0 | 0.61 | 0.0625 | 16 |
| Example 6 | >64 | >64 | 32 | >64 |
| Example 7 | 16 | 1.21 | 2 | >64 |
| Example 8 | 2.0 | 1.25 | 0.25 | 64 |

TABLE 2-continued

MIC values of example compounds against *Staphylococcus aureus*, *Enterococcus faecium*, *Enterococcus faecalis* and *Escherichia coli*.

| Example No. | MIC (μg/mL) S. aureus ATCC 29213 | MIC (μg/mL) E. faecium ATCC 35667 | MIC (μg/mL) E. faecalis ATCC 29212 | MIC (μg/mL) E. coli ATCC 25922 |
|---|---|---|---|---|
| Example 9 | 0.25 | 0.09 | ≤0.03125 | 32 |
| Example 10 | >64 | 40.2 | 8 | >64 |
| Example 11 | >64 | >64 | >64 | >64 |
| Example 12 | >64 | >64 | >64 | >64 |
| Example 13 | 16 | 1.21 | 1 | >64 |
| Example 14 | >64 | >64 | >64 | >64 |
| Example 15 | 0.42 | 0.83 | 0.21 | >64 |
| Example 16 | ≤0.03125 | 0.36 | ≤0.03125 | 64 |
| Example 17 | 16 | 1.23 | 1 | >64 |
| Example 18 | 1.16 | >64 | >64 | >64 |
| Example 19 | >64 | >64 | 64 | >64 |
| Example 20 | 64 | 38.52 | 0.5 | >64 |
| Example 21 | >64 | >64 | >64 | >64 |
| Example 22 | 32 | 5.52 | 2 | >64 |
| Example 23 | 64 | ND | 16 | >64 |
| Example 24 | >64 | ND | 1.5 | >64 |
| Example 25 | >64 | ND | >64 | >64 |
| Example 26 | >64 | ND | >64 | >64 |
| Example 27 | 4 | ND | 16 | >64 |
| Example 28 | >64 | ND | >64 | >64 |
| Example 29 | 4 | ND | 0.125 | >64 |
| Example 30 | 0.0625 | ND | 0.001 | >64 |
| Example 31 | 0.25 | ND | 0.0156 | 4 |
| Example 32 | 0.065 | ND | 0.01625 | 8 |
| Example 33 | ≥32 | ND | ≥32 | ≥32 |
| Example 34 | ≥32 | ND | ≥32 | ≥32 |
| Example 35 | 0.25 | ND | 0.03125 | ≥32 |
| Example 36 | 4 | ND | 0.5 | ≥32 |
| Example 37 | 0.25 | ND | 0.125 | 16 |
| Example 38 | >64 | ND | >64 | >64 |
| Example 39 | >64 | >64 | ND | >64 |
| Example 40 | >64 | >64 | ND | >64 |
| Example 41 | 32 | ND | 32 | ≥32 |
| Example 42 | 2 | ND | 0.25 | >64 |
| Example 43 | 0.13 | ND | 0.13 | 32 |
| Example 44 | 0.03125 | ND | 0.023 | >64 |
| Example 45 | 0.13 | ND | 0.0625 | >64 |

ND—not determined

Table 3 shows the activities of the compounds of Examples 1 and 9 against a set of Gram-positive and Gram-negative bacterial strains. Compound of Examples 1 and 9 showed potent activity against Gram-positive and Gram-negative bacteria, including multidrug-resistant and MRSA strains and the ESKAPE pathogens (Table 3).

TABLE 3

Extended MIC values of compounds of Example 1 and Example 9 against extended panel of bacterial strains.

| Bacterial species | Strain ID | MIC (μg/mL) Example 1 | MIC (μg/mL) Example 9 |
|---|---|---|---|
| Streptococcus pneumoniae | ATCC 49619 | 0.25 | 0.25 |
| Enterococcus faecium | ATCC 700221 | 0.05 | 0.05 |
| Klebsiella pneumoniae | ATCC 10031 | 11 | 4 |
| Haemophilus influenzae | ATCC 49247 | ≤0.03125 | 0.125 |
| Neisseria gonorrhoeae | ATCC 700825 | ≤0.03125 | ≤0.03125 |
| Helicobacter pylori | ATCC 43504 | 4 | 4 |
| Clostridium difficile, toxigenic, ribotype 078 | BAA-1875 | ≤0.03125 | ≤0.03125 |
| Pseudomonas aeruginosa | ATCC 27863 | 5 | 5 |
| Staphylococcus aureus, MRSA | ATCC 43300 | 0.2 | 0.4 |

Additionally, the compound of Example 1 of the present invention has shown no change in activity against *Escherichia coli* strains that are carrying plasmid-encoded fluoroquinolone resistance genes that are widespread in the clinics (Table 4).

TABLE 4

Activities against *Escherichia coli* strains that are carrying plasmid-encoded fluoroquinolone resistance genes that are widespread in the clinics.

| Strain + antibiotic resistance gene | MIC (μg/mL) Example 1 |
|---|---|
| Escherichia coli ATCC 25922 + qnrA1 | 3.3 |
| Escherichia coli ATCC 25922 + qepA2 | 3.3 |
| Escherichia coli ATCC 25922 + qnrB1 | 3.3 |
| Escherichia coli ATCC 25922 + qnrC | 3.3 |
| Escherichia coli ATCC 25922 + qnrD1 | 2.9 |
| Escherichia coli ATCC 25922 + qnrS1 | 2.9 |
| Escherichia coli ATCC 25922 + aac-(6')-Ib-cr | 3.3 |
| Escherichia coli ATCC 25922 wild-type | 2.9 |

Furthermore, the compound of Example 1 and Example 9 showed increased bioactivity (i.e., decreased MIC) at decreased pH that is similar to the pH of the human skin (i.e., pH 5.5) compared to their bioactivity that is obtainable at pH 7.3 (Table 5). To measure antibacterial activity of the compounds at pH that is similar to the human skin, compounds were assayed for their antimicrobial activity using a modified microbroth dilution assay. This antibacterial activity assay was performed as recommended by the CLSI (Methods for Dilution Antimicrobial Susceptibility Tests for Bacteria That Grow Aerobically, and Methods for Antimicrobial Susceptibility Testing of Anaerobic Bacteria, Clinical and Laboratory Standards Institute, Document M07-A8, and M11-A8, Wayne, PA 19087, USA, 2012) and the pH of the growth medium was set to pH 5.5 by the careful addition of 0.1 M HCl solution. Compounds were dissolved by using 100% DMSO. Vancomycin as included as a comparator antibiotic.

TABLE 5

Activities of Example 1 and 9 against *Staphylococcus aureus* strains at pH which is close to the pH of the skin.

| Bacterial strain | pH | MIC (ng/mL) Example 1 | MIC (ng/mL) Example 9 | MIC (ng/mL) Vancomycin |
|---|---|---|---|---|
| S. aureus ATCC 43300 MRSA | 5.5 | 4 | 8 | 2000 |
|  | 7.3 | 100 | 200 | 1000 |
| S. aureus ATCC 700699 VISA | 5.5 | 0.25 | 0.5 | 8000 |
|  | 7.3 | 40 | 20 | 8000 |

In Vivo Activity Against Multidrug-Resistant Skin Infection in an Animal Model

In vivo activity of the compound of Example 1 was determined against the USA300 mupirocin-resistant, methicillin-resistant *Staphylococcus aureus* (MRSA) (ATCC BAA-1556 strain) in a dermal infection animal model with immune competent ICR mice (based on Kugelberg E, Norström T, Petersen T K, Duvold T, Andersson D I, Hughes D. *Establishment of a superficial skin infection model in mice by using Staphylococcus aureus and Streptococcus pyogenes*. Antimicrob. Agents Chemother. 49: 3435-41, 2005). To establish bacterial infection, wounds were generated by abrasion of the skin's surface and then were inoculated with $9.38 \times 10^4$ CFU/mouse of USA300 MRSA (ATCC BAA-1556) bacterial cells. The human isolate *Staphylococcus* aureus USA300 MRSA (ATCC BAA-1556) was obtained from the American Type Culture Collection (Rockville, MD, USA).

Formulation of the Compound of Example 1

Two 40 mg/mL dose solutions of the compound of Example 1 in 10% DMSO/90% corn oil were prepared by adding 8.9 mg and 8.03 mg compound to 22.3 µL and 20.1 µL of 100% DMSO, respectively. These mixtures were then combined with 200.7 µL and 180.9 µL of corn oil, respectively. Next, the two 40 mg/mL dosing solutions were diluted in 10% DMSO/90% corn oil to generate dosing solutions with two lower concentrations of 20 and 5 mg/mL for animal administrations.

In Vivo Animal Study with Topical Dosing

The compound of Example 1 at 0.5% (5 mg/mL), 2% (20 mg/mL), and 4% (40 mg/mL) was administered topically (20 µL/mouse) twice daily (BID) at 1 and 7 hours after infection. Similarly, the reference standard comparator antibiotic, 2% fusidic acid cream, was administered topically (20 µL/mouse) twice daily at 1 and 7 hr after infection. One "no treatment group" was sacrificed at 1 hr after infection for the initial bacterial counts. Five female ICR mice weighing 24±4 g were applied in each test group. Mice from the test article and vehicle control groups were sacrificed at 25 hr after infection. Animals were sacrificed with $CO_2$ asphyxiation and the infected skin, a 2 $cm^2$ area, was then excised. Following the excision of skin samples, samples were homogenized in 1 mL PBS (pH 7.4) with a Polytron homogenizer. A 0.1 mL aliquot of each homogenate was used for serial 10-fold dilutions and plated onto Nutrient Agar plates for bacterial enumeration (determined as CFU/Skin). Finally, one-way ANOVA followed by Dunnett's comparison test was performed to assess statistical significance ($p<0.05$) in the bacterial counts of the treated animals compared to the vehicle control group.

All aspects of this work, including housing, experimentation, and disposal of animals were performed in general accordance with the Guide for the Care and Use of Laboratory Animals (National Academy Press, Washington, D.C., 2011). The study was performed in an AAALAC accredited ABSL2 laboratory under the supervision of the veterinarians, and the animal care and use protocol were approved by the IACUC.

Results

The topical administrations of the compound of Example 1, at 0.5% (5 mg/mL), 2% (20 mg/mL), and 4% (40 mg/mL) resulted in significant reductions in bacteria counts (99%, 100%, and 100% reductions, respectively; all $p<0.05$) relative to the vehicle control group. A one-$log_{10}$ reduction in counts relative to the initial counts was observed in the dosing groups of the compound of Example 1 at 0.5% (5 mg/mL), 2% (20 mg/mL), and 4% (40 mg/mL) (The FIGURE). As expected (based on Kugelberg E, Norström T, Petersen T K, Duvold T, Andersson D I, Hughes D. *Establishment of a superficial skin infection model in mice by using Staphylococcus aureus and Streptococcus pyogenes*. Antimicrob. Agents Chemother. 49: 3435-41, 2005.), a significant antimicrobial activity ($p<0.05$) and a one-log killing effect were also observed with the topical administration of 2% fusidic acid cream (The FIGURE).

EXAMPLES

The invention is illustrated but not limited by the following Examples in which unless otherwise stated:

(i) evaporation were carried out by rotary evaporation in vacuo and work-up procedures were carried out after removal of residual solids after filtration;
(ii) operations were generally carried out at ambient temperature, that is typically between 18 and 26° C. and without exclusion of air unless otherwise stated, or unless skilled person would otherwise work under an inert atmosphere;
(iii) flash column chromatography was used to purify compounds and was performed on Merck Silica Gel 60 unless otherwise stated;
(iv) yields are given for illustration only and are not necessarily the maximum attainable;
(v) the structure of the end-products was generally confirmed by NMR and mass spectral techniques; proton NMR spectra is quoted and was determined using a Bruker Avance III 400 MHz spectrometer operating at field strength of 400 MHz. Chemical shifts are reported in part per million downfield from tetramethylsilane as an internal standard (δ scale) and peak multiplicities are shown thus: s, singlet; d, doublet; dd, doublet of doublets; dt, doublet of triplets; t, triplet; m, multiplet; br, broad;
(vi) mass spectra were obtained using a Q TOF Premier mass spectrometer (Micromass, Waters, Manchester, UK) and Exactive Plus Orbitrap mass spectrometer (Thermo Fisher Scientific, Waltham, Massachusetts, ZDA);
(vii) analytical reversed-phase HPLC were performed on Thermo Scientific Dionex Ultimate 3000 Binary Rapid Separation LC System. Method A: The column used was Agilent Extend-C18 column (3.5 µm, 4.6×150 mm), a flow rate of 1.0 mL/min and sample injection volume of 10 µL. Mobile phase consisted of acetonitrile as solvent A and 0.1% trifluoroacetic acid (TFA) in ultrapure water as solvent B. The gradient (for solvent A) was: 0-16 min, 30-90%; 16-20 min, 90%; 20-21 min, 90-30%. Method B: The column used was Waters Acquity UPLC CSH C18 column (1.7 µm, 2.1×50 mm), a flow rate of 0.4 mL/min and sample injection volume of 1-4 µL. Mobile phase consisted of acetonitrile as solvent A and 0.1% trifluoroacetic acid (TFA) in ultrapure water as solvent B. The gradient (for solvent A) was: 0-8 min, 30-90%; 8-10 min, 90%; 10-11 min, 90-30%;
(viii) each intermediate was generally purified to the standard required for the subsequent stage and was characterised in sufficient detail to confirm that the assigned structure was correct; purity was assessed by high pressure liquid chromatography, thin layer chromatography, or NMR and identity was determined by mass spectrometry and NMR spectroscopy as appropriate.

(Example 1) Synthesis of 2-(3,4-dichloro-5-methyl-1H-pyrrole-2-carboxamido)benzo[d]thiazole-6-carboxylic acid

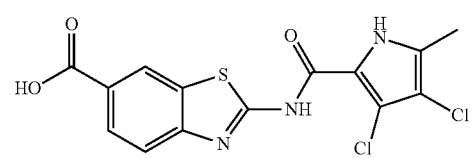 [SMILES: Cc1[nH]c(C(=O)Nc2nc3ccc(C(=O)O)cc3s2)c(Cl)c1Cl]

Exemplified Compound No. 1

Step 1: Synthesis of methyl 2-(3,4-dichloro-5-methyl-1H-pyrrole-2-carboxamido)benzo[d]thiazole-6-carboxylate To a suspension of 3,4-dichloro-5-methyl-1H-pyrrole-2-carboxylic acid (244 mg, 1.26 mmol) in anhydrous dichloromethane (15 mL) oxalyl chloride (0.539 mL, 6.29 mmol) was added dropwise and the solution stirred at room temperature under argon atmosphere overnight. The solvent was evaporated under reduced pressure, methyl 2-aminobenzo[d]thiazole-6-carboxylate (262 mg, 1.26 mmol) and toluene (20 mL) were added and the suspension was stirred at 130° C. overnight. The precipitate in the reaction mixture was filtered off, suspended in 1 M HCl (100 mL), sonicated and filtered off. The crude product was dispersed in methanol (100 mL), heated, filtered off and dried.

Yield: 373 mg (77.2%); grey solid.

$^1$H NMR (400 MHz, DMSO-$d_6$) δ 2.29 (s, 3H), 3.89 (s, 3H), 7.83 (s, 1H), 8.04 (dd, J=8.5, 1.8 Hz, 1H), 8.67 (s, 1H), 11.98 (s, 1H), 12.35 (s, 1H).

Step 2: Synthesis of 2-(3,4-dichloro-5-methyl-1H-pyrrole-2-carboxamido)benzo[d]thiazole-6-carboxylic acid Methyl 2-(3,4-dichloro-5-methyl-1H-pyrrole-2-carboxamido)benzo[d]thiazole-6-carboxylate (389 mg, 1.01 mmol) was suspended in 1,4-dioxane (20 mL), 2 M NaOH (2.53 mL, 5.06 mmol) was added and the reaction mixture was stirred at 80° C. overnight. 500 μL of 2 M NaOH was added and the reaction mixture was stirred at 80° C. overnight. The solvent was removed under reduced pressure, the residue was acidified with 1 M HCl to pH=1 and the obtained precipitate was filtered off. The crude product was purified with flash column chromatography using ethyl acetate/methanol (20/1) as an eluent.

Yield: 189 mg (50.5%); white solid.

$^1$H NMR (400 MHz, DMSO-$d_6$) δ 2.28 (s, 3H), 7.79 (d, J=8.5 Hz, 1H), 8.02 (dd, J=8.5, 1.7 Hz, 1H), 8.62 (d, J=1.4 Hz, 1H), 11.42-12.40 (m, 1H), 12.48 (s, 1H).

$^{13}$C NMR (101 MHz, DMSO-$d_6$) δ 10.95, 109.90, 115.55, 117.14, 119.36, 123.84, 125.73, 127.41, 129.93, 131.24, 150.68, 157.58, 161.58, 167.00.

HRMS (ESI$^-$) m/z for $C_{14}H_3Cl_2N_3O_3S$ ([M–H]$^-$): calculated 367.9658, found 367.9671.

HPLC: $t_r$ 8.190 min (98.5% at 254 nm, 98.7% at 280 nm), method A.

(Example 2) Synthesis of 2-(4,5-dibromo-1H-pyrrole-2-carboxamido)benzo[d]thiazole-6-carboxylic acid

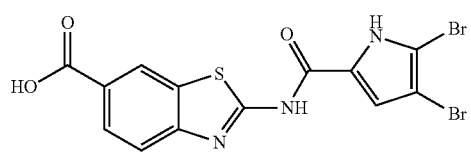 [SMILES: O=C(O)c1ccc2nc(NC(=O)c3cc(Br)c(Br)[nH]3)sc2c1]

Exemplified Compound No. 2

Step 1: Synthesis of methyl 2-(4,5-dibromo-1H-pyrrole-2-carboxamido)benzo[d]thiazole-6-carboxylate To a solution of methyl 2-aminobenzo[d]thiazole-6-carboxylate (500 mg, 2.40 mmol) in N,N-dimethylformamide Na$_2$CO$_3$ (255 mg, 2.40 mmol) and 2,2,2-trichloro-1-(4,5-dibromo-1H-pyrrole-2-yl)-ethan-1-one (0.968 g, 2.64 mmol) were added and the reaction mixture was stirred at 80° C. overnight. The reaction mixture was cooled to room temperature, 10% citric acid aqueous solution was added and the mixture was cooled on ice bath. The precipitate that formed was filtered off and dried. Yield: 91.6% (1.01 g); light brown solid.

$^1$H NMR (400 MHz, DMSO-$d_6$) δ 3.89 (s, 3H), 7.55 (d, J=8.5 Hz, 1H), 7.81 (s, 1H), 8.04 (dd, J=8.5, 1.8 Hz, 1H), 8.68 (d, J=1.8 Hz, 1H), 12.84 (s, 1H), 13.30 (s, 1H).

HRMS (ESI$^-$) m/z for $C_{14}H_3Br_2N_3O_3S$ ([M–H]$^-$): calculated 455.8653, found 455.8663.

Step 2: Synthesis of 2-(4,5-dibromo-1H-pyrrole-2-carboxamido)benzo[d]thiazole-6-carboxylic acid Methyl 2-(4,5-dibromo-1H-pyrrole-2-carboxamido)benzo[d]thiazole-6-carboxylate (0.800 g, 1.74 mmol) was suspended in 1,4-dioxane (30 mL), 2 M NaOH (4.35 mL, 8.70 mmol) was added and the reaction mixture was stirred at 80° C. overnight. The solvent was removed under reduced pressure, the residue was acidified with 1 M HCl to pH=1 and the obtained precipitate was filtered off and dried.

Yield: 565 mg (68.5%); brown solid.

$^1$H NMR (400 MHz, DMSO-$d_6$) δ 7.55 (d, J=2.7 Hz, 1H), 7.82 (d, J=8.5 Hz, 1H), 8.02 (dd, J=8.5, 1.7 Hz, 1H), 8.64 (d, J=1.4 Hz, 1H), 12.83 (s, 1H), 13.31 (s, 1H).

HRMS (ESI$^-$) m/z for $C_{13}H_6Br_2N_3O_3S$ ([M–H]$^-$): calculated 441.8497, found 441.8501.

HPLC: $t_r$ 7.097 min (96.2% at 254 nm, 96.5% at 280 nm), method A.

(Example 3) Synthesis of 2-(4,5-dichloro-1H-pyrrole-2-carboxamido)benzo[d]thiazole-6-carboxylic acid

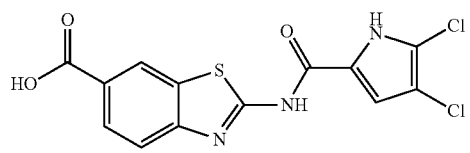 [SMILES: O=C(O)c1ccc2nc(NC(=O)c3cc(Cl)c(Cl)[nH]3)sc2c1]

Exemplified Compound No. 3

Step 1: Synthesis of methyl 2-(4,5-dichloro-1H-pyrrole-2-carboxamido)benzo[d]thiazole-6-carboxylate The same operation as in Example 2 (Step 1) was performed using 2,2,2-trichloro-1-(4,5-dichloro-1H-pyrrole-2-yl)-ethan-1-one (295 mg, 1.06 mmol). Yield: 240 mg (70.0%); off-white solid.

¹H NMR (400 MHz, DMSO-d₆) δ 3.89 (s, 3H), 7.54 (s, 1H), 7.84 (d, J=8.5 Hz, 1H), 8.04 (dd, J=8.5, 1.7 Hz, 1H), 8.68 (d, J=1.7 Hz, 1H), 12.87 (s, 1H), 13.37 (s, 1H).

HRMS (ESI⁻) m/z for C₁₄H3Cl₂N₃O₃S ([M−H]⁻): calculated 367.9660, found 367.9663.

Step 2: Synthesis of 2-(4,5-dichloro-1H-pyrrole-2-carboxamido)benzo[d]thiazole-6-carboxylic acid The same operation as in Example 2 (Step 2) was performed using methyl 2-(4,5-dichloro-1H-pyrrole-2-carboxamido)benzo[d]thiazole-6-carboxylate (240 mg, 0.65 mmol). Yield: 205 mg (88.7%); brown solid.

¹H NMR (400 MHz, DMSO-d₆) δ 7.53 (d, J=2.1 Hz, 1H), 7.82 (d, J=8.4 Hz, 1H), 8.02 (dd, J=8.5, 1.7 Hz, 1H), 8.64 (d, J=1.7 Hz, 1H), 12.86 (s, 1H), 13.37 (s, 1H).

HRMS (ESI⁻) m/z for C₁₃H6Cl₂N₃O₃S ([M−H]⁻): calculated 353.9498, found 353.9507.

(Example 4) Synthesis of 2-(3,4-dichloro-5-methyl-1H-pyrrole-2-carboxamido)benzo[d]thiazole-5-carboxylic acid

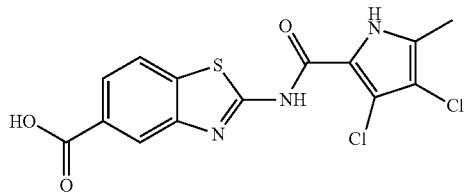 [SMILES: Cc1[nH]c(C(=O)Nc2nc3cc(C(=O)O)ccc3s2)c(Cl)c1Cl]

Exemplified Compound No. 4

Step 1: Synthesis of methyl 2-(3,4-dichloro-5-methyl-1H-pyrrole-2-carboxamido)benzo[d]thiazole-5-carboxylate The same operation as in Example 1 (Step 1) was performed using methyl 2-aminobenzo[d]thiazole-5-carboxylate (250 mg, 1.20 mmol). The crude product was dispersed in acetone (100 mL), sonicated, filtered off and dried. Yield: 210 mg (45.5%); off-white solid.

¹H NMR (400 MHz, DMSO-d₆) δ 2.24 (s, 3H), 3.93 (s, 3H), 7.81 (d, J=8.8 Hz, 1H), 8.09 (dd, J=8.9, 2.5 Hz, 1H), 8.54 (d, J=2.5 Hz, 1H), 9.92 (s, 1H), 12.20 (s, 1H).

¹³C NMR (101 MHz, DMSO-d₆) δ 10.92, 53.26, 108.85, 111.83, 112.32, 119.13, 122.35, 122.45, 125.79, 126.38, 128.34, 128.61, 138.86, 157.52, 165.94.

Step 2: Synthesis of 2-(3,4-dichloro-5-methyl-1H-pyrrole-2-carboxamido)benzo[d]thiazole-5-carboxylic acid Methyl 2-(3,4-dichloro-5-methyl-1H-pyrrole-2-carboxamido)benzo[d]thiazole-5-carboxylate (100 mg, 0.260 mmol) was dispersed in 1,4-dioxane (2.5 mL) and 2 M NaOH (0.650 mL, 1.30 mmol) was added and the reaction mixture was stirred at room temperature overnight. The reaction mixture was cooled down to room temperature and acidified using Amberlite IR120 ion exchange resin (pH<5) and stirred at room temperature for 5 min. DMF was added to dissolve the precipitate formed. The resin was filtered off and the filtrate was evaporated to dryness. The residue was dispersed in acetone, sonicated and filtered off. The product was washed with acetonitrile and diethyl ether and dried. Yield: 64 mg (66.4%); off-white solid.

¹H NMR (400 MHz, DMSO-d₆) δ 2.25 (s, 3H), 7.79 (d, J=8.8 Hz, 1H), 8.09 (dd, J=8.8, 2.3 Hz, 1H), 8.50 (d, J=2.2 Hz, 1H), 9.88 (s, 1H), 12.21 (s, 1H).

HRMS (ESI⁻) m/z for C₁₄H3Cl₂N₃O₃S ([M−H]⁻): calculated 367.9669, found 367.9661.

HPLC: t_r 9.373 min (96.3% at 254 nm, 96.6% at 280 nm), method A.

(Example 5) Synthesis of 2-(3,4-dichloro-5-methyl-1H-pyrrole-2-carboxamido)-4-fluorobenzo[d]thiazole-6-carboxylic acid

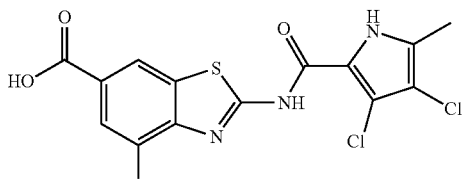

Exemplified Compound No. 5

Step 1: Synthesis of methyl 3-fluoro-4-nitrobenzoate

To a solution of 3-fluoro-4-nitrobenzoic acid (9.55 g, 51.6 mmol) in methanol (100 mL) H₂SO₄ (12.6 mL, 236 mmol) was added and the solution was stirred at 65° C. for 48 h. The solvent was removed in vacuo, the residue dissolved in ethyl acetate (100 mL) and neutralised with saturated aqueous NaHCO₃ solution (200 mL). The phases were separated, the water phase was extracted with ethyl acetate (3×75 mL), and the combined organic phases were washed with brine (3×75 mL), dried over Na₂SO₄, filtered and the solvent removed in vacuo. Yield: 10.0 g (97.4%); pale yellow crystals.

¹H NMR (400 MHz, DMSO-d₆) δ 3.92 (s, 3H), 7.96 (ddd, J=8.5, 1.8, 1.0 Hz, 1H), 8.03 (dd, J=11.4, 1.5 Hz, 1H), 8.29 (dd, J=8.5, 7.5 Hz, 1H).

Step 2: Synthesis of methyl 4-amino-3-fluorobenzoate

3-Fluoro-4-nitrobenzoic acid (956 mg, 4.85 mmol) was dissolved in methanol (30 mL) under argon atmosphere, Pd/C (180 mg) was added and the reaction mixture was stirred at room temperature under hydrogen atmosphere for 4 h. The catalyst was filtered off and the solvent removed in vacuo.

Yield: 769 mg (94.7%); light grey crystals.

¹H NMR (400 MHz, DMSO-d₆) δ 3.76 (s, 3H), 6.09 (s, 2H), 6.78 (m, 1H), 7.51 (m, 2H).

Step 3: Synthesis of methyl 2-amino-4-fluorobenzo[d]thiazole-6-carboxylate

To a solution of methyl 4-amino-3-fluorobenzoate (2.84 g, 16.8 mmol) and KSCN (6.52 g, 67.1 mmol) in acetic acid (40 mL) cooled to 10° C. bromine (1.72 mL, 33.5 mmol) in acetic acid (2 mL) was added dropwise. The reaction mixture was stirred at room temperature overnight. The suspension was cooled on ice bath and 25% aqueous NH$_3$ solution (200 mL) was added dropwise. The precipitate was filtered off, suspended in ethyl acetate (180 mL) and water (100 mL), filtered off and dried. The residue was dispersed in methanol (100 mL), sonicated, heated, filtered and successively washed with hot methanol and the mother liquid evaporated under reduced pressure. Yield: 1.02 g (26.9%); yellow solid.

$^1$H NMR (400 MHz, DMSO-d$_6$) δ 3.85 (s, 3H), 7.58 (dd, J=11.5, 1.6 Hz, 1H), 8.16 (s, 2H), 8.18 (d, J=1.6 Hz, 1H).

Step 4: Synthesis of methyl 2-(3,4-dichloro-5-methyl-1H-pyrrole-2-carboxamido)-4-fluorobenzo[d]thiazole-6-carboxylate The same operation as in Example 1 (Step 1) was performed using methyl 2-amino-4-fluorobenzo[d]thiazole-6-carboxylate (350 mg, 1.55 mmol). Yield: 242 mg (38.9%); brown solid.

$^1$H NMR (400 MHz, DMSO-d$_6$) δ 2.28 (s, 3H), 3.90 (s, 3H), 7.78 (dd, J=11.2, 1.5 Hz, 1H), 8.55 (d, J=1.5 Hz, 1H), 12.30 (s, 1H), 12.37 (s, 1H).

Step 5: Synthesis of 2-(3,4-dichloro-5-methyl-1H-pyrrole-2-carboxamido)-4-fluorobenzo[d]thiazole-6-carboxylic acid The same operation as in Example 1 (Step 2) was performed using methyl 2-(3,4-dichloro-5-methyl-1H-pyrrole-2-carboxamido)-4-fluorobenzo[d]thiazole-6-carboxylate (100 mg, 0.249 mmol). The crude product was dispersed in acetonitrile, sonicated, heated, the precipitate filtered off and dried. Yield: 43 mg (44.5%); brown solid.

$^1$H NMR (400 MHz, DMSO-d$_6$) δ 2.29 (s, 3H), 7.75 (dd, J=11.2, 1.5 Hz, 1H), 8.52 (d, J=1.4 Hz, 1H), 12.26 (s, 1H), 12.34 (s, 1H), 13.23 (br s, 1H).

$^{13}$C NMR (101 MHz, DMSO-d$_6$) δ 11.04, 110.04, 112.37, 112.57, 115.79, 116.67, 120.08, 120.11, 126.81, 130.35, 134.56, 156.67, 161.63, 166.20.

HRMS (ESI$^-$) m/z for C$_{14}$H7Cl$_2$FN$_3$O$_3$S ([M−H]$^-$): calculated 385.9580, found 385.9564.

HPLC: t$_r$ 8.983 min (96.3% at 220 nm, 95.1% at 254 nm), method A.

(Example 6). Synthesis of 2-(4,5-dibromo-1H-pyrrole-2-carboxamido)-4-hydroxybenzo[d]thiazole-6-carboxylic acid

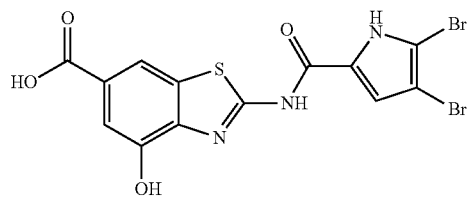 [SMILES: O=C(O)c1cc(O)c2nc(NC(=O)c3cc(Br)c(Br)[nH]3)sc2c1]

Exemplified Compound No. 6

Step 1: Synthesis of methyl 3-hydroxy-4-nitrobenzoate

To a suspension of 3-hydroxy-4-nitrobenzoic acid (10.0 g, 54.6 mmol) in methanol (200 mL) cooled on ice bath thionyl chloride (11.9 mL, 163.8 mmol) was added dropwise. The mixture was stirred at 65° C. overnight upon which a clear solution formed. The solvent was evaporated under reduced pressure. The residue was dissolved in ethyl acetate (150 mL) and the organic phase was washed with water (60 mL), saturated aqueous NaHCO$_3$ solution (32×60 mL) and brine (2×50 mL), dried over Na$_2$SO$_4$, filtered and the solvent removed in vacuo. Yield: 9.64 g (89.6%); yellow solid.

$^1$H NMR (400 MHz, CDCl$_3$) δ 3.97 (s, 3H), 7.62 (dd, J=8.8, 1.8 Hz, 1H), 7.84 (d, J=1.7 Hz, 1H), 8.18 (d, J=8.8 Hz, 1H), 10.51 (s, 1H).

Step 2: Synthesis of methyl 3-(((tert-butyldimethylsilyl)oxy)-4-nitrobenzoate

To a solution of methyl 3-hydroxy-4-nitrobenzoate (2.00 g, 10.4 mmol) in pyridine (25 mL) tert-butyldimethylsilyl chloride (2.14 g, 14.2 mmol) was added. Reaction mixture was stirred at room temperature overnight. Then ethyl acetate (85 mL) was added and solution washed with 1 M HCl (4×50 mL). Organic phase was dried over Na$_2$SO$_4$, filtered and the solvent removed in vacuo. Crude oily product was used in Step 3 without further purification.

Step 3: Synthesis of methyl 4-amino-3-((tert-butyldimethylsilyl)oxy)benzoate

The same operation as in Example 5 (Step 2) was performed using crude methyl 3-((tert-butyldimethylsilyl)oxy)-4-nitrobenzoate (2.8 g) from Step 2 above. Crude product was purified using flash column chromatography using ethyl acetate/hexane (1:2) as eluent. Yield: 1.62 g (56.0%, over two steps); white solid.

$^1$H NMR (400 MHz, DMSO-d$_6$) δ 0.22 (s, 6H), 0.98 (s, 9H), 3.74 (s, 3H), 5.39 (s, 2H), 6.70 (d, J=8.3 Hz, 1H), 7.23 (d, J=1.9 Hz, 1H), 7.38 (dd, J=8.3, 1.9 Hz, 1H).

Step 4: Synthesis of methyl 2-amino-4-hydroxybenzo[d]thiazole-6-carboxylate

To a solution of methyl 4-amino-3-((tert-butyldimethylsilyl)oxy)benzoate (1.00 g, 3.55 mmol) and KSCN (0.70 g, 7.11 mmol) in acetic acid (8 mL) cooled to 10° C. bromine (0.183 mL, 3.55 mmol) in acetic acid (3 mL) was added dropwise. The reaction mixture was stirred at room temperature overnight and turned to orange suspension. The suspension was cooled on ice bath and saturated aqueous NaHCO$_3$ solution (350 mL) was added dropwise. The obtained suspension was extracted with ethyl acetate (3×100 mL). Combined organic phase was dried over Na$_2$SO$_4$, filtered and the solvent removed in vacuo.

Yield: 230 mg (28.9%); yellow solid.

$^1$H NMR (400 MHz, DMSO-d$_6$) δ 3.81 (s, 3H), 7.28 (d, J=1.6 Hz, 1H), 7.69 (s, 2H), 7.78 (d, J=1.6 Hz, 1H), 9.66 (s, 1H).

Step 5: Synthesis of methyl 2-(4,5-dibromo-1H-pyrrole-2-carboxamido)-4-hydroxybenzo[d]thiazole-6-carboxylate The same operation as in Example 2 (Step 1) was performed using methyl 2-amino-4-hydroxybenzo[d]thiazole-6-carboxylate (248 mg, 0.67 mmol). Yield: 167 mg (31.8%); off-brown solid.

$^1$H NMR (400 MHz, DMSO-d$_6$) δ 3.86 (s, 3H), 7.47 (d, J=1.6 Hz, 1H), 7.56 (d, J=2.5 Hz, 1H), 8.10 (d, J=1.5 Hz, 1H), 10.32 (s, 1H), 12.90 (s, 1H), 13.26 (s, 1H).

Step 6: Synthesis of 2-(4,5-dibromo-1H-pyrrole-2-carboxamido)-4-hydroxybenzo[d]thiazole-6-carboxylic acid The same operation as in Example 2 (Step 2) was performed using methyl 2-(4,5-dibromo-1H-pyrrole-2-carboxamido)-4-hydroxybenzo[d]thiazole-6-carboxylate (100 mg, 0.21 mmol). Yield: 83 mg (85.5%); black solid.

$^1$H NMR (400 MHz, DMSO-$d_6$) δ 7.48 (d, J=1.6 Hz, 1H), 7.56 (d, J=2.8 Hz, 1H), 8.04 (d, J=1.5 Hz, 1H), 10.31 (s, 1H), 12.87 (s, 1H), 13.27 (d, J=2.8 Hz, 1H).

HRMS (ESI$^-$) m/z for $C_{13}H6Br_2N_3O_4S$ ([M–H]$^-$): calculated 457.8451, found 457.8458.

HPLC: $t_r$ 5.173 min (98.8% at 254 nm, 97.9% at 280 nm), method A.

(Example 7). Synthesis of 2-(3,4-dichloro-5-methyl-1H-pyrrole-2-carboxamido)-4-hydroxybenzo[d]thiazole-6-carboxylic acid

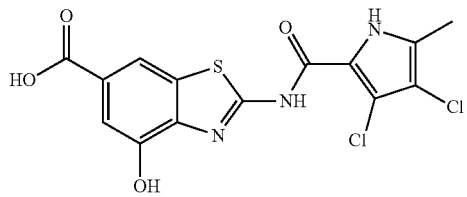 [SMILES: Cc1[nH]c(C(=O)Nc2nc3c(O)cc(C(=O)O)cc3s2)c(Cl)c1Cl]

Exemplified Compound No. 7

Step 1: Synthesis of methyl 2-amino-4-((tert-butyldimethylsilyl)oxy)benzo[d]thiazole-6-carboxylate The same operation as in Example 6 (Step 2) was performed using methyl 2-amino-4-hydroxybenzo[d]thiazole-6-carboxylate (150 mg, 0.67 mmol) synthesized in Step 4 of the Example 6. Crude product was purified using flash column chromatography using ethylacetate/hexane (1:2) as eluent. Yield: 87 mg (38.4%); beige solid.

$^1$H NMR (400 MHz, DMSO-$d_6$) δ 0.22 (s, 6H), 0.99 (s, 9H), 3.81 (s, 3H), 7.26 (d, J=1.6 Hz, 1H), 7.79 (s, 2H), 7.92 (d, J=1.6 Hz, 1H).

Step 2: Synthesis of methyl 4-((tert-butyldimethylsilyl)oxy)-2-(3,4-dichloro-5-methyl-1H-pyrrole-2-carboxamido)benzo[d]thiazole-6-carboxylate The same operation as in Example 1 (Step 1) was performed using methyl 2-amino-4-((tert-butyldimethylsilyl)oxy)benzo[d]thiazole-6-carboxylate (87 mg, 0.26 mmol). Yield: 70 mg (52.9%); white solid.

$^1$H NMR (400 MHz, DMSO-$d_6$) δ 2.10 (s, 3H), 3.87 (s, 3H), 7.41 (s, 1H), 8.26 (s, 1H), 11.84 (s, 1H), 12.46 (s, 1H).

Step 3: Synthesis of 2-(3,4-dichloro-5-methyl-1H-pyrrole-2-carboxamido)-4-hydroxybenzo[d]thiazole-6-carboxylic acid The same operation as in Example 1 (Step 2) was performed using methyl 4-((tert-butyldimethylsilyl)oxy)-2-(3,4-dichloro-5-methyl-1H-pyrrole-2-carboxamido)benzo[d]thiazole-6-carboxylate (70 mg, 0.21 mmol). Yield: 7.8 mg (14.8%); brown solid.

$^1$H NMR (400 MHz, DMSO-$d_6$) δ 2.27 (s, 3H), 7.44 (d, J=1.6 Hz, 1H), 8.05 (d, J=1.5 Hz, 1H), 10.25 (s, 1H), 11.93 (s, 1H), 12.36 (s, 1H), 12.80 (s, 1H).

HRMS (ESI$^-$) m/z for $C_{14}H3Cl_2N_3O_4S$ ([M–H]$^-$): calculated 383.9618, found 383.9622.

HPLC: $t_r$ 6.310 min (96.2% at 254 nm, 95.3% at 280 nm), method A.

(Example 8) Synthesis of 2-(3,4-dichloro-5-methyl-1H-pyrrole-2-carboxamido)-4-methoxybenzo[d]thiazole-6-carboxylic acid

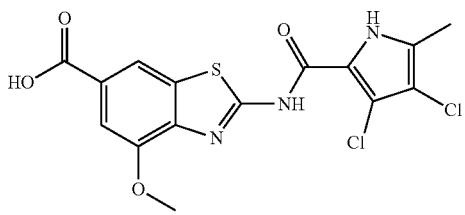 [SMILES: COc1cc(C(=O)O)cc2sc(NC(=O)c3[nH]c(C)c(Cl)c3Cl)nc12]

Exemplified Compound No. 8

Step 1: Synthesis of methyl 3-methoxy-4-nitrobenzoate

To a suspension of methyl 3-hydroxy-4-nitrobenzoate (3.00 g, 15.2 mmol) synthesized in Step 1 of the Example 6 and $K_2CO_3$ (3.16 g, 22.8 mmol) in DMF (20 mL) methyl iodide (1.9 mL, 30.5 mmol) was added dropwise and the reaction mixture was stirred at room temperature overnight. The solvent was removed in vacuo and the residue dissolved in ethyl acetate (30 mL) and washed with water (2×20 mL) and brine (20 mL). The organic phase was dried over $Na_2SO_4$, filtered and the solvent evaporated under reduced pressure. Yield: 3.00 g (93.4%); off-white crystals.

$^1$H NMR (400 MHz, DMSO-$d_6$) δ 3.92 (s, 3H), 4.00 (s, 3H), 7.68 (dd, J=8.3, 1.6 Hz, 1H), 7.78 (d, J=1.6 Hz, 1H), 8.01 (d, J=8.6 Hz, 1H).

Step 2: Synthesis of methyl 4-amino-3-methoxybenzoate

Methyl 3-methoxy-4-nitrobenzoate (2.98 g, 14.1 mmol) was dissolved in methanol/tetrahydrofuran (7:3, 100 mL) under argon atmosphere, Pd/C (500 mg) was added and the reaction mixture was stirred at room temperature under hydrogen atmosphere overnight. The catalyst was filtered off and the solvent removed in vacuo. Yield: 2.39 g (93.4%); light grey crystals.

$^1$H NMR (400 MHz, DMSO-$d_6$) δ 3.76 (s, 3H), 3.81 (s, 3H), 5.61 (br s, 2H), 6.65 (d, J=8.2 Hz, 1H), 7.29 (d, J=1.8 Hz, 1H), 7.39 (dd, J=8.2, 1.8 Hz, 1H).

Step 3: Synthesis of methyl 2-amino-4-methoxybenzo[d]thiazole-6-carboxylate

The same operation as in Example 5 (Step 3) was performed using methyl 4-amino-3-methoxybenzoate (2.34 g, 12.9 mmol) obtained in Step 3 above. The product was obtained after filtration of the precipitate out of ethyl acetate/water mixture. Yield: 2.72 g (88.3%); orange solid.

¹H NMR (400 MHz, DMSO-d₆) δ 3.84 (s, 3H), 3.88 (s, 3H), 7.35 (d, J=1.5 Hz, 1H), 7.85 (s, 2H), 7.96 (d, J=1.6 Hz, 1H).

Step 4: Synthesis of methyl 2-(3,4-dichloro-5-methyl-1H-pyrrole-2-carboxamido)-4-methoxybenzo[d]thiazole-6-carboxylate The same operation as in Example 1 (Step 1) was performed using methyl 2-amino-4-methoxybenzo[d]thiazole-6-carboxylate (368 mg, 1.55 mmol) obtained in Step 4 above. Yield: 345 mg (53.9%); brown solid.
¹H NMR (400 MHz, DMSO-d₆) δ 2.28 (s, 3H), 3.90 (s, 3H), 4.00 (s, 3H), 7.50 (d, J=1.4 Hz, 1H), 8.29 (d, J=1.2 Hz, 1H), 12.15 (s, 1H), 12.29 (s, 1H).

Step 5: Synthesis of 2-(3,4-dichloro-5-methyl-1H-pyrrole-2-carboxamido)-4-methoxybenzo[d]thiazole-6-carboxylic acid The same operation as in Example 1 (Step 2) was performed using methyl 2-(3,4-dichloro-5-methyl-1H-pyrrole-2-carboxamido)-4-methoxybenzo[d]thiazole-6-carboxylate (162 mg, 0.391 mmol) obtained in Step 5 above. Yield: 120 mg (76.7%); brown solid.
¹H NMR (400 MHz, DMSO-d₆) δ 2.28 (s, 3H), 3.98 (s, 3H), 7.50 (d, J=1.4 Hz, 1H), 8.24 (d, J=1.4 Hz, 1H), 12.02 (br s, 1H), 12.41 (s, 1H), 12.66 (br s, 1H).
¹³C NMR (101 MHz, DMSO-d₆) δ 11.01, 55.77, 107.78, 109.87, 115.41, 116.07, 116.91, 126.79, 130.03, 132.65, 141.53, 151.03, 156.69, 159.52, 167.07.
HRMS (ESI⁻) m/z for $C_{15}H_{10}Cl_2N_3O_4S$ ([M–H]⁻): calculated 397.9764, found 397.9779.
HPLC: $t_r$ 7.867 min (96.7% at 254 nm, 96.5% at 280 nm), method A.

(Example 9) Synthesis of 4-(benzyloxy)-2-(3,4-dichloro-5-methyl-1H-pyrrole-2-carboxamido)benzo[d]thiazole-6-carboxylic acid

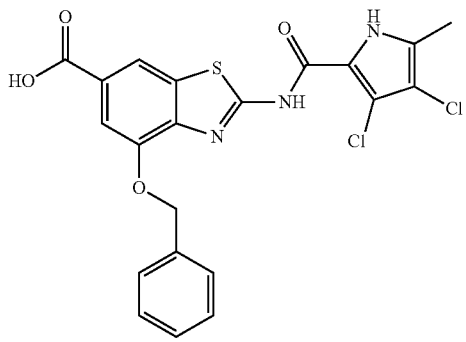 [SMILES: Cc1[nH]c(C(=O)Nc2nc3c(OCc4ccccc4)cc(C(=O)O)cc3s2)c(Cl)c1Cl]

Exemplified Compound No. 9

Step 1: Synthesis of methyl 3-(benzyloxy)-4-nitrobenzoate

To a suspension of methyl 3-hydroxy-4-nitrobenzoate (1.19 g, 6.02 mmol) synthesized in Step 1 of the Example 6 and K₂CO₃ (1.66 g, 12.04 mmol) in acetonitrile (20 mL) benzyl bromide (0.788 mL, 6.62 mmol) was added dropwise and the reaction mixture was stirred at 60° C. overnight. The solvent was removed in vacuo and the residue dissolved in ethyl acetate (30 mL) and washed with water (2×20 mL) and brine (20 mL). The organic phase was dried over Na₂SO₄, filtered and the solvent evaporated under reduced pressure. Yield: 1.54 g (89.6%); yellow crystals.
¹H NMR (400 MHz, DMSO-d₆) δ 3.92 (s, 3H), 5.41 (s, 2H), 7.29-7.51 (m, 5H), 7.70 (dd, J=8.3, 1.6 Hz, 1H), 7.90 (d, J=1.5 Hz, 1H), 8.03 (d, J=8.3 Hz, 1H).

Step 2: Synthesis of methyl 4-amino-3-(benzyloxy)benzoate

To a solution of methyl 3-(benzyloxy)-4-nitrobenzoate (1.48 g, 5.17 mmol) in ethyl acetate/methanol (1.5:1, 25 mL), SnCl₂ (4.90 g, 25.8 mmol) was added and the reaction mixture stirred at 55° C. overnight. The solvent was removed in vacuo and to the residue NaHCO₃ (220 mL) was added dropwise on an ice bath. The obtained white suspension was sonicated for 30 min. Ethyl acetate was added and the precipitate was filtered off. The phases in the mother liquid were separated and water phase was extracted with additional ethyl acetate. The precipitate was also resuspended in ethyl acetate and filtered again. The combined organic phases were washed with brine, dried over Na₂SO₄, filtered and the solvent removed in vacuo. Yield: 1.23 g (92.6%); dark yellow solid.
¹H NMR (400 MHz, DMSO-d₆) δ 3.75 (s, 3H), 5.17 (s, 2H), 5.68 (br s, 2H), 6.68 (d, 1H), 7.29-7.45 (m, 5H), 7.49-7.56 (m, 2H), Step 3: Synthesis of methyl 2-amino-4-(benzyloxy)benzo[d]thiazole-6-carboxylate The same operation as in Example 5 (Step 3) was performed using methyl 4-amino-3-(benzyloxy)benzoate (229 mg, 0.89 mmol). Yield: 250 mg (89.3%); orange solid.
¹H NMR (400 MHz, DMSO-d₆) δ 3.83 (s, 3H), 5.24 (s, 2H), 7.32-7.44 (m, 3H), 7.46 (d, J=1.6 Hz, 1H), 7.48-7.53 (m, 2H), 7.91 (s, 2H), 7.98 (d, J=1.5 Hz, 1H).

Step 4: Synthesis of methyl 4-(benzyloxy)-2-(3,4-dichloro-5-methyl-1H-pyrrole-2-carboxamido)benzo[d]thiazole-6-carboxylate The same operation as in Example 1 (Step 1) was performed using methyl 2-amino-4-(benzyloxy)benzo[d]thiazole-6-carboxylate (270 mg, 0.859 mmol). Yield: 311 mg (73.9%); grey solid.
¹H NMR (400 MHz, DMSO-d₆) δ 2.26 (s, 3H), 3.89 (s, 3H), 5.32 (s, 2H), 7.33-7.49 (m, 3H), 7.54 (m, 2H), 7.62 (d, J=1.3 Hz, 1H), 8.29 (s, 1H), 12.19 (s, 1H), 12.22 (s, 1H).

Step 5: Synthesis of 4-(benzyloxy)-2-(3,4-dichloro-5-methyl-1H-pyrrole-2-carboxamido)benzo[d]thiazole-6-carboxylic acid The same operation as in Example 1 (Step 2) was performed using methyl 4-(benzyloxy)-2-(3,4-dichloro-5-methyl-1H-pyrrole-2-carboxamido)benzo[d]thiazole-6-carboxylate (100 mg, 0.204 mmol).
Yield: 40 mg (41.2%); brown solid.
¹H NMR (400 MHz, DMSO-d₆) δ 2.26 (s, 3H), 5.32 (s, 2H), 7.57-7.35 (m, 5H), 7.61 (d, J=1.3 Hz, 1H), 8.25 (d, J=1.0 Hz, 1H), 12.16 (s, 1H), 12.23 (s, 1H), 13.00 (s, 1H).
HRMS (ESI⁻) m/z for $C_{21}H_{14}Cl_2N_3O_4S$ ([M–H]⁻): calculated 474.0077, found 474.0095.
HPLC: $t_r$ 11.487 min (98.1% at 254 nm, 95.5% at 280 nm), method A.

(Example 10) Synthesis of 4-(2-((6-carboxy-2-(3,4-dichloro-5-methyl-1H-pyrrole-2-carboxamido)benzo[d]thiazol-4-yl)oxy)ethyl)morpholin-4-ium chloride

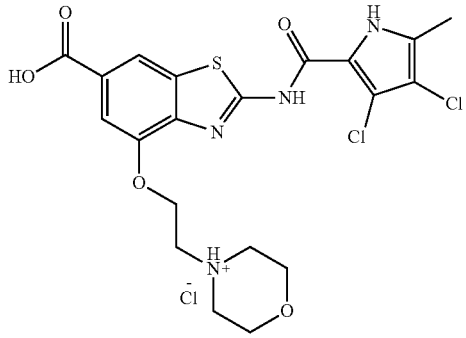

Exemplified Compound No. 10

Step 1: Synthesis of methyl 3-(2-morpholinoethoxy)-4-nitrobenzoate

To a suspension of methyl 3-hydroxy-4-nitrobenzoate (500 mg, 2.54 mmol) synthesized in Step 1 of the Example 6 and $Na_2CO_3$ (538 mg, 5.07 mmol) in DMF (10 mL) 4-(2-chloroethyl)morpholine hydrochloride (566 mg, 3.04 mmol) was added and the reaction mixture was stirred at 80° C. overnight. The solvent was removed in vacuo and the residue dissolved in ethyl acetate (50 mL) and washed with water (25 mL) and brine (20 mL). The organic phase was dried over $Na_2SO_4$, filtered and the solvent evaporated under reduced pressure. Yield: 760 mg (96.6%); yellow crystals.

$^1$H NMR (400 MHz, DMSO-$d_6$) δ 2.47 (s, 4H), 2.72 (t, J=5.2 Hz, 2H), 3.50-3.60 (m, 4H), 3.91 (s, 1H), 4.37 (t, J=5.5 Hz, 2H), 7.67 (dd, J=8.3, 1.6 Hz, 1H), 7.85 (d, J=1.6 Hz, 1H), 7.99 (d, J=8.3 Hz, 1H).

Step 2: Synthesis of methyl 4-amino-3-(2-morpholinoethoxy)benzoate

The same operation as in Example 5 (Step 2) was performed using methyl 3-(2-morpholinoethoxy)-4-nitrobenzoate (750 mg, 2.42 mmol). Yield: 672 mg (99.3%); off-green crystals.

$^1$H NMR (400 MHz, DMSO-$d_6$) δ 2.46-2.50 (m, 4H), 2.64-2.80 (m, 2H), 3.54-3.66 (m, 4H), 3.75 (s, 3H), 4.08 (t, J=5.5 Hz, 2H), 5.68 (s, 2H), 6.65 (d, J=8.2 Hz, 1H), 7.34 (d, J=1.8 Hz, 1H), 7.40 (dd, J=8.2, 1.8 Hz, 1H).

Step 3: Synthesis of methyl 2-amino-4-(2-morpholinoethoxy)benzo[d]thiazole-6-carboxylate The same operation as in Example 5 (Step 3) was performed using methyl 4-amino-3-(2-morpholinoethoxy)benzoate (627 mg, 2.24 mmol). Yield: 431 mg (57.1%); orange solid.

$^1$H NMR (400 MHz, DMSO-$d_6$) δ 2.55 (s, 4H), 2.80 (s, 2H), 3.61 (s, 4H), 3.83 (s, 3H), 4.25 (s, 2H), 7.39 (s 1H), 7.91 (s, 2H), 7.97 (s, 1H).

Step 4: Synthesis of 4-(2-((2-(3,4-dichloro-5-methyl-1H-pyrrole-2-carboxamido)-6-(methoxycarbonyl)benzo[d]thiazol-4-yl)oxy)ethyl)morpholin-4-ium chloride The same operation as in Example 1 (Step 1) was performed using methyl 2-amino-4-(2-morpholinoethoxy)benzo[d]thiazole-6-carboxylate (261 mg, 0.773 mmol) obtained in Step 3 above.

Yield: 70 mg (16.5%); beige solid.

$^1$H NMR (400 MHz, DMSO-$d_6$) δ 2.28 (s, 3H), 3.20-3.30 (m, 2H), 3.65 (s, 4H), 3.79 (t, 2H), 3.90 (s, 3H), 4.04 (d, J=12.5 Hz, 2H), 4.69 (s, 2H), 7.60 (d, J=1.4 Hz, 1H), 8.36 (s, 1H), 10.68 (s, 1H), 12.12 (s, 1H), 12.68 (s, 1H).

Step 5: Synthesis of 4-(2-((6-carboxy-2-(3,4-dichloro-5-methyl-1H-pyrrole-2-carboxamido)benzo[d]thiazol-4-yl)oxy)ethyl)morpholin-4-ium chloride The same operation as in Example 1 (Step 2) was performed using 4-(2-((2-(3,4-dichloro-5-methyl-1H-pyrrole-2-carboxamido)-6-(methoxycarbonyl)benzo[d]thiazol-4-yl)oxy)ethyl)morpholin-4-ium chloride (70 mg, 0.127 mmol) obtained in Step 4 above. Yield: 54 mg (78.7%); brownish-red solid.

$^1$H NMR (400 MHz, DMSO-$d_6$) δ 2.29 (s, 3H), 3.32 (m, 2H), 3.66 (m, 4H), 3.84 (t, J=11.9 Hz, 2H), 4.06 (m, 2H), 4.71 (s, 2H), 7.58 (d, J=1.4 Hz, 1H), 8.30 (d, J=1.3 Hz, 1H), 11.13 (s, 1H), 12.20 (br s, 1H), 12.86 (s, 1H).

HRMS (ESI$^-$) m/z for $C_{20}H_{19}Cl_2N_4O_5S$ ([M−H]$^-$): calculated 497.0448, found 497.0458.

HPLC: $t_r$ 5.030 min (98.0% at 254 nm, 96.1% at 280 nm), method A.

(Example 11) Synthesis of 2-((6-carboxy-2-(3,4-dichloro-5-methyl-1H-pyrrole-2-carboxamido)benzo[d]thiazol-4-yl)oxy)ethan-1-aminium chloride

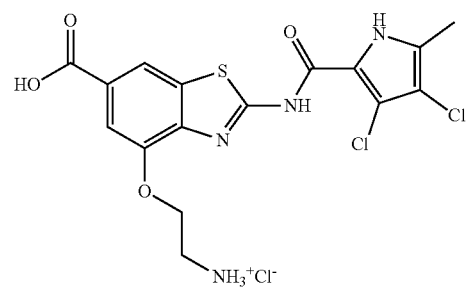

Exemplified Compound No. 11

Step 1: Synthesis of methyl 3-(2-((tert-butoxycarbonyl)amino)ethoxy)-4-nitrobenzoate To a suspension of methyl 3-hydroxy-4-nitrobenzoate (700 mg, 3.55 mmol) synthesized in Step 1 of the Example 6 and $K_2CO_3$ (1.47 g, 10.7 mmol) in DMF (20 mL) tert-butyl (2-chloroethyl)carbamate (0.957 g, 5.33 mmol) and KI (1.18 g, 7.10 mmol) were added and the reaction mixture was stirred at 80° C. overnight. The solvent was removed in vacuo and the residue dissolved in ethyl acetate (50 mL) and washed with water (25 mL) and brine (20 mL). The organic phase was dried over $Na_2SO_4$, filtered and the solvent evaporated under reduced pressure. The crude product was purified with flash column chromatography using ethyl acetate/hexane (1:3) as eluent. Yield: 260 mg (21.5%); yellow crystals.

$^1$H NMR (400 MHz, DMSO-$d_6$) δ 1.37 (s, 9H), 3.28-3.33 (m, 2H), 3.90 (s, 3H), 4.24 (t, J=5.6 Hz, 2H), 6.96 (t, J=5.3 Hz, 1H), 7.66 (dd, J=8.3, 1.6 Hz, 1H), 7.78 (d, J=1.4 Hz, 1H), 7.99 (d, J=8.3 Hz, 1H).

Step 2: Synthesis of methyl 4-amino-3-(2-((tert-butoxycarbonyl)amino)ethoxy)benzoate The same operation as in Example 5 (Step 2) was performed using methyl 3-(2-((tert-butoxycarbonyl)amino)ethoxy)-4-nitrobenzoate (250 mg, 0.735 mmol). Yield: 220 mg (96.5%); green oily product.

$^1$H NMR (400 MHz, DMSO-$d_6$) δ 1.40 (s, 9H), 3.36 (m, 2H, signal is overlapping with the signal for water), 3.75 (s, 3H), 3.90 (t, J=5.1 Hz, 2H), 5.80 (s, 2H), 6.62 (d, J=8.2 Hz, 1H), 7.18 (t, J=6.0 Hz, 1H), 7.23 (d, J=1.7 Hz, 1H), 7.38 (dd, J=8.2, 1.8 Hz, 1H).

Step 3: Synthesis of methyl 2-amino-4-(2-((tert-butoxycarbonyl)amino)ethoxy)benzo[d]thiazole-6-carboxylate The same operation as in Example 5 (Step 3) was performed using methyl 4-amino-3-(2-((tert-butoxycarbonyl)amino)ethoxy)benzoate (214 mg, 0.690 mmol). Yield: 241 mg (95.3%); orange solid.

$^1$H NMR (400 MHz, DMSO-$d_6$) δ 1.39 (s, 9H), 3.33 (q, J=6.0 Hz, 2H), 3.83 (s, 3H), 4.11 (t, J=6.0 Hz, 2H), 7.00 (t, J=5.2 Hz, 1H), 7.36 (d, J=1.6 Hz, 1H), 7.92 (br s, 2H), 7.97 (d, J=1.5 Hz, 1H).

Step 4: Synthesis of methyl 4-(2-((tert-butoxycarbonyl)amino)ethoxy)-2-(3,4-dichloro-5-methyl-1H-pyrrole-2-carboxamido)benzo[d]thiazole-6-carboxylate The same operation as in Example 1 (Step 1) was performed using methyl 2-amino-4-(2-((tert-butoxycarbonyl)amino)ethoxy)benzo[d]thiazole-6-carboxylate (200 mg, 0.544 mmol) obtained in Step 3 above. Yield: 38 mg (12.8%); beige solid.

$^1$H NMR (400 MHz, DMSO-$d_6$) δ 1.40 (s, 9H), 2.28 (s, 3H), 3.41 (m, 2H, signal is overlapping with the signal for water), 3.89 (s, 3H), 4.22 (t, J=5.8 Hz, 2H), 7.06 (t, J=4.8 Hz, 1H), 7.50 (d, J=1.4 Hz, 1H), 8.29 (s, 1H), 12.26 (s, 2H).

Step 5: Synthesis of 4-(2-((tert-butoxycarbonyl)amino)ethoxy)-2-(3,4-dichloro-5-methyl-1H-pyrrole-2-carboxamido)benzo[d]thiazole-6-carboxylic acid The same operation as in Example 1 (Step 2) was performed using methyl 4-(2-((tert-butoxycarbonyl)amino)ethoxy)-2-(3,4-dichloro-5-methyl-1H-pyrrole-2-carboxamido)benzo[d]thiazole-6-carboxylate (35 mg, 0.064 mmol) obtained in Step 4 above. Yield: 7.6 mg (22.3); brownish-red solid.

$^1$H NMR (400 MHz, DMSO-$d_6$) δ 1.39 (s, 9H), 2.28 (s, 3H), 3.39 (m, 2H, signal is overlapping with the signal for water), 4.10 (t, J=6.0 Hz, 2H), 6.96-7.05 (m, 1H), 7.34 (d, J=1.4 Hz, 1H), 7.92 (d, J=1.5 Hz, 1H), 12.70 (s, 1H), 12.80 (s, 1H), 12.97 (s, 1H).

Step 6: Synthesis of 2-((6-carboxy-2-(3,4-dichloro-5-methyl-1H-pyrrole-2-carboxamido)benzo[d]thiazol-4-yl)oxy)ethan-1-aminium chloride To a suspension of 4-(2-((tert-butoxycarbonyl)amino)ethoxy)-2-(3,4-dichloro-5-methyl-1H-pyrrole-2-carboxamido)benzo[d]thiazole-6-carboxylic acid (7.6 mg, 0.014 mmol) in 1,4-dioxane (1 mL) 4 M HCl in 1,4-dioxane (1 mL) was added and the reaction mixture was stirred at room temperature for 5 h. The precipitate in the reaction mixture was filtered off, washed with methanol and dried. Yield: 3 mg (44.9%); brownish-red solid.

$^1$H NMR (400 MHz, DMSO-$d_6$) δ 2.28 (s, 3H), 3.30 (m, 2H, signal is overlapping with the signal for water), 4.45 (t, J=5.0 Hz, 2H), 7.59 (d, J=1.1 Hz, 1H), 8.10 (s, 3H), 8.31 (s, 1H), 12.07 (br s, 1H), 12.50 (s, 1H), 13.08 (br s, 1H).

HRMS (ESI$^+$) m/z for $C_{16}H_{15}Cl_2N_4O_4S$ ([M+H]$^+$): calculated 429.0186, found 429.0187.

HPLC: $t_r$ 3.733 min (95.1% at 254 nm, 95.2% at 280 nm), method A.

(Example 12) Synthesis of 4-((4-carboxybenzyl)oxy)-2-(3,4-dichloro-5-methyl-1H-pyrrole-2-carboxamido)benzo[d]thiazole-6-carboxylic acid

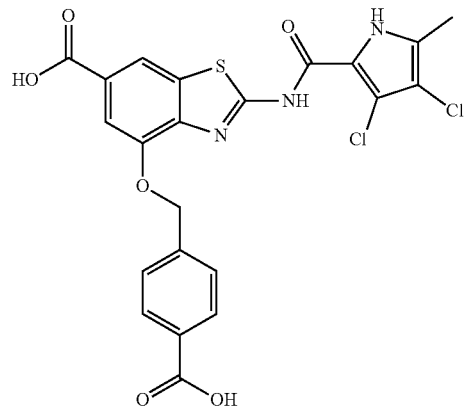 [SMILES: Cc1[nH]c(C(=O)Nc2nc3c(OCc4ccc(C(=O)O)cc4)cc(C(=O)O)cc3s2)c(Cl)c1Cl]

Exemplified Compound No. 12

Step 1: Synthesis of methyl 2-amino-4-((4-(methoxycarbonyl)benzyl)oxy)benzo[d]thiazole-6-carboxylate To a suspension of methyl 2-amino-4-hydroxybenzo[d]thiazole-6-carboxylate (100 mg, 0.446 mmol) synthesized in Step 4 of the Example 6 and $K_2CO_3$ (123 mg, 0.892 mmol) in acetonitrile methyl 4-(bromomethyl)benzoate (102 mg, 0.446 mmol) was added and the reaction mixture was stirred at 55° C. overnight. The solvent was evaporated under reduced pressure and the residue dissolved in ethyl acetate (20 mL). The organic phase was washed with saturated aqueous NaHCO$_3$ solution (2×10 mL) and brine (10 mL), dried over Na$_2$SO$_4$, filtered and the solvent removed in vacuo. The crude product was recrystallized from methanol. Yield: 69 mg (41.6%); yellow crystals.

$^1$H NMR (400 MHz, DMSO-$d_6$) δ 3.83 (s, 3H), 3.87 (s, 3H), 5.36 (s, 2H), 7.46 (d, J=1.5 Hz, 1H), 7.65 (d, J=8.3 Hz, 2H), 7.95 (s, 2H), 8.00 (m, 3H).

Step 2: Synthesis of methyl 2-(3,4-dichloro-5-methyl-1H-pyrrole-2-carboxamido)-4-((4-(methoxycarbonyl)benzyl)oxy)benzo[d]thiazole-6-carboxylate The same operation as in Example 1 (Step 1) was performed using methyl 2-amino-4-((4-(methoxycarbonyl)benzyl)oxy)benzo[d]thiazole-6-carboxylate (68 mg, 0.185 mmol). Yield: 72 mg (70.9%); light grey solid.

$^1$H NMR (400 MHz, DMSO-$d_6$) δ 2.26 (s, 3H), 3.87 (s, 3H), 3.88 (s, 3H), 5.44 (s, 2H), 7.61 (d, J=1.3 Hz, 1H), 7.69 (d, J=8.2 Hz, 2H), 8.03 (d, J=8.3 Hz, 2H), 8.31 (d, J=0.9 Hz, 1H), 12.19 (s, 1H), 12.27 (s, 1H).

Step 3: Synthesis of 4-((4-carboxybenzyl)oxy)-2-(3,4-dichloro-5-methyl-1H-pyrrole-2-carboxamido)benzo[d]thiazole-6-carboxylic acid The same operation as in Example 1 (Step 2) was performed using methyl 2-(3,4-dichloro-5-methyl-1H-pyrrole-2-carboxamido)-4-((4-(methoxycarbonyl)benzyl)oxy)benzo[d]thiazole-6-carboxylate (63 mg, 0.115 mmol). Yield: 57 mg (95.5%); brown crystals.

$^1$H NMR (400 MHz, DMSO-$d_6$) δ 2.27 (s, 3H), 5.43 (s, 2H), 7.61 (d, J=1.4 Hz, 1H), 7.66 (d, J=8.4 Hz, 2H), 8.01 (d, J=8.4 Hz, 2H), 8.27 (d, J=1.3 Hz, 1H), 12.17 (br s, 1H), 12.28 (s, 1H), 13.02 (br s, 2H).

HRMS (ESI$^-$) m/z for $C_{22}H_{14}Cl_2N_3O_6S$ ([M–H]$^-$): calculated 517.9986, found 517.9989.

HPLC: $t_r$ 8.380 min (95.4% at 254 nm, 95.0% at 280 nm), method A.

(Example 13) Synthesis of 2-(3,4-dichloro-5-methyl-1H-pyrrole-2-carboxamido)-5-hydroxybenzo[d]thiazole-6-carboxylic acid

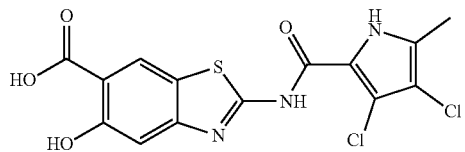 [SMILES: Cc1[nH]c(C(=O)Nc2nc3cc(O)c(C(=O)O)cc3s2)c(Cl)c1Cl]

Exemplified Compound No. 13

Step 1: Synthesis of methyl 4-amino-2-hydroxybenzoate

The same operation as in Example 5 (Step 1) was performed using 4-aminosalicylic acid (7.50 g, 49.0 mmol). Yield: 7.26 g (88.6%); brown solid; mp: 99-104° C.

$^1$H NMR (400 MHz, CDCl$_3$) δ 3.90 (s, 3H), 4.12 (s, 2H), 6.12-6.20 (m, 2H), 7.64 (dd, J=8.0, 0.9 Hz, 1H), 10.97 (s, 1H).

Step 2: Synthesis of methyl 4-((tert-butoxycarbonyl)amino)-2-hydroxybenzoate

To a solution of methyl 4-amino-2-hydroxybenzoate (9.57 g, 57.3 mmol) di-tert-butyl dicarbonate (13.8 g, 63.0 mmol) was added and the mixture was stirred at 70° C. for 48 h. The solvent was removed under reduced pressure, to the residue ethyl acetate (100 mL) and water were added and the phases were separated. Organic phase was washed with 1 M HCl (3×40 mL) and brine (3×40 mL), dried over Na$_2$SO$_4$, filtered and the solvent removed in vacuo. Crude product was purified with flash column chromatography using ethyl acetate/hexane (1:7) as an eluent. Yield: 6.52 g (43%); white crystals.

$^1$H NMR (400 MHz, CDCl$_3$) δ 1.54 (s, 9H), 3.94 (s, 3H), 6.62 (s, 1H), 6.95 (dd, J=8.7, 2.2 Hz, 1H), 7.01 (d, J=2.1 Hz, 1H), 7.76 (d, J=8.7 Hz, 1H), 10.86 (s, 1H).

Step 3: Synthesis of methyl 2-acetoxy-4-((tert-butoxycarbonyl)amino)benzoate

To a solution of methyl 4-((tert-butoxycarbonyl)amino)-2-hydroxybenzoate (1.28 g, 4.8 mmol) in acetonitrile (15 mL) pyridine (0.694 mL, 8.6 mmol) and acetic anhydride (0.869 mL, 8.6 mmol) were added, and the mixture was stirred at 70° C. for 48 h. The solvent was removed under reduced pressure and the residue dissolved in ethyl acetate (40 mL). The organic phase was washed with 1 M HCl (3×20 mL) and brine (3×20 mL), dried over Na$_2$SO$_4$, filtered and the solvent removed in vacuo. To the crude product hexane was added, the resulting suspension was sonicated, the solid was filtered off, washed with hexane and dried. Yield: 1.24 g (84%); white solid.

$^1$H NMR (400 MHz, CDCl$_3$) δ 1.54 (s, 9H), 2.36 (s, 3H), 3.86 (s, 3H), 6.74 (s, 1H) 7.14 (dd, J=8.7, 1.7 Hz, 1H), 7.40 (d, J=1.7 Hz, 1H), 7.97 (d, J=8.7 Hz, 1H).

Step 4: Synthesis of methyl 2-acetoxy-4-aminobenzoate

To methyl 2-acetoxy-4-((tert-butoxycarbonyl)amino)benzoate (1.24 g, 4.01 mmol) 2 M HCl in diethyl ether (35 mL) was added and the mixture was stirred at room temperature overnight. The product precipitated as a white solid and was filtered off, washed with ether and dried. The filtrate contained the remaining starting material so the solvent was removed under reduced pressure, to the residue 2 M HCl in diethyl ether (5 mL) was added and the mixture was stirred at room temperature overnight. The white precipitate was filtered off, washed with ether and dried. The combined product in the form of a hydrochloride salt (0.911 g) was dissolved in ethyl acetate (100 mL), and the organic phase was washed with saturated aqueous NaHCO$_3$ solution (50 mL) and brine (50 mL), dried over Na$_2$SO$_4$, filtered and the solvent removed in vacuo. Yield: 0.760 g (86%); light brown solid.

$^1$H NMR (400 MHz, DMSO-$d_6$) δ 2.23 (s, 3H), 3.68 (s, 3H), 6.20 (br s, 2H), 6.22 (d, J=2.2 Hz, 1H), 6.46 (dd, J=8.7, 2.2 Hz, 1H), 7.65 (d, J=8.7 Hz, 1H)

Step 5: Synthesis of methyl 5-acetoxy-2-aminobenzo[d]thiazole-6-carboxylate

To a suspension of methyl 2-acetoxy-4-aminobenzoate (0.716 g, 3.43 mmol) and KSCN (1.33 g, 13.7 mmol) in acetic acid (12 mL), cooled to 10° C., bromine (0.351 mL, 6.85 mmol) in acetic acid (3 mL) was added and the mixture was stirred at room temperature overnight. The suspension was cooled on ice bath and neutralised with saturated aqueous NaHCO$_3$ solution (500 mL), the resulting precipitate was filtered off and dried at 60° C. for 1.5 h. The solid was purified by adding diethyl ether (50 mL), the obtained suspension was sonicated, the solid was filtered off and washed with diethyl ether. To the crude product methanol (100 mL) was added, the mixture was heated to reflux and the undissolved solid was filtered off. Methanol was removed under reduced pressure to obtain product as a yellow solid.

$^1$H NMR (400 MHz, DMSO-d$_6$) δ 2.28 (s, 3H), 3.78 (s, 3H), 7.09 (s, 1H), 8.08 (s, 2H), 8.29 (s, 1H).

Step 6: Synthesis of methyl 5-acetoxy-2-(3,4-dichloro-5-methyl-1H-pyrrole-2-carboxamido)benzo[d]thiazole-6-carboxylate The same operation as in Example 1 (Step 1) was performed using methyl 5-acetoxy-2-aminobenzo[d]thiazole-6-carboxylate (100 mg, 0.376 mmol). The crude product was dispersed in diethyl ether (20 mL), sonicated, filtered off and dried. Yield: 56 mg (33%); brown solid.

$^1$H NMR (400 MHz, DMSO-d$_6$) δ 2.28 (s, 3H), 2.32 (s, 3H), 3.84 (s, 3H), 7.60 (s, 1H), 8.67 (s, 1H), 12.06 (s, 1H), 12.36 (s, 1H).

Step 7: Synthesis of 2-(3,4-dichloro-5-methyl-1H-pyrrole-2-carboxamido)-5-hydroxybenzo[d]thiazole-6-carboxylic acid To a suspension of methyl 5-acetoxy-2-(3,4-dichloro-5-methyl-1H-pyrrole-2-carboxamido)benzo[d]thiazole-6-carboxylate (39 mg, 0.088 mmol) in 1,4-dioxane (5 mL) 4 M NaOH (0.221 mL, 0.88 mmol) was added and the mixture was stirred at 80° C. overnight. The solvent was removed in vacuo, to the residue 1 M HCl (8 mL) was added, the resulting suspension was sonicated, the precipitate was filtered off and dried. The crude product was dispersed in diethyl ether (10 mL), sonicated, filtered off and dried. Yield: 22.3 mg (66%); brown solid.

$^1$H NMR (400 MHz, DMSO-d$_6$) δ 2.27 (s, 3H), 6.94 (s, 1H), 8.22 (s, 1H), 12.00 (s, 1H), 12.31 (s, 1H).

HRMS (ESI$^-$) m/z for $C_{14}H_9Cl_2N_3O_4S$ ([M−H]$^-$): calculated 383.9618, found 383.9621.

HPLC: t$_r$ 8.890 min (99.1% at 254 nm, 99.4% at 280 nm), method A.

(Example 14) Synthesis of 7-chloro-2-(3,4-dichloro-5-methyl-1H-pyrrole-2-carboxamido)benzo[d]thiazole-6-carboxylic acid

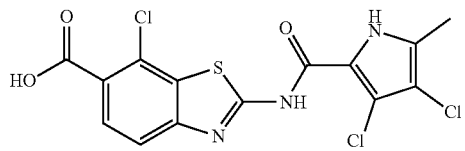

Exemplified Compound No. 14

Step 1: Synthesis of methyl 2-chloro-4-nitrobenzoate

The same operation as in Example 5 (Step 1) was performed using 2-chloro-4-nitrobenzoic acid (11.0 g, 54.6 mmol). Yield: 11.7 g (99.5%); pale yellow crystals.

$^1$H NMR (400 MHz, DMSO-d6) δ 3.93 (s, 3H), 8.06 (d, J=8.6 Hz, 1H), 8.28 (d, J=2.3 Hz, 1H), 8.40 (d, 1H).

Step 2: Synthesis of methyl 4-amino-2-chlorobenzoate

The same operation as in Example 9 (Step 2) was performed using methyl 2-chloro-4-nitrobenzoate (2.35 g, 10.9 mmol). The crude product was purified with flash column chromatography using hexane/ethyl acetate (3:1→2:1) as eluent. Yield: 1.70 g (84.1%); white crystals.

$^1$H NMR (400 MHz, DMSO-d6) δ 3.73 (s, 3H), 6.20 (s, 2H), 6.51 (dd, J=8.7, 2.3 Hz, 1H), 6.63 (d, J=2.2 Hz, 1H), 7.65 (d, J=8.6 Hz, 1H).

Step 3: Synthesis of methyl 2-amino-7-chlorobenzo[d]thiazole-6-carboxylate

The same operation as in Example 5 (Step 3) was performed using methyl 4-amino-2-chlorobenzoate (1.67 g, 8.99 mmol). After the addition of 25% aqueous NH$_3$ solution the precipitate was filtered off, dispersed in methanol (100 mL), heated, filtered, washed with methanol and dried. Yield: 1.199 g (55.0%); orange solid.

$^1$H NMR (400 MHz, DMSO-d$_6$) δ 3.84 (s, 3H), 7.34 (d, J=8.4 Hz, 1H), 7.82 (d, J=8.5 Hz, 1H), 8.15 (s, 2H).

Step 4: Synthesis of methyl 7-chloro-2-(3,4-dichloro-5-methyl-1H-pyrrole-2-carboxamido)benzo[d]thiazole-6-carboxylate The same operation as in Example 1 (Step 1) was performed using methyl 2-amino-7-chlorobenzo[d]thiazole-6-carboxylate (255 mg, 1.05 mmol). Yield: 238 mg (94.3%); light brown solid.

$^1$H NMR (400 MHz, DMSO-d6) δ 2.29 (s, 3H), 3.90 (s, 3H), 7.83 (s, 1H), 8.00 (d, J=8.5 Hz, 1H), 12.18 (s, 1H), 12.40 (s, 1H).

Step 5: Synthesis of 7-chloro-2-(3,4-dichloro-5-methyl-1H-pyrrole-2-carboxamido)benzo[d]thiazole-6-carboxylic acid The same operation as in Example 1 (Step 2) was performed using methyl 7-chloro-2-(3,4-dichloro-5-methyl-1H-pyrrole-2-carboxamido)benzo[d]thiazole-6-carboxylate (99 mg, 0.236 mmol). The crude product was dispersed in acetonitrile, sonicated, heated, the precipitate filtered off and dried. Yield: 57 mg (59.4%); brown solid.

$^1$H NMR (400 MHz, DMSO-d$_6$) δ 2.29 (s, 3H), 7.78 (s, 1H), 8.00 (d, J=8.4 Hz, 1H), 12.16 (br s, 1H), 12.43 (s, 1H), 13.41 (br s, 1H).

HRMS (ESI$^-$) m/z for $C_{14}H_7Cl_3N_3O_3S$ ([M−H]$^-$): calculated 401.9268, found 401.9284.

HPLC: t$_r$ 8.937 min (96.1% at 220 nm, 97.8% at 254 nm), method A.

(Example 15) Synthesis of 2-(N-benzyl-4,5-dibromo-1H-pyrrole-2-carboxamido)benzo[d]thiazole-6-carboxylic acid

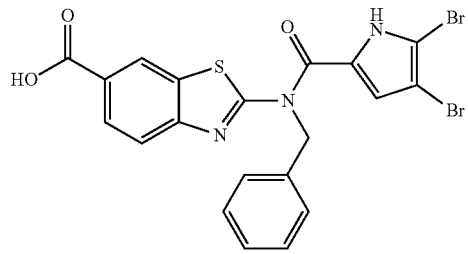 [SMILES: O=C(O)c1ccc2nc(N(Cc3ccccc3)C(=O)c3cc(Br)c(Br)[nH]3)sc2c1]

Exemplified Compound No. 15

Step 1: Synthesis of methyl 2-(N-benzyl-4,5-dibromo-1H-pyrrole-2-carboxamido)benzo[d]thiazole-6-carboxylate Methyl 2-(4,5-dibromo-1H-pyrrole-2-carboxamido)benzo[d]thiazole-6-carboxylate (500 mg, 1.09 mmol) synthesized in Step 1 of the Example 2 was dispersed in anhydrous N,N-dimethylformamide/acetone (4:1; 25 mL) under argon atmosphere, NaHCO$_3$ (277 mg, 3.27 mmol) and KI (553 mg, 3.27 mmol) were added and the mixture was stirred at 40° C. for 20 min. Benzyl bromide (0.16 mL, 1.30 mmol) was added portion wise over 5 hours and the reaction was stirred at 60° C. overnight. The solvent was removed in vacuo and 1 M HCl was added. The formed precipitate was filtered off, washed with water and dried. The crude product was purified with flash column chromatography using toluene/ethyl acetate/DMF (20:6:1) as an eluent. Obtained product was dispersed in diethyl ether and filtered out. Yield: 100 mg (16.7%); grey solid.

$^1$H NMR (400 MHz, DMSO-d$_6$) δ 3.86 (s, 3H), 5.89 (s, 2H), 7.07 (d, J=2.7 Hz, 1H), 7.21-7.43 (m, 5H), 7.68 (d, J=8.6 Hz, 1H), 8.01 (dd, J=8.6, 1.7 Hz, 1H), 8.54 (d, J=1.6 Hz, 1H), 12.93 (d, J=2.7 Hz, 1H).

$^{13}$C NMR (101 MHz, DMSO-d$_6$) δ 48.26, 52.37, 99.37, 106.99, 112.66, 116.90, 124.70, 125.16, 126.37, 127.49, 127.85, 128.38, 128.87, 131.39, 135.91, 140.05, 165.59, 166.04, 167.47.

Step 2: Synthesis of 2-(N-benzyl-4,5-dibromo-1H-pyrrole-2-carboxamido)benzo[d]thiazole-6-carboxylic acid Methyl 2-(N-benzyl-4,5-dibromo-1H-pyrrole-2-carboxamido)benzo[d]thiazole-6-carboxylate (80 mg, 0.15 mmol) was suspended in 1,4-dioxane (2 mL), 2 M NaOH (0.370 mL, 0.730 mmol) was added and the reaction mixture was stirred at 80° C. overnight. The reaction mixture was cooled down to room temperature, acidified using Amberlite IR120 ion exchange resin (pH<5) and stirred at room temperature for 5 min. The resin was filtered off and the filtrate was evaporated under reduced pressure. The crude product was dissolved in THF and the product was precipitated from diethyl ether and filtered off. The filtrate was concentrated and hexane was added to precipitate another portion of product. Yield. 49 mg, (62.9%); brown solid.

$^1$H NMR (400 MHz, DMSO-d$_6$) δ 5.89 (s, 2H), 7.07 (d, J=2.7 Hz, 1H), 7.21-7.45 (m, 5H), 7.66 (d, J=8.7 Hz, 1H), 7.99 (dd, J=8.6, 1.7 Hz, 1H), 8.50 (d, J=1.7 Hz, 1H), 12.92 (d, J=2.7 Hz, 1H), 13.05 (s, 1H).

$^{13}$C NMR (101 MHz, DMSO-d$_6$) δ 48.63, 99.80, 107.31, 112.92, 117.24, 125.07, 126.49, 126.77, 127.78, 128.31, 128.99, 129.27, 131.71, 136.15, 140.07, 166.44, 167.09, 167.85.

HRMS (ESI$^+$) m/z for C$_{20}$H$_{14}$Br$_2$N$_3$O$_3$S ([M+H]$^+$): calculated 533.9117, found 533.9100.

HPLC: t$_r$ 11.250 min (99.1% at 254 nm, 96.8% at 280 nm), method A.

(Example 16) Synthesis of 2-(N-benzyl-3,4-dichloro-5-methyl-1H-pyrrole-2-carboxamido)benzo[d]thiazole-6-carboxylic acid

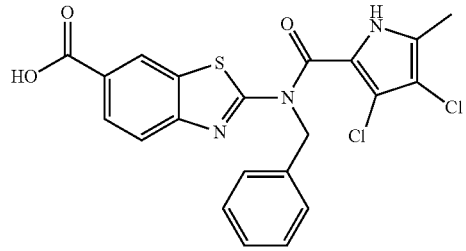 [SMILES: Cc1[nH]c(C(=O)N(Cc2ccccc2)c2nc3ccc(C(=O)O)cc3s2)c(Cl)c1Cl]

Exemplified Compound No. 16

Step 1: Synthesis of methyl 2-(N-benzyl-3,4-dichloro-5-methyl-1H-pyrrole-2-carboxamido)benzo[d]thiazole-6-carboxylate Methyl 2-(3,4-dichloro-5-methyl-1H-pyrrole-2-carboxamido)benzo[d]thiazole-6-carboxylate (400 mg, 1.04 mmol) obtained in Step 1 of the Example 1 was dissolved in anhydrous N,N-dimethylformamide (20 mL) under argon. NaHCO$_3$ (96 mg, 1.15 mmol) and KI (190 mg, 1.15 mmol) were added and the mixture was stirred at 40° C. for 20 min. Benzyl bromide (0.124 mL, 1.04 mmol) was added portion wise over 5 hours and reaction mixture was stirred at 40° C. overnight. To the reaction mixture water was added (25 mL) and the obtained precipitate was filtered out, washed with water and dried. The crude product was dispersed in acetonitrile, sonicated, filtered off as brown solid (400 mg, 81% yield) and was used in the next step without further purification.

$^1$H NMR (400 MHz, DMSO-d$_6$) δ 2.25 (s, 3H), 3.86 (s, 3H), 5.91 (s, 2H), 7.21-7.46 (m, 5H), 7.65 (d, J=8.7 Hz, 1H), 8.00 (dd, J=8.6, 1.7 Hz, 1H), 8.53 (d, J=1.7 Hz, 1H), 12.08 (s, 1H).

$^{13}$C NMR (101 MHz, DMSO-d$_6$) δ 10.97, 48.26, 52.31, 109.74, 112.55, 114.52, 121.93, 124.63, 125.07, 126.48, 127.40, 127.80, 128.29, 128.81, 129.35, 135.72, 139.97, 165.53, 165.72, 167.24.

Step 2: Synthesis of 2-(N-benzyl-3,4-dichloro-5-methyl-1H-pyrrole-2-carboxamido)benzo[d]thiazole-6-carboxylic acid The same operation as in Example 15 (Step 2) was performed using methyl 2-(N-benzyl-3,4-dichloro-5-methyl-1H-pyrrole-2-carboxamido)benzo[d]thiazole-6-carboxylate (100 mg, 0.210 mmol). The crude product was dispersed in acetonitrile, sonicated and filtered off. The solid was dissolved in N,N-dimethylformamide, precipitated from 1 M HCl, washed with water and acetone and dried. Yield: 37 mg (38.1%); off-white solid.

$^1$H NMR (400 MHz, DMSO-d$_6$) δ 2.25 (s, 3H), 5.92 (s, 2H), 7.20-7.48 (m, 5H), 7.63 (d, J=8.7 Hz, 1H), 7.99 (dd, J=8.6, 1.7 Hz, 1H), 8.49 (d, J=1.7 Hz, 1H), 12.08 (s, 1H), 13.06 (s, 1H).

$^{13}$C NMR (101 MHz, DMSO-d$_6$) δ 10.98, 48.26, 109.73, 112.45, 114.46, 121.98, 124.73, 126.28, 126.36, 127.42, 127.80, 128.47, 128.81, 129.31, 135.77, 139.68, 165.73, 166.59, 167.22.

HRMS (ESI⁻) m/z for $C_{21}H_{14}Cl_2N_3O_3S$ ([M−H]⁻): calculated 458.0138, found 458.0133.

HPLC: $t_r$ 11.263 min (97.2% at 254 nm, 96.3% at 280 nm), method A.

(Example 17) Synthesis of N-(6-(1H-tetrazol-5-yl)benzo[d]thiazol-2-yl)-3,4-dichloro-5-methyl-1H-pyrrole-2-carboxamide

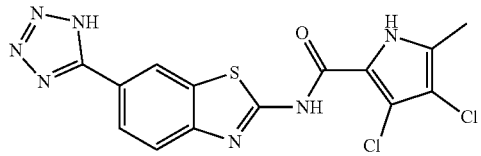 [SMILES: Cc1[nH]c(C(=O)Nc2nc3ccc(-c4nnn[nH]4)cc3s2)c(Cl)c1Cl]

Exemplified Compound No. 17

Step 1: Synthesis of 2-aminobenzo[d]thiazole-6-carbonitrile

The same operation as in Example 5 (Step 3) was performed using 4-aminobenzonitrile (1.00 g, 8.46 mmol). After neutralisation with 25% aqueous $NH_3$ solution, the product was extracted to ethyl acetate and the organic layer was washed with 10% aqueous $Na_2S_2O_3$, solution, saturated aqueous $NaHCO_3$ solution and brine, dried over $Na_2SO_4$ and concentrated under reduced pressure. The residue was purified with flash column chromatography using hexane/ethyl acetate/THF (1:1:1) as an eluent. Yield: 580 mg (39.1%); white solid.

¹H NMR (400 MHz, DMSO-$d_6$) δ 7.41 (dd, J=8.4, 0.6 Hz, 1H), 7.60 (dd, J=8.4, 1.8 Hz, 1H), 8.05 (s, 2H), 8.18 (dd, J=1.8, 0.5 Hz, 1H).

Step 2: Synthesis of 3,4-dichloro-N-(6-cyanobenzo[d]thiazol-2-yl)-5-methyl-1H-pyrrole-2-carboxamide The same operation as in Example 1 (Step 1) was performed using 2-aminobenzo[d]thiazole-6-carbonitrile (400 mg, 2.28 mmol). The crude product was dispersed in acetonitrile, sonicated, filtered off and dried. Yield: 310 mg (38.7%); grey solid.

¹H NMR (400 MHz, DMSO-$d_6$) δ 2.27 (s, 3H), 7.78-8.00 (m, 2H), 8.59 (s, 1H), 12.06 (s, 1H), 12.39 (s, 1H).

HRMS (ESI⁺) m/z for $C_{14}H_9Cl_2N_4OS$ ([M+H]⁺): calculated 350.9869, found 350.9859.

HPLC: $t_r$ 10.557 min (98.7% at 254 nm, 98.9% at 280 nm), method A.

Step 3: Synthesis of N-(6-(1H-tetrazol-5-yl)benzo[d]thiazol-2-yl)-3,4-dichloro-5-methyl-1H-pyrrole-2-carboxamide A solution of 3,4-dichloro-N-(6-cyanobenzo[d]thiazol-2-yl)-5-methyl-1H-pyrrole-2-carboxamide (100 mg, 0.285 mmol), ammonium chloride (152 mg, 2.85 mmol) and sodium azide (185 mg, 2.85 mmol) in DMF (5 mL) was heated at 100° C. for 15 h. The mixture was cooled down to rt, water (7 mL) and ethyl acetate (7 mL) were added, and the mixture was acidified with 1M HCl to pH 3-4. The precipitate was filtered off, washed with ethyl acetate and dried. The crude product was dispersed in acetone (5 mL), sonicated, filtered off and dried. Yield: 67 mg (59.7%); brown solid.

¹H NMR (400 MHz, DMSO-$d_6$) δ 2.29 (s, 3H), 7.95 (s, 1H), 8.08-8.18 (m, 1H), 8.70 (s, 1H), 12.00 (s, 1H), 12.41 (s, 1H), the signal for the tetrazole NH not seen.

HRMS (ESI⁺) m/z for $C_{14}H_{10}Cl_2N_7OS$ ([M+H]⁺): calculated 394.0039, found 394.0039.

HPLC: $t_r$ 7.660 min (95.3% at 254 nm, 95.3% at 280 nm), method A.

(Example 18) Synthesis of 2-(3,4-dichloro-5-methyl-1H-pyrrole-2-carboxamido)benzo[d]thiazole-6-carboxamide

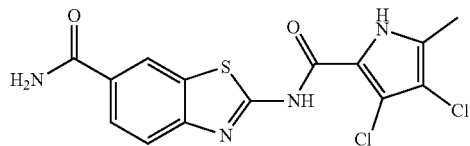 [SMILES: Cc1[nH]c(C(=O)Nc2nc3ccc(C(N)=O)cc3s2)c(Cl)c1Cl]

Exemplified Compound No. 18

Step 1: Synthesis of 2-(3,4-dichloro-5-methyl-1H-pyrrole-2-carboxamido)benzo[d]thiazole-6-carboxamide Methyl 2-(3,4-dichloro-5-methyl-1H-pyrrole-2-carboxamido)benzo[d]thiazole-6-carboxylate (100 mg, 0.28 mmol) synthesized in Step 1 of the Example 1 was dissolved in N-methyl-2-pyrrolidone (10 mL), pulverized KOH (320 mg, 5.96 mmol) was added and the reaction mixture was stirred at 100° C. overnight. Additional 10 equivalents of KOH (160 mg, 2.8 mmol) were added and the reaction mixture was stirred at 115° C. overnight. The reaction mixture was cooled down to room temperature, diluted with water and acidified with 2M HCl. Resulting precipitate was filtered off and purified with flash column chromatography using hexane/ethyl acetate/THF (1:1:1)→ethyl acetate/THF (1:1) as an eluent. Yield: 10 mg, (10.4%); white solid.

¹H NMR (400 MHz, DMSO-$d_6$) δ 2.27 (s, 3H), 7.40 (s, 1H), 7.76 (d, J=8.5 Hz, 1H), 7.96 (d, J=8.1 Hz, 1H), 8.04 (s, 1H), 8.49 (s, 1H), 11.99 (s, 1H), 12.52 (s, 1H).

HRMS (ESI⁻) m/z for $C_{14}H9Cl_2N_4O_2S$ ([M−H]⁻): calculated 366.9829, found 366.9822.

HPLC: $t_r$ 6.397 min (98.2% at 254 nm, 98.4% at 280 nm), method A.

(Example 19). Synthesis of 2-(4,5-dibromo-1H-pyrrole-2-carboxamido)-N-hydroxybenzo[d]thiazole-6-carboxamide

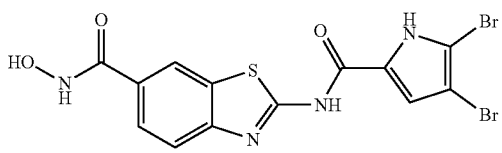 [SMILES: O=C(NO)c1ccc2nc(NC(=O)c3cc(Br)c(Br)[nH]3)sc2c1]

Exemplified Compound No. 19

Step 1: Synthesis of 2-(4,5-dibromo-1H-pyrrole-2-carboxamido)-N-((tetrahydro-2H-pyran-2-yl)oxy)benzo[d]thiazole-6-carboxamide A solution of 2-(4,5-dibromo-1H-pyrrole-2-carboxamido)benzo[d]thiazole-6-carboxylic acid (Example 2) (100 mg, 0.225 mmol) in N,N-dimethylformamide (3 mL) was cooled to 0° C. and then EDC (42 mg, 0.27 mmol) and HOBt (40 mg, 0.295 mmol) were added. pH was adjusted to 8 with N-methylmorpholine and the reaction mixture stirred for 20 min at 0° C. Then O-(tetrahydro-2H-pyran-2-yl)hydroxylamine (26 mg, 0.225 mmol) was added and reaction mixture stirred overnight at room temperature. The solvent was evaporated in vacuo and the residue dissolved in ethyl acetate (30 mL) and washed successively with 1% citric acid (15 mL), saturated aqueous NaHCO$_3$ solution (15 mL), and brine (30 mL). The organic phase was dried over Na$_2$SO$_4$, filtered and solvent evaporated under reduced pressure. Crude product was purified using flash column chromatography using dichloromethane/methanol (20:1) as eluent. Yield: 8.7 mg (7.0%); beige solid.

$^1$H NMR (400 MHz, DMSO-d$_6$) δ 1.57 (s, 3H), 1.74 (s, 3H), 3.50-3.59 (m, 1H), 4.01-4.15 (m, 1H), 5.03 (s, 1H), 7.55 (d, J=2.7 Hz, 1H), 7.79-7.89 (m, 2H), 8.42 (d, J=1.6 Hz, 1H), 11.69 (s, 1H), 12.79 (s, 1H), 13.28 (s, 1H).

Step 2: Synthesis of 2-(4,5-dibromo-1H-pyrrole-2-carboxamido)-N-hydroxybenzo[d]thiazole-6-carboxamide A solution of 2-(4,5-dibromo-1H-pyrrole-2-carboxamido)-N-((tetrahydro-2H-pyran-2-yl)oxy)benzo[d]thiazole-6-carboxamide (8.7 mg, 0.016 mmol) in dichloromethane (5 mL) and CF$_3$COOH (0.012 mL, 0.161 mmol) was stirred at room temperature for 2 h. The precipitate was filtered off, washed with dichloromethane and dried. Yield: 1.7 mg (23%); white solid.

$^1$H NMR (400 MHz, DMSO-d$_6$) δ 7.55 (s, 1H), 7.76-7.90 (m, 2H), 8.40 (s, 1H), 11.27 (s, 1H), 12.78 (s, 1H), 13.28 (s, 1H).

HRMS (ESI$^+$) m/z for C$_{13}$H9Br$_2$N$_4$O$_3$S ([M+H]$^+$): calculated 458.87566, found 458.87604.

HPLC: t$_r$ 4.94 min (96.8% at 254 nm, 96.6% at 280 nm), method A.

(Example 20). Synthesis of 2-(3,4-dichloro-5-methyl-1H-pyrrole-2-carboxamido)-N-hydroxybenzo[d]thiazole-6-carboxamide

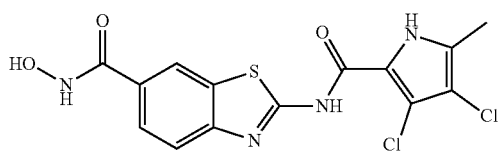 [SMILES: Cc1[nH]c(C(=O)Nc2nc3ccc(C(=O)NO)cc3s2)c(Cl)c1Cl]

Exemplified Compound No. 20

Step 1: Synthesis of 2-(3,4-dichloro-5-methyl-1H-pyrrole-2-carboxamido)-N-((tetrahydro-2H-pyran-2-yl)oxy)benzo[d]thiazole-6-carboxamide The same operation as in Example 19 (Step 1) was performed using 2-(3,4-dichloro-5-methyl-1H-pyrrole-2-carboxamido)benzo[d]thiazole-6-carboxylic acid (Example 1) (0.150 g, 0.41 mmol). Yield: 70 mg (36.8%); off-white solid.

$^1$H NMR (400 MHz, DMSO-d$_6$) δ 1.56 (s, 3H), 1.74 (s, 3H), 2.24 (d, J=2.2 Hz, 3H), 3.50-3.58 (m, 1H), 4.03-4.13 (m, 1H), 5.01 (s, 1H), 7.63 (d, J=9.5 Hz, 1H), 7.72-7.80 (m, 1H), 8.26 (d, J=8.6 Hz, 1H), 11.61 (s, 1H).

Step 2: Synthesis of 2-(3,4-dichloro-5-methyl-1H-pyrrole-2-carboxamido)-N-hydroxybenzo[d]thiazole-6-carboxamide The same operation as in Example 19 (Step 2) was performed using 2-(3,4-dichloro-5-methyl-1H-pyrrole-2-carboxamido)-N-((tetrahydro-2H-pyran-2-yl)oxy)benzo[d]thiazole-6-carboxamide (0.070 g, 0.15 mmol). Yield: 23 mg (40.0%); brown solid.

$^1$H NMR (400 MHz, DMSO-d$_6$) δ 2.28 (s, 3H), 7.78 (d, J=8.6 Hz, 1H), 7.85 (dd, J=8.4, 1.7 Hz, 1H), 8.39 (d, J=1.6 Hz, 1H), 11.27 (s, 1H), 11.92 (s, 1H), 12.40 (s, 1H).

HRMS (ESI$^-$) m/z for C$_{14}$H9Cl$_2$N$_4$O$_3$S ([M–H]$^-$): calculated 382.97669, found 382.97842.

HPLC: t$_r$ 5.57 min (98.0% at 254 nm, 98.1% at 280 nm), method A.

(Example 21) Synthesis of 3-(2-(4,5-dibromo-1H-pyrrole-2-carboxamido)benzo[d]thiazole-6-carboxamido)propanoic acid

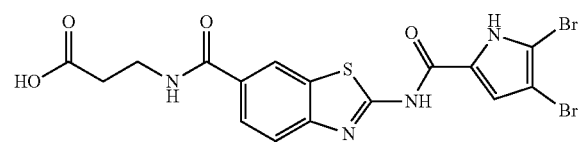 [SMILES: O=C(O)CCNC(=O)c1ccc2nc(NC(=O)c3cc(Br)c(Br)[nH]3)sc2c1]

Exemplified Compound No. 21

Step 1: Synthesis of ethyl 3-(2-(4,5-dibromo-1H-pyrrole-2-carboxamido)benzo[d]thiazole-6-carboxamido)propanoate A solution of 2-(4,5-dibromo-1H-pyrrole-2-carboxamido)benzo[d]thiazole-6-carboxylic acid (Example 2) (200 mg, 0.45 mmol) in N,N-dimethylformamide (7.5 mL) was cooled to 0° C. and then EDC (84 mg, 0.54 mmol), HOBt (89 mg, 0.585 mmol) and N-methylmorpholine (99 μL, 0.9 mmol) were added and the reaction mixture stirred for 20 min at 0° C. Then 3-alanine ethyl ester (75 mg, 0.49 mmol) was added and reaction mixture stirred overnight at room temperature. The solvent was evaporated in vacuo, to the residue ethyl acetate (30 mL) and 10% citric acid (15 mL) were added after which the precipitate formed. The solid was filtered off and dried. Yield: 134 mg (54.9%); brown solid.

$^1$H NMR (400 MHz, DMSO-d$_6$) δ 1.19 (t, J=7.1 Hz, 3H), 2.60 (t, J=7.0 Hz, 2H), 3.52 (q, J=7.0 Hz, 2H), 4.09 (q, J=7.1 Hz, 2H), 7.14 (s, 1H), 7.73 (d, J=8.4 Hz, 1H), 7.88 (dd, J=8.4, 1.7 Hz, 1H), 8.41 (d, J=1.4 Hz, 1H), 8.58 (t, J=5.3 Hz, 1H), 12.78 (br s, 1H), 13.28 (s, 1H).

Step 2: Synthesis of 3-(2-(4,5-dibromo-1H-pyrrole-2-carboxamido)benzo[d]thiazole-6-carboxamido)propanoic acid Ethyl 3-(2-(4,5-dibromo-1H-pyrrole-2-carboxamido)benzo[d]thiazole-6-carboxamido)propanoate (100 mg, 0.189 mmol) was suspended in 1,4-dioxane (10 mL), 1 M NaOH (0.566 mL, 0.566 mmol) was added and the reaction mixture was stirred at room temperature overnight. The solvent was removed under reduced pressure, the residue was acidified with 1M HCl to pH=1 and the obtained precipitate was filtered off, washed with water and dried. Yield: 68 mg (70%); dark brown solid.

$^1$H NMR (400 MHz, DMSO-$d_6$) δ 2.56 (d, J=6.8 Hz, 2H), 3.50 (q, J=6.0 Hz, 2H), 7.54 (d, J=2.0 Hz, 1H), 7.80 (d, J=8.5 Hz, 1H), 7.94 (d, J=8.1 Hz, 1H), 8.49 (s, 1H), 8.61 (t, J=5.0 Hz, 1H), 12.79 (s, 1H), 13.28 (s, 1H).

HRMS (ESI$^-$) m/z for $C_{1-6}H_{11}Br_2N_4O_4S$ ([M–H]$^-$): calculated 512.8873, found 512.8875.

(Example 22) Synthesis of 3-(2-(3,4-dichloro-5-methyl-1H-pyrrole-2-carboxamido)benzo[d]thiazole-6-carboxamido)propanoic acid

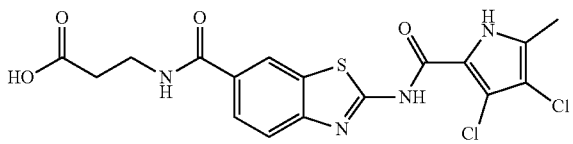 [SMILES: Cc1[nH]c(C(=O)Nc2nc3ccc(C(=O)NCCC(=O)O)cc3s2)c(Cl)c1Cl]

Exemplified Compound No. 22

Step 1: Synthesis of ethyl 3-(2-(3,4-dichloro-5-methyl-1H-pyrrole-2-carboxamido)benzo[d]thiazole-6-carboxamido)propanoate The same operation as in Example 21 (Step 1) was performed using 3,4-dichloro-5-methyl-1H-pyrrole-2-carboxamido)benzo[d]thiazole-6-carboxylic acid (Example 1) (80 mg, 0.22 mmol). Yield: 47 mg (45.5%); light brown solid.

$^1$H NMR (400 MHz, DMSO-$d_6$) δ 1.19 (t, J=7.0 Hz, 3H), 2.28 (s, 3H), 2.61 (t, J=6.9 Hz, 2H), 3.53 (q, J=5.7 Hz, 2H), 4.09 (q, J=7.2 Hz, 2H), 7.79 (s, 1H), 7.93 (d, J=8.5 Hz, 1H), 8.46 (s, 1H), 8.63 (t, J=4.6 Hz, 1H), 11.92 (s, 1H), 12.34 (s, 1H).

Step 2: Synthesis of 3-(2-(3,4-dichloro-5-methyl-1H-pyrrole-2-carboxamido)benzo[d]thiazole-6-carboxamido)propanoic acid The same operation as in Example 21 (Step 2) was performed using ethyl 3-(2-(3,4-dichloro-5-methyl-1H-pyrrole-2-carboxamido)benzo[d]thiazole-6-carboxamido)propanoate (33 mg, 0.070 mmol); Yield: 30 mg (95.7%); brown solid.

$^1$H NMR (400 MHz, DMSO-$d_6$) δ 2.28 (s, 3H), 2.55 (t, J=7.5 Hz, 2H), 3.49 (q, J=7.0, Hz, 2H), 7.78 (d, J=8.4 Hz, 1H), 7.93 (dd, J=8.5, 1.8 Hz, 1H), 8.47 (d, J=1.2 Hz, 1H), 8.61 (t, J=5.5 Hz, 1H), 12.43 (s, 1H).

HRMS (ESI$^-$) m/z for $C_{17}H_{13}Cl_2N_4O_4S$ ([M–H]$^-$): calculated 439.0040, found 439.0043.

HPLC: $t_r$ 6.283 min (95.2% at 254 nm, 95.3% at 280 nm), method A.

(Example 23) Synthesis of (2-(3,4-dichloro-5-methyl-1H-pyrrole-2-carboxamido)benzo[d]thiazole-6-carbonyl)glycine

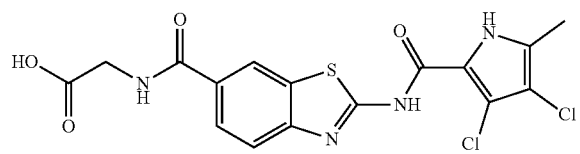 [SMILES: Cc1[nH]c(C(=O)Nc2nc3ccc(C(=O)NCC(=O)O)cc3s2)c(Cl)c1Cl]

Exemplified Compound No. 23

Step 1: Synthesis of methyl (2-(3,4-dichloro-5-methyl-1H-pyrrole-2-carboxamido)benzo[d]thiazole-6-carbonyl)glycinate The same operation as in Example 21 (Step 1) was performed using 3,4-dichloro-5-methyl-1H-pyrrole-2-carboxamido)benzo[d]thiazole-6-carboxylic acid (Example 1) (40 mg, 0.108 mmol) and glycine methyl ester (28 mg, 0.119 mmol). Yield: 39 mg (81.7%); light brown crystals.

$^1$H NMR (400 MHz, DMSO-$d_6$) δ 2.29 (s, 3H), 3.68 (s, 3H), 4.06 (d, J=5.8 Hz, 2H), 7.83 (s, 1H), 7.97 (dd, J=9.0, 1.2 Hz, 1H), 8.51 (s, 1H), 9.04 (t, J=6.2 Hz, 1H), 11.95 (s, 1H), 12.35 (s, 1H).

Step 2: Synthesis of (2-(3,4-dichloro-5-methyl-1H-pyrrole-2-carboxamido)benzo[d]thiazole-6-carbonyl)glycine The same operation as in Example 21 (Step 2) was performed using methyl (2-(3,4-dichloro-5-methyl-1H-pyrrole-2-carboxamido)benzo[d]thiazole-6-carbonyl)glycinate (28 mg, 0.063 mmol); Yield: 21 mg (77.8%); light brown crystals.

$^1$H NMR (400 MHz, DMSO-$d_6$) δ 2.28 (s, 3H), 3.96 (d, J=5.6 Hz, 2H), 7.81 (d, J=8.8 Hz, 1H), 7.97 (d, J=8.1 Hz, 1H), 8.51 (s, 1H), 8.98 (m, 1H), 11.99 (s, 1H), 12.40 (s, 1H).

HRMS (ESI$^-$) m/z for $C_{1-6}H_{11}Cl_2N_4O_4S$ ([M–H]$^-$): calculated 424.9884, found 424.9890.

(Example 24) Synthesis of 4-((3-carboxybenzyl)oxy)-2-(3,4-dichloro-5-methyl-1H-pyrrole-2-carboxamido)benzo[d]thiazole-6-carboxylic acid

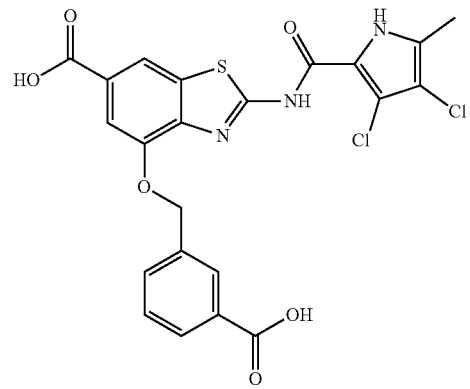 [SMILES: Cc1[nH]c(C(=O)Nc2nc3c(OCc4cccc(C(=O)O)c4)cc(C(=O)O)cc3s2)c(Cl)c1Cl]

Exemplified Compound No. 24

Step 1: Synthesis of methyl 3-((3-(methoxycarbonyl)benzyl)oxy)-4-nitrobenzoate

The same operation as in Example 9 (Step 1) was performed using methyl 3-(bromomethyl)benzoate (349 mg, 1.52 mmol). Yield: 422 mg (96.4%); yellow crystals.

$^1$H NMR (400 MHz, DMSO-$d_6$) δ 3.87 (s, 3H), 3.91 (s, 3H), 5.50 (s, 2H), 7.59 (t, J=7.7 Hz, 1H), 7.71 (dd, J=8.4, 1.6 Hz, 1H), 7.74 (dt, J=7.8, 1.5 Hz, 1H), 7.92 (d, J=1.6 Hz, 1H), 7.95 (dt, J=7.7, 1.5 Hz, 1H), 8.05 (d, J=8.4 Hz, 1H), 8.10 (t, J=1.7 Hz, 1H).

Step 2: Synthesis of methyl 4-amino-3-((3-(methoxycarbonyl)benzyl)oxy)benzoate

The same operation as in Example 9 (Step 2) was performed using methyl 3-((3-(methoxycarbonyl)benzyl)oxy)-4-nitrobenzoate (333 mg, 0.964 mmol). Yield: 200 mg (65.8%); pale yellow crystals.

$^1$H NMR (400 MHz, DMSO-$d_6$) δ 3.75 (s, 3H), 3.87 (s, 3H), 5.24 (s, 2H), 5.71 (s, 2H), 6.69 (d, J=8.7 Hz, 1H), 7.40-7.42 (m, 2H), 7.57 (t, J=7.7 Hz, 1H), 7.81-7.86 (m, 1H), 7.91-7.95 (m, 1H), 8.08-8.09 (m, 1H).

Step 3: Synthesis of methyl 2-amino-4-((3-(methoxycarbonyl)benzyl)oxy)benzo[d]thiazole-6-carboxylate The same operation as in Example 5 (Step 3) was performed using methyl 4-amino-3-((3-(methoxycarbonyl)benzyl)oxy)benzoate (197 mg, 0.625 mmol). After neutralisation with 25% aqueous NH$_3$ solution and filtration of the precipitate, the crude product was purified with flash column chromatography using ethyl acetate/hexane (1:1) as eluent. Yield: 81 mg (34.8%); white crystals.

$^1$H NMR (400 MHz, DMSO-$d_6$) δ 3.83 (s, 3H), 3.88 (s, 3H), 5.33 (s, 2H), 7.47 (d, J=1.5 Hz, 1H), 7.58 (t, J=8.0 Hz, 1H), 7.79 (dt, J=7.7, 1.4 Hz, 1H), 7.90-7.97 (m, 3H), 7.99 (d, J=1.5 Hz, 1H), 8.09-8.11 (m, 1H).

Step 4: Synthesis of methyl 2-(3,4-dichloro-5-methyl-1H-pyrrole-2-carboxamido)-4-((3-(methoxycarbonyl)benzyl)oxy)benzo[d]thiazole-6-carboxylate The same operation as in Example 1 (Step 1) was performed using methyl 2-amino-4-((3-(methoxycarbonyl)benzyl)oxy)benzo[d]thiazole-6-carboxylate (77 mg, 0.207 mmol). Yield: 73 mg (64.4%); light grey solid.

$^1$H NMR (400 MHz, DMSO-$d_6$) δ 2.27 (s, 3H), 3.88 (s, 3H), 3.89 (s, 3H), 5.43 (s, 2H), 7.61 (s, 1H), 7.63-7.65 (m, 1H), 7.83 (s, 1H), 7.98 (dt, J=7.7, 1.5 Hz, 1H), 8.14-8.17 (m, 1H), 8.32 (d, J=0.9 Hz, 1H), 12.21 (s, 1H), 12.25 (s, 1H).

Step 5: Synthesis of 4-((3-carboxybenzyl)oxy)-2-(3,4-dichloro-5-methyl-1H-pyrrole-2-carboxamido)benzo[d]thiazole-6-carboxylic acid To a suspension of methyl 2-(3,4-dichloro-5-methyl-1H-pyrrole-2-carboxamido)-4-((3-(methoxycarbonyl)benzyl)oxy)benzo[d]thiazole-6-carboxylate (60 mg, 0.109 mmol) in 1,4-dioxane 2M NaOH (274 μL, 0.547 mmol) was added and the suspension stirred at 60° C. overnight. 5 equivalents of 2M NaOH were added and the reaction mixture was stirred at 75° C. for 7 days. Reaction was followed with HPLC-MS and 5 equivalents of fresh 2M NaOH were added and the reaction mixture stirred at 75° C. for 7 days. After the reaction was finished, the solvent was evaporated under reduced pressure, the residue was acidified with 1 M HCl to pH=1 and the obtained precipitate was filtered off. The crude product was suspended in methanol, heated and filtered off. Yield: 33 mg (58.5%); brown solid.

$^1$H NMR (400 MHz, DMSO-$d_6$) δ 2.26 (s, 3H), 5.41 (s, 2H), 7.58 (t, J=7.7 Hz, 1H), 7.63 (d, J=1.4 Hz, 1H), 7.80 (dt, J=7.8, 1.4 Hz, 1H), 7.96 (dt, J=7.8, 1.4 Hz, 1H), 8.12 (d, J=1.8 Hz, 1H), 8.27 (d, J=1.4 Hz, 1H), 12.19 (br s, 1H), 12.25 (s, 1H), 13.06 (br s, 2H).

HRMS (ESI$^+$) m/z for $C_{22}H_{16}Cl_2N_3O_6S$ ([M+H]$^+$): calculated 520.0131, found 520.0146.

HPLC: $t_r$ 8.323 min (95.8% at 254 nm, 95.3% at 280 nm), method A.

(Example 25) Synthesis of 4-(2-((6-((cyanomethyl)carbamoyl)-2-(3,4-dichloro-5-methyl-1H-pyrrole-2-carboxamido)benzo[d]thiazol-4-yl)oxy)ethyl)morpholin-4-ium chloride

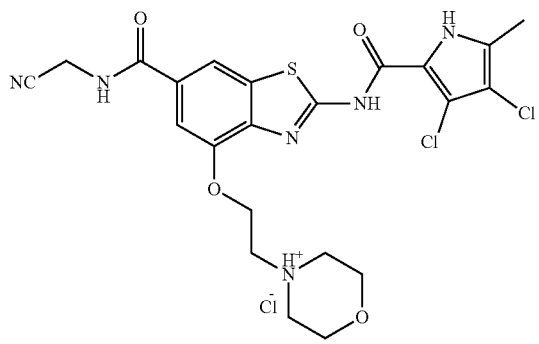

Exemplified Compound No. 25

Step 1: Synthesis of 4-(2-((6-((cyanomethyl)carbamoyl)-2-(3,4-dichloro-5-methyl-1H-pyrrole-2-carboxamido)benzo[d]thiazol-4-yl)oxy)ethyl)morpholin-4-ium chloride A solution of 4-(2-((6-carboxy-2-(3,4-dichloro-5-methyl-1H-pyrrole-2-carboxamido)benzo[d]thiazol-4-yl)oxy)ethyl)morpholin-4-ium chloride (Example 10) (19 mg, 0.035 mmol) in N,N-dimethylformamide (4 mL) was cooled to 0° C. and then EDC (8 mg, 0.042 mmol), HOBt (6 mg, 0.046 mmol) and N-methylmorpholine (12 μL, 0.106 mmol) were added and the reaction mixture stirred for 20 min at 0° C. Then aminoacetonitrile hydrochloride (5 mg, 0.053 mmol) was added and reaction mixture stirred overnight at room temperature. The solvent was evaporated in vacuo, to the residue ethyl acetate (10 mL) and 1M HCl (10 mL) were added after which the precipitate formed. The solid was filtered off and dried. Yield: 14 mg (68.0%); beige solid.

$^1$H NMR (400 MHz, DMSO-$d_6$) δ 2.29 (s, 3H), 3.25-3.34 (m, 2H), 3.62-3.73 (m, 4H), 3.76-3.88 (m, 2H), 4.01-4.10 (m, 2H), 4.36 (d, J=5.4 Hz, 2H), 4.71 (t, 2H), 7.62 (d, J=1.5 Hz, 1H), 8.21 (d, J=0.5 Hz, 1H), 9.40 (t, J=5.5 Hz, 1H), 10.93 (s, 1H), 12.20 (s, 1H), 12.78 (s, 1H).

HRMS (ESI$^+$) m/z for $C_{22}H_{23}Cl_2N_6O_4S$ ([M+H]$^+$): calculated 537.0873, found 537.0861.

HPLC: $t_r$ 4.313 min (96.9% at 254 nm, 97.7% at 280 nm), method A.

(Example 26) Synthesis of N-(cyanomethyl)-2-(3,4-dichloro-5-methyl-1H-pyrrole-2-carboxamido)benzo[d]thiazole-6-carboxamide

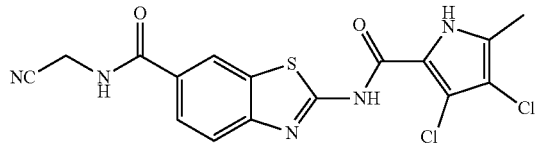 [SMILES: Cc1[nH]c(C(=O)Nc2nc3ccc(C(=O)NCC#N)cc3s2)c(Cl)c1Cl]

Exemplified Compound No. 26

Step 1: Synthesis of methyl (2-(3,4-dichloro-5-methyl-1H-pyrrole-2-carboxamido)benzo[d]thiazole-6-carbonyl)glycinate The same operation as in Example 25 (Step 1) was performed using 3,4-dichloro-5-methyl-1H-pyrrole-2-carboxamido)benzo[d]thiazole-6-carboxylic acid (Example 1) (60 mg, 0.162 mmol). Yield: 45 mg (68.0%); grey solid.

$^1$H NMR (400 MHz, DMSO-$d_6$) δ 2.28 (s, 3H), 4.35 (d, J=5.4 Hz, 2H), 7.83 (s, 1H), 7.95 (dd, J=8.5, 1.8 Hz, 1H), 8.52 (s, 1H), 9.27 (t, J=5.5 Hz, 1H), 11.97 (s, 1H), 12.34 (s, 1H).

HRMS (ESI$^+$) m/z for $C_{16}H_{12}Cl_2N_5O_2S$ ([M+H]$^+$): calculated 408.0083, found 408.0082.

HPLC: $t_r$ 7.870 min (97.3% at 254 nm, 97.2% at 280 nm), method A.

(Example 27) Synthesis of 4-(benzyloxy)-N-(cyanomethyl)-2-(3,4-dichloro-5-methyl-1H-pyrrole-2-carboxamido)benzo[d]thiazole-6-carboxamide

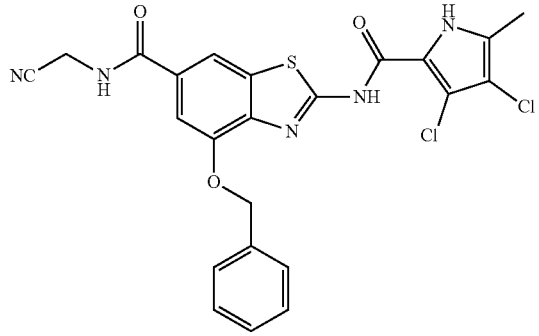 [SMILES: Cc1[nH]c(C(=O)Nc2nc3c(OCc4ccccc4)cc(C(=O)NCC#N)cc3s2)c(Cl)c1Cl]

Exemplified Compound No. 27

Step 1: Synthesis of 2-amino-4-(benzyloxy)benzo[d]thiazole-6-carboxylic acid

To a suspension of methyl 2-amino-4-(benzyloxy)benzo[d]thiazole-6-carboxylate (400 mg, 1.27 mmol) synthesized in Step 3 of the Example 4 in methanol (30 mL) 1M NaOH (6.35 mL, 6.35 mmol) was added and the reaction mixture stirred at 80° C. overnight. The solvent was removed under reduced pressure, the residue acidified with 1M HCl to pH=2 and cooled at 0° C. for 3 h. The white precipitate was filtered off. Yield: 340 mg (89.0%); white solid.

$^1$H NMR (400 MHz, DMSO-$d_6$) δ 5.23 (s, 2H), 7.31-7.43 (m, 3H), 7.45 (d, J=1.5 Hz, 1H), 7.47-7.51 (m, 2H), 7.88 (s, 2H), 7.93 (d, J=1.5 Hz, 1H), 12.68 (s, 1H).

Step 2: Synthesis of 2-amino-4-(benzyloxy)-N-(cyanomethyl)benzo[d]thiazole-6-carboxamide The same operation as in Example 25 (Step 1) was performed using 2-amino-4-(benzyloxy)benzo[d]thiazole-6-carboxylic acid (330 mg, 1.10 mmol) obtained in Step 1 above. Yield: 93 mg (27%); white solid.

$^1$H NMR (400 MHz, DMSO-$d_6$) δ 4.32 (d, J=5.4 Hz, 2H), 5.24 (s, 2H), 7.33-7.38 (m, 1H), 7.39-7.45 (m, 2H), 7.47 (d, J=1.6 Hz, 1H), 7.48-7.52 (m, 2H), 7.83 (s, 2H), 7.86 (d, J=1.6 Hz, 1H), 9.08 (t, J=5.5 Hz, 1H).

Step 3: Synthesis of 4-(benzyloxy)-N-(cyanomethyl)-2-(3,4-dichloro-5-methyl-1H-pyrrole-2-carboxamido)benzo[d]thiazole-6-carboxamide The same operation as in Example 1 (Step 1) was performed using 2-amino-4-(benzyloxy)-N-(cyanomethyl)benzo[d]thiazole-6-carboxamide (77 mg, 0.228 mmol). Yield: 45 mg (38.5%); brown solid.

$^1$H NMR (400 MHz, DMSO-$d_6$) δ 2.26 (s, 3H), 4.37 (d, J=5.4 Hz, 2H), 5.32 (s, 2H), 7.36-7.48 (m, 3H), 7.51-7.59 (m, 2H), 7.63 (d, J=1.3 Hz, 1H), 8.15 (d, J=1.3 Hz, 1H), 9.28 (t, J=5.5 Hz, 1H), 12.18 (br s, 1H), 12.22 (s, 1H).

HRMS (ESI$^-$) m/z for $C_{23}H_{16}Cl_2N_5O_3S$ ([M–H]$^-$): calculated 512.0356, found 512.0361.

HPLC: $t_r$ 11.253 min (95.2% at 254 nm, 95.2% at 280 nm), method A.

(Example 28) Synthesis of 4-(benzyloxy)-2-(3,4-dichloro-5-methyl-1H-pyrrole-2-carboxamido)benzo[d]thiazole-6-carboxamide

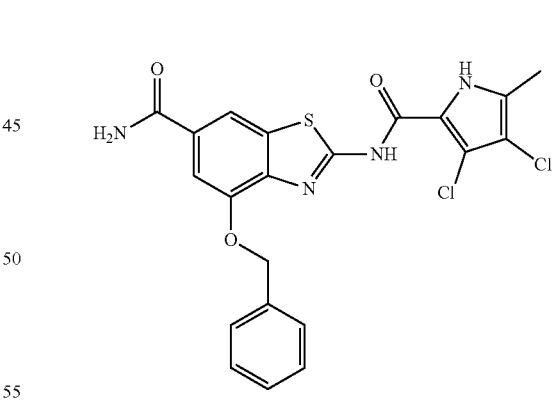

Exemplified Compound No. 28

Step 1: Synthesis of 3-(benzyloxy)-4-nitrobenzamide

A solution of methyl 3-(benzyloxy)-4-nitrobenzoate (1.19 g, 4.15 mmol) synthesized in Step 1 of the Example 9 in saturated methanol solution of ammonia was stirred in a pressure tube at 65° C. overnight. The formed precipitate was filtered off. Mother liquid was evaporated under reduced pressure, the residue crystallized from acetonitrile and the crystals combined with the filtered precipitate. Yield: 1.01 g (89.4%); pale yellow crystals.

¹H NMR (400 MHz, DMSO-$d_6$) δ 5.37 (s, 2H), 7.33-7.49 (m, 5H), 7.59 (dd, J=8.4, 1.6 Hz, 1H), 7.73 (s, 1H), 7.87 (d, J=1.5 Hz, 1H), 7.98 (d, J=8.4 Hz, 1H), 8.24 (s, 1H).

Step 2: Synthesis of 4-amino-3-(benzyloxy)benzamide

The same operation as in Example 9 (Step 2) was performed using 3-(benzyloxy)-4-nitrobenzamide (300 mg, 1.102 mmol). Yield: 260 mg (97.4%); yellow oil.

¹H NMR (400 MHz, DMSO-$d_6$) δ 5.14 (s, 2H), 5.29 (s, 2H), 6.63 (d, J=8.2 Hz, 1H), 6.92 (s, 1H), 7.28-7.36 (m, 3H), 7.36-7.44 (m, 2H), 7.45 (d, J=1.8 Hz, 1H), 7.48-7.55 (m, 2H), 7.60 (s, 1H).

Step 3: Synthesis of 2-amino-4-(benzyloxy)benzo[d]thiazole-6-carboxamide

The same operation as in Example 5 (Step 3) was performed using 4-amino-3-(benzyloxy)benzamide (255 mg, 1.053 mmol). Yield: 307 mg (97.0%); orange solid.

¹H NMR (400 MHz, DMSO-$d_6$) δ 5.22 (s, 2H), 7.23 (s, 1H), 7.32-7.37 (m, 1H), 7.38-7.44 (m, 2H), 7.45-7.51 (m, 3H), 7.74 (s, 2H), 7.83 (d, J=1.5 Hz, 1H), 7.86 (s, 1H).

Step 4: Synthesis of 4-(benzyloxy)-2-(3,4-dichloro-5-methyl-1H-pyrrole-2-carboxamido)benzo[d]thiazole-6-carboxamide The same operation as in Example 1 (Step 1) was performed using 2-amino-4-(benzyloxy)benzo[d]thiazole-6-carboxamide (190 mg, 0.635 mmol). The crude product was purified with flash column chromatography using dichloromethane/methanol (20:1) as eluent. Yield: 20 mg (6.6%); light grey solid.

¹H NMR (400 MHz, DMSO-$d_6$) δ 2.26 (s, 3H), 5.30 (s, 2H), 7.36-7.47 (m, 4H), 7.51-7.57 (m, 2H), 7.64 (d, J=1.3 Hz, 1H), 8.04 (s, 1H), 8.13 (s, 1H), 12.12 (s, 1H), 12.22 (s, 1H).

HRMS (ESI⁻) m/z for $C_{21}H_{15}Cl_2N_4O_3S$ ([M–H]⁻): calculated 473.0247, found 473.0255.

HPLC: $t_r$ 9.740 min (95.0% at 254 nm), method A.

(Example 29) Synthesis of N-(4-(benzyloxy)-6-(1H-tetrazol-5-yl)benzo[d]thiazol-2-yl)-3,4-dichloro-5-methyl-1H-pyrrole-2-carboxamide

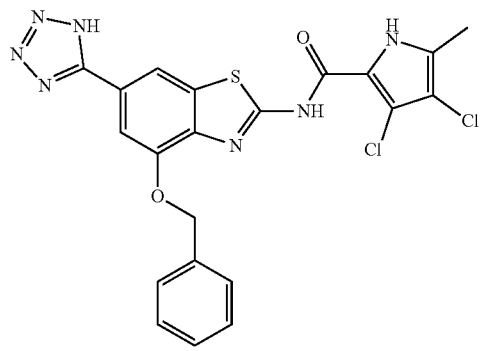 [SMILES: Cc1[nH]c(C(=O)Nc2nc3c(OCc4ccccc4)cc(-c4nnn[nH]4)cc3s2)c(Cl)c1Cl]

Exemplified Compound No. 29

Step 1: Synthesis of 3-(benzyloxy)-4-nitrobenzonitrile

To a solution of 3-(benzyloxy)-4-nitrobenzamide (700 mg, 2.57 mmol) in dry acetonitrile (10 mL) triphenylphosphine oxide (7.15 mg, 0.026 mmol), triethylamine (1.08 mL, 7.71 mmol) and oxalyl chloride (441 µL, 5.14 mmol) were added and the reaction mixture stirred at rt for 30 min. Triethylammonium chloride that was formed was filtered off and the mother liquid evaporated. The crude product was crystallized from methanol. Yield: 650 mg (99.4%); off-white solid.

¹H NMR (400 MHz, DMSO-$d_6$) δ 5.38 (s, 2H), 7.35-7.47 (m, 5H), 7.66 (dd, J=8.3, 1.6 Hz, 1H), 8.07-8.11 (m, 2H).

Step 2: Synthesis of 4-amino-3-(benzyloxy)benzonitrile

The same operation as in Example 9 (Step 2) was performed using 3-(benzyloxy)-4-nitrobenzonitrile (643 mg, 2.53 mmol). Yield: 321 mg (56.6%); white solid.

¹H NMR (400 MHz, DMSO-$d_6$) δ 5.16 (s, 2H), 5.82 (s, 2H), 6.69 (d, J=8.2 Hz), 7.12 (dd, J=8.2, 1.8 Hz, 1H), 7.22 (d, J=1.7 Hz, 1H), 7.31-7.36 (m, 1H), 7.37-7.43 (m, 2H), 7.47-7.53 (m, 2H).

Step 3: Synthesis of 2-amino-4-(benzyloxy)benzo[d]thiazole-6-carbonitrile

The same operation as in Example 5 (Step 3) was performed using 4-amino-3-(benzyloxy)benzonitrile (315 mg, 1.31 mmol). After neutralisation with 25% aqueous $NH_3$ solution the product was extracted with ethyl acetate (2×50 mL). The combined organic phases were washed with brine (20 mL), dried over $Na_2SO_4$, filtered and the solvent evaporated under reduced pressure. The crude product was suspended in methanol and filtered off. Yield: 126 mg (34.0%); yellow solid.

¹H NMR (400 MHz, DMSO-$d_6$) δ 5.22 (s, 2H), 7.32-7.38 (m, 2H), 7.38-7.44 (m, 2H), 7.45-7.50 (m, 2H), 7.84 (d, J=1.4 Hz, 1H), 8.02 (s, 2H).

Step 4: Synthesis of N-(4-(benzyloxy)-6-cyanobenzo[d]thiazol-2-yl)-3,4-dichloro-5-methyl-1H-pyrrole-2-carboxamide The same operation as in Example 1 (Step 1) was performed using 2-amino-4-(benzyloxy)benzo[d]thiazole-6-carbonitrile (120 mg, 0.427 mmol). Yield: 126 mg (64.6%); grey solid.

¹H NMR (400 MHz, DMSO-$d_6$) δ 2.26 (s, 3H), 5.32 (s, 2H), 7.37-7.49 (m, 3H), 7.53-7.54 (m, 2H), 7.57 (d, J=1.1 Hz, 1H), 8.21 (d, J=1.0 Hz, 1H), 12.25 (s, 1H), 12.29 (br s, 1H).

HRMS (ESI⁻) m/z for $C_{21}H_{13}Cl_2N_4O_2S$ ([M–H]⁻): calculated 455.0142, found 455.0147.

HPLC: $t_r$ 14.237 min (97.6% at 254 nm, 95.5% at 280 nm).

Step 5: Synthesis of N-(4-(benzyloxy)-6-(1H-tetrazol-5-yl)benzo[d]thiazol-2-yl)-3,4-dichloro-5-methyl-1H-pyrrole-2-carboxamide To a solution of N-(4-(benzyloxy)-6-cyanobenzo[d]thiazol-2-yl)-3,4-dichloro-5-methyl-1H-pyrrole-2-carboxamide (100 mg, 0.219 mmol) in N,N-dimethylformamide (5 mL) ammonium chloride (117 mg, 2.19 mmol) and sodium azide (142 mg, 2.19 mmol) were added and the reaction mixture was stirred at 125° C. overnight. Ethyl acetate (10 mL) and 1M HCl (5 mL) were added and the formed precipitate (the starting compound) was filtered off. The phases of the mother liquid were separated, organic phase was washed with brine (5 mL), dried over $Na_2SO_4$, filtered and the solvent removed under reduced pressure. The crude product was purified with flash column chromatography using dichloromethane/methanol/acetic acid (30:1:0.1) as eluent. Yield: 4 mg (3.7%); beige solid.

$^1$H NMR (400 MHz, DMSO-$d_6$) δ 2.26 (s, 3H), 5.36 (s, 2H), 7.37-7.48 (m, 3H), 7.57-7.59 (m, 2H), 7.78 (d, J=1.5 Hz, 1H), 8.29 (d, J=1.4 Hz, 1H), 12.18 (br s, 1H), 12.22 (s, 1H), signal for tetrazole NH is not seen.

HRMS (ESI$^-$) m/z for $C_{21}H_{14}Cl_2N_7O_2S$ ([M–H]$^-$): calculated 498.0312, found 498.0319.

(Example 30) Synthesis of 2-(3,4-dichloro-5-methyl-1H-pyrrole-2-carboxamido)-4-((3-fluorobenzyl)oxy)benzo[d]thiazole-6-carboxylic acid

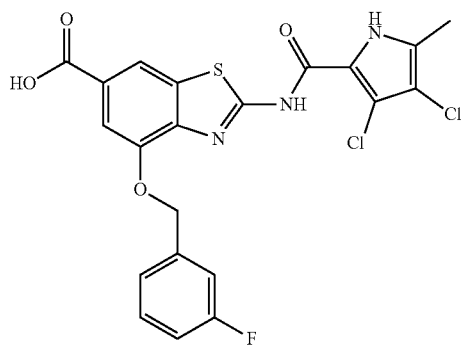 [SMILES: Cc1[nH]c(C(=O)Nc2nc3c(OCc4cccc(F)c4)cc(C(=O)O)cc3s2)c(Cl)c1Cl]

Exemplified Compound No. 30

Step 1: Synthesis of methyl 2-amino-4-((3-fluorobenzyl)oxy)benzo[d]thiazole-6-carboxylate The same operation as in Example 12 (Step 1) was performed using methyl 2-amino-4-hydroxybenzo[d]thiazole-6-carboxylate (190 mg, 0.847 mmol) and 1-(bromomethyl)-3-fluorobenzene (114 μL, 0.932 mmol). The crude product was recrystallized from diethyl ether instead of methanol.

Yield: 126 mg (44.7%); yellow crystals.

$^1$H NMR (400 MHz, DMSO-$d_6$) δ 3.61 (s, 3H), 5.05 (s, 2H), 6.93-6.99 (m, 1H), 7.09-7.14 (m, 1H), 7.21-7.27 (m, 2H), 7.72 (s, 2H), 7.77 (d, J=1.5 Hz, 1H).

Step 2: Synthesis of methyl 2-(3,4-dichloro-5-methyl-1H-pyrrole-2-carboxamido)-4-((3-fluorobenzyl)oxy)benzo[d]thiazole-6-carboxylate The same operation as in Example 1 (Step 1) was performed using methyl 2-amino-4-((3-fluorobenzyl)oxy)benzo[d]thiazole-6-carboxylate (110 mg, 0.331 mmol). Yield: 132 mg (71.7%); light grey solid.

$^1$H NMR (400 MHz, DMSO-$d_6$) δ 2.27 (s, 3H), 3.89 (s, 3H), 5.36 (s, 2H), 7.17-7.27 (m, 1H), 7.39-7.41 (m, 2H), 7.45-7.53 (m, 1H), 7.61 (s, 1H), 8.31 (s, 1H), 12.19 (s, 1H), 12.26 (s, 1H).

Step 3: Synthesis of 2-(3,4-dichloro-5-methyl-1H-pyrrole-2-carboxamido)-4-((3-fluorobenzyl)oxy)benzo[d]thiazole-6-carboxylic acid To a suspension of methyl 2-(3,4-dichloro-5-methyl-1H-pyrrole-2-carboxamido)-4-((3-fluorobenzyl)oxy)benzo[d]thiazole-6-carboxylate (58 mg, 0.114 mmol) in methanol (15 mL) 1M NaOH (570 μL, 0.57 mmol) was added and the reaction mixture stirred at 40° C. for 4 days. 2 equivalents of 1M NaOH (228 μL, 0.228 mmol) were added and the reaction mixture stirred at 40° C. overnight. The solvent was evaporated in vacuo, the residue acidified with 1M HCl to pH=1 and the formed precipitate was filtered off. The crude product was suspended in methanol, heated and filtered off. Yield: 36 mg (64.3%); brown crystals.

$^1$H NMR (400 MHz, DMSO-$d_6$) δ 2.27 (s, 3H), 5.35 (s, 2H), 7.18-7.26 (m, 1H), 7.38-7.40 (m, 2H), 7.46-7.53 (m, 1H), 7.61 (d, J=1.2 Hz, 1H), 8.27 (d, J=1.1 Hz, 1H), 12.25 (s, 1H), 12.16 (s, 1H), 13.01 (br s, 1H).

HRMS (ESI$^-$) m/z for $C_{21}H_{13}Cl_2FN_3O_4S$ ([M–H]$^-$): calculated 491.9993, found 491.9997.

HPLC: $t_r$ 11.797 min (99.0% at 254 nm, 97.2% at 280 nm), method A.

(Example 31) Synthesis of 2-(3,4-dichloro-5-methyl-1H-pyrrole-2-carboxamido)-4-(thiophen-3-ylmethoxy)benzo[d]thiazole-6-carboxylic acid

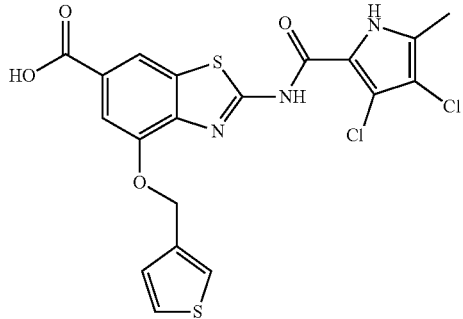 [SMILES: Cc1[nH]c(C(=O)Nc2nc3c(OCc4ccsc4)cc(C(=O)O)cc3s2)c(Cl)c1Cl]

Exemplified Compound No. 31

Step 1: Synthesis of methyl 4-nitro-3-(thiophen-3-ylmethoxy)benzoate

The same operation as in Example 9 (Step 1) was performed using 3-(bromomethyl)thiophene (539 mg, 3.04 mmol). Yield: 742 mg (99.7%); off-white solid.

$^1$H NMR (400 MHz, DMSO-$d_6$) δ 3.91 (s, 3H), 5.39 (s, 2H), 7.16-7.17 (m, 1H), 7.57-7.61 (m, 2H), 7.68 (dd, J=8.4, 1.6 Hz, 1H), 7.90 (d, J=1.6 Hz, 1H), 8.01 (d, J=8.3 Hz, 1H).

Step 2: Synthesis of methyl 4-amino-3-(thiophen-3-ylmethoxy)benzoate

The same operation as in Example 9 (Step 2) was performed using methyl 4-nitro-3-(thiophen-3-ylmethoxy)benzoate (400 mg, 1.364 mmol). Yield: 103 mg (28.7%); yellow oil.

¹H NMR (400 MHz, DMSO-d₆) δ 3.75 (s, 3H), 5.13 (s, 2H), 5.67 (s, 2H), 6.66 (d, J=8.7 Hz, 1H), 7.24 (dd, J=5.0, 1.2 Hz, 1H), 7.37-7.42 (m, 2H), 7.55-7.57 (m, 1H), 7.64-7.67 (m, 1H).

Step 3: Synthesis of methyl 2-amino-4-(thiophen-3-ylmethoxy)benzo[d]thiazole-6-carboxylate The same operation as in Example 5 (Step 3) was performed using methyl 4-amino-3-(thiophen-3-ylmethoxy)benzoate (280 mg, 1.06 mmol). Yield: 93 mg (27.3%); yellow solid.
¹H NMR (400 MHz, DMSO-d₆) δ 3.83 (s, 3H), 5.22 (s, 2H), 7.20 (dd, J=4.7, 1.6 Hz, 1H), 7.44 (d, J=1.6 Hz, 1H), 7.54-7.60 (m, 2H), 7.89 (s, 2H), 7.97 (d, J=1.6 Hz, 1H).

Step 4: Synthesis of methyl 2-(3,4-dichloro-5-methyl-1H-pyrrole-2-carboxamido)-4-(thiophen-3-ylmethoxy)benzo[d]thiazole-6-carboxylate The same operation as in Example 1 (Step 1) was performed using methyl 2-amino-4-(thiophen-3-ylmethoxy)benzo[d]thiazole-6-carboxylate (93 mg, 0.290 mmol). Yield: 63 mg (43.7%); light grey solid.
¹H NMR (400 MHz, DMSO-d₆) δ 2.26 (s, 3H), 3.89 (s, 3H), 5.32 (s, 2H), 7.26 (dd, J=4.9, 1.3 Hz, 1H), 7.58-7.64 (m, 2H), 7.64-7.70 (m, 1H), 8.30 (d, J=1.4 Hz, 1H), 12.20 (s, 1H), 12.22 (s, 1H).

Step 5: Synthesis of 2-(3,4-dichloro-5-methyl-1H-pyrrole-2-carboxamido)-4-(thiophen-3-ylmethoxy)benzo[d]thiazole-6-carboxylic acid To a suspension of methyl 2-(3,4-dichloro-5-methyl-1H-pyrrole-2-carboxamido)-4-(thiophen-3-ylmethoxy)benzo[d]thiazole-6-carboxylate (45 mg, 0.091 mmol) in methanol (15 mL) 1M NaOH (0.455 mL, 0.455 mmol) was added and the reaction mixture stirred at 40° C. overnight. Additional 0.455 mL of 1M NaOH were added and the reaction mixture stirred at 40° C. for 3 days. Solvent was evaporated in vacuo, the residue was acidified with 1M HCl to pH=1 and the formed precipitate was filtered off. The crude product was suspended in methanol, heated and filtered. Yield: 30 mg (68.3%); light grey solid.
¹H NMR (400 MHz, DMSO-d₆) δ 2.26 (s, 3H), 5.30 (s, 2H), 7.25 (dd, J=4.9, 1.3 Hz, 1H), 7.57-7.63 (m, 2H), 7.63-7.68 (m, 1H), 8.25 (d, J=1.4 Hz, 1H), 12.17 (s, 1H), 12.22 (s, 1H), 13.00 (s, 1H).
HRMS (ESI⁻) m/z for C₁H₁₄Cl₂N₃O₄S₂ ([M+H]⁺): calculated 481.9797, found 481.9794.
HPLC: t_r 4.527 min (95.1% at 254 nm), method B.

(Example 32) Synthesis of 2-(3,4-dichloro-5-methyl-1H-pyrrole-2-carboxamido)-4-(thiophen-2-ylmethoxy)benzo[d]thiazole-6-carboxylic acid

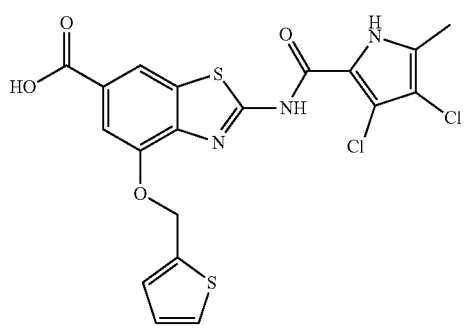 [SMILES: Cc1[nH]c(C(=O)Nc2nc3c(OCc4cccs4)cc(C(=O)O)cc3s2)c(Cl)c1Cl]

Exemplified Compound No. 32

Step 1: Synthesis of methyl 4-nitro-3-(thiophen-2-ylmethoxy)benzoate

To a solution of methyl 3-hydroxy-4-nitrobenzoate (1 g, 5.07 mmol) from Step 1 of the Example 6 in anhydrous THF (30 mL) triphenylphosphine (2.66 g, 10.1 mmol) and thiophen-2-ylmethanol (529 μL, 5.58 mmol) were added and the reaction mixture stirred for 10 min at rt. DIAD (2 mL, 10.1 mmol) was added dropwise on ice bath and the reaction mixture stirred at rt overnight. The solvent was evaporated in vacuo and the crude product purified with flash column chromatography using ethyl acetate/hexane (1:4) as eluent. Yield: 1.37 g (91.9%); yellow solid.
¹H NMR (400 MHz, DMSO-d₆) δ 3.92 (s, 3H), 5.60 (d, J=0.8 Hz, 2H), 7.06 (dd, J=5.1, 3.4 Hz, 1H), 7.24 (dd, J=3.5, 1.2 Hz, 1H), 7.60 (dd, J=5.1, 1.3 Hz, 1H), 7.69 (dd, J=8.3, 1.6 Hz, 1H), 7.96 (d, J=1.6 Hz, 1H), 8.00 (d, J=8.3 Hz, 1H).

Step 2: Synthesis of methyl 4-amino-3-(thiophen-2-ylmethoxy)benzoate

To a solution of methyl 4-nitro-3-(thiophen-2-ylmethoxy)benzoate (400 mg, 1.36 mmol) in acetic acid (30 mL), iron (381 mg, 6.82 mmol) was added and the reaction mixture stirred at 60° C. for 2 h. reaction mixture was cooled down, neutralised with saturated NaHCO₃ solution (300 mL) and extracted with ethyl acetate (100 mL). The organic phase was dried over Na₂SO₄, filtered and the solvent removed in vacuo. The crude product purified with flash column chromatography using ethyl acetate/hexane (1:2) as eluent. Yield: 250 mg (48.5%); yellow oil.
¹H NMR (400 MHz, DMSO-d₆) δ 3.75 (s, 3H), 5.32 (d, J=0.8 Hz, 2H), 5.59 (s, 2H), 6.67 (d, J=8.2 Hz, 1H), 7.05 (dd, J=5.1, 3.4 Hz, 1H), 7.23 (dd, J=3.4, 1.2 Hz, 1H), 7.40 (dd, J=8.2, 1.8 Hz, 1H), 7.44 (d, J=1.8 Hz, 1H), 7.56 (dd, J=5.1, 1.3 Hz, 1H).

Step 3: Synthesis of methyl 2-amino-4-(thiophen-2-ylmethoxy)benzo[d]thiazole-6-carboxylate The same operation as in Example 5 (Step 3) was performed using methyl 4-amino-3-(thiophen-2-ylmethoxy)benzoate (245 mg, 0.930 mmol). Yield: 145 mg (48.7%); yellow solid.
¹H NMR (400 MHz, DMSO-d₆) δ 3.83 (s, 3H), 5.44 (s, 2H), 7.04 (dd, J=5.1, 3.4 Hz, 1H), 7.20 (dd, J=3.4, 1.2 Hz, 1H), 7.46 (d, J=1.6 Hz, 1H), 7.56 (dd, J=5.1, 1.3 Hz, 1H), 7.92 (s, 2H), 7.98 (d, J=1.5 Hz, 1H).

Step 4: Synthesis of methyl 2-(3,4-dichloro-5-methyl-1H-pyrrole-2-carboxamido)-4-(thiophen-2-ylmethoxy)benzo[d]thiazole-6-carboxylate The same operation as in Example 1 (Step 1) was performed using methyl 2-amino-4-(thiophen-2-ylmethoxy)benzo[d]thiazole-6-carboxylate (120 mg, 0.375 mmol). Yield: 122 mg (65.6%); light grey solid.
¹H NMR (400 MHz, DMSO-d₆) δ 2.26 (s, 3H), 3.89 (s, 3H), 5.53 (s, 2H), 7.08 (dd, J=5.1, 3.4 Hz, 1H), 7.28 (dd, J=3.5, 1.2 Hz, 1H), 7.60 (dd, J=5.1, 1.3 Hz, 1H), 7.65 (d, J=1.5 Hz, 1H), 8.31 (d, J=1.4 Hz, 1H), 12.21-12.23 (m, 2H).

Step 5: Synthesis of 2-(3,4-dichloro-5-methyl-1H-pyrrole-2-carboxamido)-4-(thiophen-2-ylmethoxy)benzo[d]thiazole-6-carboxylic acid The same operation as in Example 31 (Step 5) was performed using methyl 2-(3,4-dichloro-5-methyl-1H-pyrrole-2-carboxamido)-4-(thiophen-2-ylmethoxy)benzo[d]thiazole-6-carboxylate (110 mg, 0.344 mmol). The crude product was purified with flash column chromatography using dichloromethane/methanol (9:1) as eluent. Yield: 50 mg (46.7%); beige solid.

$^1$H NMR (400 MHz, DMSO-d$_6$) δ 2.26 (s, 3H), 5.52 (s, 2H), 7.08 (dd, J=5.1, 3.4 Hz, 1H), 7.28 (dd, J=3.4, 1.2 Hz, 1H), 7.60 (dd, J=5.1, 1.2 Hz, 1H), 7.64 (d, J=1.5 Hz, 1H), 8.26 (d, J=1.4 Hz, 1H), 12.17 (s, 1H), 12.23 (s, 1H), 12.98 (s, 1H).

HRMS (ESI$^+$) m/z for $C_{19}H_{14}Cl_2N_3O_4S_2$ ([M+H]$^+$): calculated 481.9797, found 481.9792.

HPLC: t$_r$ 4.503 min (95.4% at 254 nm), method B.

(Example 33) Synthesis of methyl (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylate

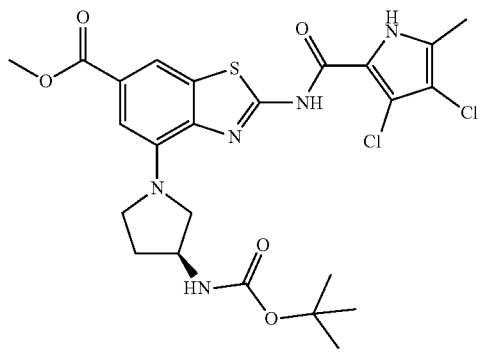 [SMILES: COC(=O)c1cc(N2CC[C@H](NC(=O)OC(C)(C)C)C2)c2nc(NC(=O)c3[nH]c(C)c(Cl)c3Cl)sc2c1]

Exemplified Compound No. 33

Step 1: Synthesis of methyl (S)-3-(3-((tert-butoxycarbonyl)amino)pyrrolidin-1-yl)-4-nitrobenzoate To a solution of methyl 3-fluoro-4-nitrobenzoate (1.00 g, 5.00 mmol) synthesized in Step 1 of the Example 5 in acetonitrile K$_2$CO$_3$ (1.38 g, 10.0 mmol) and (S)-3-(Boc-amino)pyrrolidine (1.12 g, 6.00 mmol) were added and the reaction mixture stirred at 60° C. for 4 h. Solvent was removed in vacuo, to the residue ethyl acetate and water were added and the phases were separated. Organic phase was washed with 1% citric acid and brine, dried over Na$_2$SO$_4$, filtered and the solvent removed in vacuo.

Yield: 1.83 mg (99.0%); yellow solid.

$^1$H NMR (400 MHz, DMSO-d$_6$) δ 1.38 (s, 9H), 1.91 (m, 1H), 2.11 (m, 1H), 2.89 (dd, J=10.4, 4.6 Hz, 1H), 3.31 (m, 2H), 3.41 (m, 1H), 3.89 (s, 3H), 4.09 (m, 1H), 7.24 (d, J=7.2 Hz, 1H), 7.27 (dd, J=8.5, 1.6 Hz, 1H), 7.51 (d, J=1.7 Hz, 1H), 7.83 (d, J=8.5 Hz, 1H).

Step 2: Synthesis of methyl (S)-4-amino-3-(3-((tert-butoxycarbonyl)amino)pyrrolidin-1-yl)benzoate The same operation as in Example 5 (Step 2) was performed using methyl (S)-3-(3-((tert-butoxycarbonyl)amino) pyrrolidin-1-yl)-4-nitrobenzoate (1.00 g, 2.74 mmol). Crude oily product was used in Step 3 without further purification.

Step 3: Synthesis of methyl (S)-2-amino-4-(3-((tert-butoxycarbonyl)amino)pyrrolidin-1-yl)benzo[d]thiazole-6-carboxylate The same operation as in Example 5 (Step 3) was performed using crude methyl (S)-4-amino-3-(3-((tert-butoxycarbonyl)amino)pyrrolidin-1-yl)benzoate (910 mg, 2.72 mmol). After neutralisation with 25% aqueous NH$_3$ solution the product was extracted with ethyl acetate (2×50 mL). The combined organic phases were washed with brine (20 mL), dried over Na$_2$SO$_4$, filtered and the solvent evaporated under reduced pressure. The crude product was purified with flash column chromatography using dichloromethane/methanol (40:1) as eluent. Yield: 216 mg (20.1%, over two steps); beige solid.

$^1$H NMR (400 MHz, DMSO-d$_6$) δ 1.39 (s, 9H), 1.83 (m, 1H), 2.11 (m, 1H), 3.31 (m, 1H), 3.47-3.64 (m, 2H), 3.80 (s, 3H), 3.85-3.93 (m, 1H), 4.01-4.14 (m, 1H), 6.94 (d, J=1.7 Hz, 1H), 7.16 (d, J=7.0 Hz, 1H), 7.57 (s, 2H), 7.66 (d, J=1.6 Hz, 1H).

Step 4: Synthesis of methyl (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylate The same operation as in Example 1 (Step 1) was performed using methyl (S)-2-amino-4-(3-((tert-butoxycarbonyl)amino)pyrrolidin-1-yl)benzo[d]thiazole-6-carboxylate (200 mg, 0.510 mmol) obtained in Step 3 above. Yield: 140 mg (48.3%); light green solid.

$^1$H NMR (400 MHz, DMSO-d$_6$) δ 1.40 (s, 9H), 1.87-1.95 (m, 1H), 2.12-2.20 (m, 1H), 2.28 (s, 3H), 3.49-3.53 (m, 1H), 3.65-3.71 (m, 1H), 3.74-3.80 (m, 1H), 3.85 (s, 3H), 3.98-4.02 (m, 1H), 4.11-4.22 (m, 1H), 7.03 (d, J=1.7 Hz, 1H), 7.23 (d, J=6.9 Hz, 1H), 7.90 (d, J=1.5 Hz, 1H), 11.71 (s, 1H), 12.36 (s, 1H).

HRMS (ESI$^+$) m/z for $C_{24}H_{28}Cl_2N_5O_5S$ ([M+H]$^+$): calculated 568.1183, found 568.1182.

(Example 34) Synthesis of (S)-1-(2-(3,4-dichloro-5-methyl-1H-pyrrole-2-carboxamido)-6-(methoxycarbonyl)benzo[d]thiazol-4-yl)pyrrolidin-3-aminium chloride

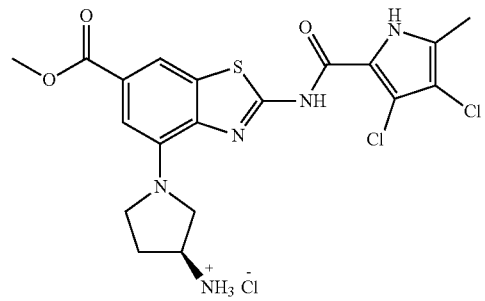 [SMILES: COC(=O)c1cc(N2CC[C@H](N)C2)c2nc(NC(=O)c3[nH]c(C)c(Cl)c3Cl)sc2c1 ; Cl]

Exemplified Compound No. 34

Step 1: Synthesis of (S)-1-(2-(3,4-dichloro-5-methyl-1H-pyrrole-2-carboxamido)-6-(methoxycarbonyl)benzo[d]thiazol-4-yl)pyrrolidin-3-aminium chloride The same operation as in Example 11 (Step 6) was performed using methyl (S)-4-(3-((tert-butoxycarbonyl)

amino)pyrrolidin-1-yl)-2-(3,4-dichloro-5-methyl-1H-pyrrole-2-carboxamido)benzo[d]thiazole-6-carboxylate (39 mg, 0.069 mmol) (Example 33). The crude product was purified with crystallization from methanol (10 mL). Yield: 15 mg (43.4%; beige solid.

¹H NMR (400 MHz, DMSO-$d_6$) δ 2.04-2.16 (m, 1H), 2.29 (s, 3H), 3.68-3.82 (m, 3H), 3.87 (s, 3H), 3.89-4.06 (m, 3H), 7.10 (d, J=1.6 Hz, 1H), 7.99 (d, J=1.5 Hz, 1H), 8.20 (s, 3H), 11.76 (s, 1H), 12.64 (s, 1H).

HRMS (ESI⁺) m/z for $C_{19}H_{20}Cl_2N_5O_3S$ ([M+H]⁺): calculated 468.0658, found 648.0656.

(Example 35) Synthesis of (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylic acid

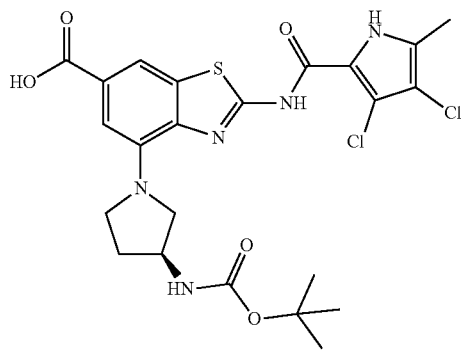 [SMILES: Cc1[nH]c(C(=O)Nc2nc3c(N4CC[C@H](NC(=O)OC(C)(C)C)C4)cc(C(=O)O)cc3s2)c(Cl)c1Cl]

Exemplified Compound No. 35

Step 1: Synthesis of (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylic acid The same operation as in Example 31 (Step 5) was performed using methyl (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylate (90 mg, 0.158 mmol) (Example 33). The crude product was purified with crystallization from ethyl acetate/methanol (5 mL/5 mL). (Yield: 71 mg (80.9%); brown solid.

¹H NMR (400 MHz, DMSO-$d_6$) δ 1.40 (s, 9H), 2.10-2.21 (m, 1H), 2.28 (s, 3H), 3.30 (m, 1H, signal is overlapping with the signal for water), 3.48-3.52 (m, 1H), 3.62-3.81 (m, 2H), 3.94-4.06 (m, 1H), 4.14-4.19 (m, 1H), 7.04 (d, J=1.4 Hz, 1H), 7.23 (d, J=7.0 Hz, 1H), 7.87 (d, J=1.5 Hz, 1H), 11.68 (s, 1H), 12.37 (s, 1H), 12.74 (br s, 1H).

HRMS (ESI⁺) m/z for $C_{23}H_{26}Cl_2N_5O_5S$ ([M+H]⁺): calculated 554.1026, found 554.1018.

(Example 36) Synthesis of (S)-1-(6-carboxy-2-(3,4-dichloro-5-methyl-1H-pyrrole-2-carboxamido)benzo[d]thiazol-4-yl)pyrrolidin-3-aminium chloride

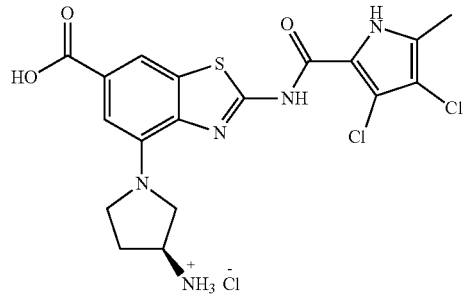 [SMILES: Cc1[nH]c(C(=O)Nc2nc3c(N4CC[C@H](N)C4)cc(C(=O)O)cc3s2)c(Cl)c1Cl ; Cl]

Exemplified Compound No. 36

Step 1: Synthesis of (S)-1-(6-carboxy-2-(3,4-dichloro-5-methyl-1H-pyrrole-2-carboxamido)benzo[d]thiazol-4-yl)pyrrolidin-3-aminium chloride The same operation as in Example 11 (Step 6) was performed using (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylic acid (39 mg, 0.070 mmol) (Example 35). The crude product was suspended in methanol and filtered off. Yield: 23 mg (66.6%); brown solid.

¹H NMR (400 MHz, DMSO-$d_6$) δ 2.05-2.16 (m, 1H), 2.29 (s, 3H), 3.66-3.80 (m, 3H), 3.86-4.05 (m, 3H), 7.11 (d, J=1.6 Hz, 1H), 7.96 (d, J=1.4 Hz, 1H), 8.20 (s, 3H), 11.73 (s, 1H), 12.65 (s, 1H), signal for COOH is not seen.

HRMS (ESI⁺) m/z for $C_{18}H_{18}Cl_2N_5O_3S$ ([M+H]⁺): calculated 454.0502, found 454.0498.

(Example 37) Synthesis of 2-(3,4-dichloro-5-methyl-1H-pyrrole-2-carboxamido)-4-(pyrrolidin-1-yl)benzo[d]thiazole-6-carboxylic acid

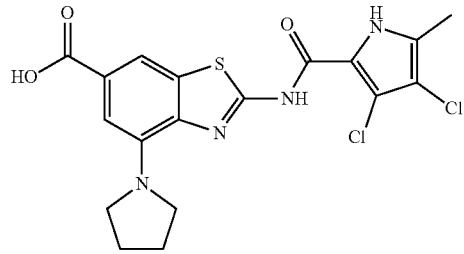 [SMILES: Cc1[nH]c(C(=O)Nc2nc3c(N4CCCC4)cc(C(=O)O)cc3s2)c(Cl)c1Cl]

Exemplified Compound No. 37

Step 1: Synthesis of methyl 4-nitro-3-(pyrrolidin-1-yl)benzoate

The same operation as in Example 33 (Step 1) was performed using methyl 3-fluoro-4-nitrobenzoate (1.00 g, 5.00 mmol), $K_2CO_3$ (1.38 g, 10.0 mmol) and pyrrolidine (493 μL, 6.00 mmol). Yield: 1.25 g (100%); orange crystals.

<sup>1</sup>H NMR (400 MHz, DMSO-d<sub>6</sub>) δ 1.89-1.96 (m, 4H), 3.16-3.19 (m, 4H), 3.88 (s, 3H), 7.24 (dd, J=8.5, 1.7 Hz, 1H), 7.53 (d, J=1.7 Hz, 1H), 7.83 (d, J=8.5 Hz, 1H).

Step 2: Synthesis of methyl 4-amino-3-(pyrrolidin-1-yl)benzoate

The same operation as in Example 5 (Step 2) was performed using methyl 4-nitro-3-(pyrrolidin-1-yl)benzoate (1.2 g, 4.80 mmol). Yield: 1.00 g (94.3%); yellow oil.

<sup>1</sup>H NMR (400 MHz, DMSO-d<sub>6</sub>) δ 1.76-1.94 (m, 4H), 2.88-3.03 (m, 4H), 3.73 (s, 3H), 5.53 (s, 2H), 6.66 (d, J=8.2 Hz, 1H), 7.38-7.45 (m, 2H).

Step 3: Synthesis of methyl 2-amino-4-(pyrrolidin-1-yl)benzo[d]thiazole-6-carboxylate The same operation as in Example 5 (Step 3) was performed using methyl 4-amino-3-(pyrrolidin-1-yl)benzoate (950 mg, 4.31 mmol). After neutralisation with 25% aqueous NH<sub>3</sub> solution the product was extracted with ethyl acetate (2×50 mL). The combined organic phases were washed with brine (20 mL), dried over Na<sub>2</sub>SO<sub>4</sub>, filtered and the solvent evaporated under reduced pressure. The crude product was purified with flash column chromatography using dichloromethane/methanol (40:1) as eluent. Yield: 65 mg (5.2%); white solid.

<sup>1</sup>H NMR (400 MHz, DMSO-de) δ 1.82-1.97 (m, 4H), 3.45-3.61 (m, 4H), 3.80 (s, 3H), 6.99 (d, J=1.7 Hz, 1H), 7.55 (s, 2H), 7.66 (d, J=1.7 Hz, 1H).

Step 4: Synthesis of methyl 2-(3,4-dichloro-5-methyl-1H-pyrrole-2-carboxamido)-4-(pyrrolidin-1-yl)benzo[d]thiazole-6-carboxylate The same operation as in Example 1 (Step 1) was performed using methyl 2-amino-4-(pyrrolidin-1-yl)benzo[d]thiazole-6-carboxylate (55 mg, 0.198 mmol) obtained in Step 3 above. Yield: 80 mg (89.0%); green solid.

<sup>1</sup>H NMR (400 MHz, DMSO-d<sub>6</sub>) δ 1.91-2.02 (m, 4H), 2.28 (s, 3H), 3.68-3.71 (m, 4H), 3.85 (s, 3H), 7.07 (d, J=1.7 Hz, 1H), 7.89 (d, J=1.6 Hz, 1H), 11.66 (s, 1H), 12.36 (s, 1H).

Step 5: Synthesis of 2-(3,4-dichloro-5-methyl-1H-pyrrole-2-carboxamido)-4-(pyrrolidin-1-yl)benzo[d]thiazole-6-carboxylic acid The same operation as in Example 31 (Step 5) was performed using methyl 2-(3,4-dichloro-5-methyl-1H-pyrrole-2-carboxamido)-4-(pyrrolidin-1-yl)benzo[d]thiazole-6-carboxylate (70 mg, 0.154 mmol).

The crude product was washed with methanol and additionally purified with filtration out of hot hexane. Yield: 22 mg (29.4%); yellow solid.

<sup>1</sup>H NMR (400 MHz, DMSO-d<sub>6</sub>) δ 1.91-2.01 (m, 4H), 2.28 (s, 3H), 3.67-3.71 (m, 4H), 7.08 (d, J=1.6 Hz, 1H), 7.85 (d, J=1.5 Hz, 1H), 11.62 (s, 1H), 12.36 (s, 1H), 12.74 (br s, 1H).

HRMS (ESI<sup>+</sup>) m/z for C<sub>18</sub>H<sub>17</sub>C<sub>2</sub>N<sub>4</sub>O<sub>3</sub>S ([M+H]<sup>+</sup>): calculated 439.0393, found 439.0389.

(Example 38) Synthesis of 2-(4,5-dibromo-1H-pyrrole-2-carboxamido)-4-((5-hydroxy-4-oxo-1,4-dihydropyridin-2-yl)methoxy)benzo[d]thiazole-6-carboxylic acid

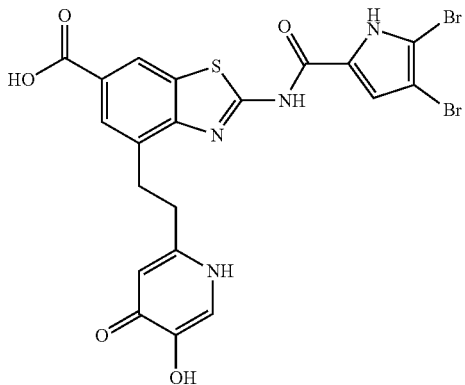 [SMILES: O=C(O)c1cc(CCc2cc(=O)c(O)c[nH]2)c2nc(NC(=O)c3cc(Br)c(Br)[nH]3)sc2c1]

Exemplified Compound No. 38

Step 1: Synthesis of methyl 2-amino-4-((5-((4-methoxybenzyl)oxy)-4-oxo-4H-pyran-2-yl)methoxy)benzo[d]thiazole-6-carboxylate To a solution of methyl 2-amino-4-hydroxybenzo[d]thiazole-6-carboxylate (1.02 g, 3.12 mmol) from Step 4 of the Example 6 in acetonitrile (40 mL), K<sub>2</sub>CO<sub>3</sub> (0.860 g, 6.22 mmol) and 2-(bromomethyl)-5-((4-methoxybenzyl)oxy)-4H-pyran-4-one (0.700 g, 3.12 mmol) was added. Reaction was stirred under reflux overnight. Solvent was removed under reduced pressure and the crude residue dissolved in ethyl acetate (140 mL). Organic phase was then successively washed with 10% citric acid (180 mL) and saturated saturated NaHCO<sub>3</sub> solution (180 mL). The precipitated product was filtered off. Solvent was removed under reduced pressure and crude product purified by column chromatography using dichloromethane/methanol (20:1) as eluent. Yield: 0.89 g (60.5%); brown solid.

<sup>1</sup>H NMR (400 MHz, DMSO-d<sub>6</sub>): δ 3.76 (s, 3H), 3.83 (s, 3H), 4.88 (s, 2H), 5.17 (s, 2H), 6.57 (s, 1H), 6.96 (d, 2H, J=8.7 Hz), 7.35 (d, 2H, J=8.7 Hz), 7.44 (d, 1H, J=1.5 Hz), 7.99 (s, 2H), 8.02 (d, 1H, J=1.5 Hz), 8.27 (s, 1H) ppm.

Step 2: Synthesis of methyl 2-(4,5-dibromo-1H-pyrrole-2-carboxamido)-4-((5-((4-methoxybenzyl)oxy)-4-oxo-4H-pyran-2-yl)methoxy)benzo[d]thiazole-6-carboxylate The same operation as in Example 2 (Step 1) was performed using methyl 2-amino-4-((5-((4-methoxybenzyl)oxy)-4-oxo-4H-pyran-2-yl)methoxy)benzo[d]thiazole-6-carboxylate (350 mg, 0.75 mmol) obtained in Step 1 above. Yield: 0.420 g (77.8%).

<sup>1</sup>H NMR (400 MHz, DMSO-d<sub>6</sub>): δ 3.78 (s, 3H), 3.89 (s, 3H), 4.90 (s, 2H), 5.26 (s, 2H), 6.64 (s, 1H), 6.97 (d, 2H, J=8.7 Hz), 7.36 (d, 2H, J=8.6 Hz), 7.57 (d, 1H, J=2.7 Hz), 7.60 (d, 1H), 8.31 (d, 1H), 8.35 (s, 1H), 13.00 (s, 1H), 13.28 (s, 1H) ppm.

Step 3: Synthesis of methyl 2-(4,5-dibromo-1H-pyrrole-2-carboxamido)-4-((5-((4-methoxybenzyl)oxy)-4-oxo-1,4-dihydropyridin-2-yl)methoxy)benzo[d]thiazole-6-carboxylate A suspension of methyl 2-(4,5-dibromo-1H-pyrrole-2-carboxamido)-4-((5-((4-methoxybenzyl)oxy)-4-oxo-4H-pyran-2-yl)methoxy)benzo[d]thiazole-6-carboxylate (0.150 g, 0.12 mmol) in methanol (15 mL) and 25% aqueous ammonia solution (11 mL) was stirred at 60° C. overnight. Solvent was then removed under reduced pressure and the crude product purified by flash column chromatography using dichloromethane/methanol (9:1) as eluent. Compound was obtained as a mixture of tautomers and $^1$H NMR signals could not be unambiguously assigned. Yield: 0.048 g (32.0%); beige solid.

Step 4: Synthesis of 2-(4,5-dibromo-1H-pyrrole-2-carboxamido)-4-((5-((4-methoxybenzyl)oxy)-4-oxo-1,4-dihydropyridin-2-yl)methoxy)benzo[d]thiazole-6-carboxylic acid The same operation as in Example 2 (Step 2) was performed using methyl 2-(4,5-dibromo-1H-pyrrole-2-carboxamido)-4-((5-((4-methoxybenzyl)oxy)-4-oxo-1,4-dihydropyridin-2-yl)methoxy)benzo[d]thiazole-6-carboxylate (0.040 g, 0.060 mmol) obtained in Step 3 above. Compound was obtained as a mixture of tautomers and $^1$H NMR signals could not be unambiguously assigned. Yield: 0.025 g (63.7%); beige solid.

Step 5: Synthesis of 2-(4,5-dibromo-1H-pyrrole-2-carboxamido)-4-((5-hydroxy-4-oxo-1,4-dihydropyridin-2-yl)methoxy)benzo[d]thiazole-6-carboxylic acid To a suspension of 2-(4,5-dibromo-1H-pyrrole-2-carboxamido)-4-((5-((4-methoxybenzyl)oxy)-4-oxo-1,4-dihydropyridin-2-yl)methoxy)benzo[d]thiazole-6-carboxylic acid (0.023 g, 0.033 mmol) in glacial acetic acid (5 mL) 1 M HCl in acetil acid (0.33 mmol) was added and the reaction mixture stirred at room temperature overnight. The precipitate was filtered off, washed with diethyl ether and dried in vacuo. Yield: 0.010 g (52.4%), pink solid.

$^1$H NMR (400 MHz, DMSO-d$_6$): δ 5.38 (s, 2H), 7.13 (s, 1H), 7.55 (s, 1H), 7.59 (d, 1H, J=1.3 Hz), 8.02 (s, 1H), 8.32 (d, 1H, J=1.3 Hz), 12.94 (s, 1H), 13.29 (s, 1H) ppm.

HRMS (ESI$^-$) m/z for C$_{19}$H$_{11}$Br$_2$N$_4$O$_6$S ([M–H]$^-$): calculated 580.8773, found 580.8772.

(Example 39) Synthesis of (5-hydroxy-4-oxo-4H-pyran-2-yl)methyl 2-(4,5-dibromo-1H-pyrrole-2-carboxamido)benzo[d]thiazole-6-carboxylate Exemplified Compound No. 39

Step 1: Synthesis of 2-amino-N-((5-((4-methoxybenzyl)oxy)-4-oxo-4H-pyran-2-yl)methyl)benzo[d]thiazole-6-carboxamide To a solution of 2-aminobenzo[d]thiazole-6-carboxylic acid (0.063 g, 0.33 mmol) and 2-(aminomethyl)-5-((4-methoxybenzyl)oxy)-4H-pyran-4-one (0.487 g, 1.86 mmol) in N,N-dimethylformamide (10 mL) EDC (0.535 g, 2.23 mmol), HOBt (0.327 g, 2.42 mmol) and NMM (0.409 mL, 3.72 mmol) were added and the reaction mixture stirred at room temperature overnight. Reaction mixture was cooled on an ice bath and the precipitate filtered off and dried. Yield: 0.509 g (72.4%); grey solid.

$^1$H NMR (400 MHz, DMSO-d$_6$): δ 3.76 (s, 3H), 4.34 (d, J=5.7 Hz, 2H), 4.85 (s, 2H), 6.26 (s, 1H), 6.95 (d, J=6.8 Hz, 2H), 7.31-7.42 (m, 3H), 8.19 (s, 1H), 7.78 (dd, J$_1$=8.4 Hz, J$_2$=1.9 Hz, 1H), 7.82 (s, 2H), 8.22 (d, J=1.8 Hz, 1H), 8.98 (t, J=5.8 Hz, 1H) ppm.

Step 2: Synthesis of 2-(4,5-dibromo-1H-pyrrole-2-carboxamido)-N-((5-((4-methoxybenzyl)oxy)-4-oxo-4H-pyran-2-yl)methyl)benzo[d]thiazole-6-carboxamide The same operation as in Example 2 (Step 1) was performed using 2-amino-N-((5-((4-methoxybenzyl)oxy)-4-oxo-4H-pyran-2-yl)methyl)benzo[d]thiazole-6-carboxamide (0.100 g, 0.23 mmol) obtained in Step 1. Yield: 0.114 g (72.6%); grey solid.

$^1$H NMR (400 MHz, DMSO-d$_6$): δ 3.77 (s, 3H), 4.39 (d, J=5.6 Hz, 2H), 4.86 (s, 2H), 6.31 (s, 1H), 6.95 (d, J=8.7 Hz, 2H), 7.35 (d, J=8.7 Hz, 2H), 7.55 (s, 1H), 7.84 (d, J=8.4 Hz, 1H), 7.99 (dd, J$_1$=8.5 Hz, J$_2$=1.8 Hz, 1H), 8.20 (s, 1H), 8.55 (d, 1H, J=1.8 Hz), 9.15 (t, 1H, J=5.7 Hz), 12.82 (s, 1H), 13.28 (s, 1H) ppm.

Step 3: Synthesis of 2-(4,5-dibromo-1H-pyrrole-2-carboxamido)-N-((5-hydroxy-4-oxo-4H-pyran-2-yl)methyl)benzo[d]thiazole-6-carboxamide The same operation as in Example 38 (Step 5) was performed using 2-(4,5-dibromo-1H-pyrrole-2-carboxamido)-N-((5-((4-methoxybenzyl)oxy)-4-oxo-4H-pyran-2-yl)methyl)benzo[d]thiazole-6-carboxamide (0.079 g, 0.12 mmol) obtained in Step 2. Yield: 0.058 g (88.9%); grey solid.

$^1$H NMR (400 MHz, DMSO-d$_6$): δ 4.39 (d, J=5.6 Hz, 2H), 6.33 (s, 1H), 7.55 (d, J=2.7 Hz, 1H), 7.83 (d, J=8.5 Hz, 1H), 7.99 (dd, J$_1$=8.5 Hz, J$_2$=1.6 Hz, 1H), 8.08 (s, 1H), 8.57 (d, J=1.7 Hz, 1H), 9.17 (t, J=5.7 Hz, 1H), 12.82 (s, 1H), 13.29 (d, J=2.7 Hz, 1H) ppm.

HRMS (ESI$^+$) m/z for C$_{19}$H$_{13}$Br$_2$N$_4$O$_5$S ([M+H]$^+$): calculated 566.8968, found 566.8809.

(Example 40) Synthesis of (5-hydroxy-4-oxo-1,4-dihydropyridin-2-yl)methyl 2-(4,5-dibromo-1H-pyrrole-2-carboxamido)benzo[d]thiazole-6-carboxylate

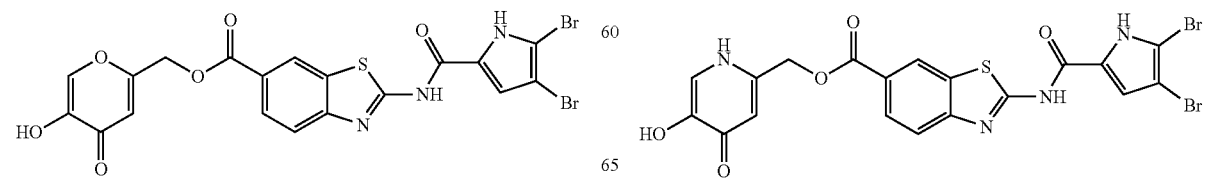

Exemplified Compound No. 40

Step 1: Synthesis of 2-(4,5-dibromo-1H-pyrrole-2-carboxamido)-N-((5-((4-methoxybenzyl)oxy)-4-oxo-1,4-dihydropyridin-2-yl)methyl)benzo[d]thiazole-6-carboxamide The same operation as in Example 38 (Step 3) was performed using 2-(4,5-dibromo-1H-pyrrole-2-carboxamido)-N-((5-((4-methoxybenzyl)oxy)-4-oxo-4H-pyran-2-yl)methyl)benzo[d]thiazole-6-carboxamide (0.100 g, 0.15 mmol) from Step 2 of Example 39. Yield: 0.088 g (87.9%); grey solid.

$^1$H NMR (400 MHz, DMSO-$d_6$): δ 3.76 (s, 3H), 4.43 (s, 2H), 4.94 (s, 2H), 6.11 (s, 1H), 6.94 (d, J=8.7 Hz, 2H), 7.29-7.45 (m, 3H), 7.54 (s, 1H), 7.84 (d, J=8.5 Hz, 1H), 8.00 (dd, J$_1$=8.6 Hz, J$_2$=1.8 Hz, 1H), 8.56 (d, 1H, J=1.8 Hz), 9.09 (t, 1H, J=5.8 Hz), 11.22 (s, 1H), 12.82 (s, 1H), 13.28 (s, 1H) ppm.

Step 2: 2-(4,5-dibromo-1H-pyrrole-2-carboxamido)-N-((5-hydroxy-4-oxo-1,4-dihydropyridin-2-yl)methyl)benzo[d]thiazole-6-carboxamide The same operation as in Example 38 (Step 5) was performed using 2-(4,5-dibromo-1H-pyrrole-2-carboxamido)-N-((5-((4-methoxybenzyl)oxy)-4-oxo-1,4-dihydropyridin-2-yl)methyl)benzo[d]thiazole-6-carboxamide (0.070 g, 0.10 mmol) obtained in Step 1. Yield: 0.049 g (84.8%); purple solid.

$^1$H NMR (400 MHz, DMSO-$d_6$): δ 4.65 (d, J=5.5 Hz, 2H), 7.24 (s, 1H), 7.55 (d, J=2.6 Hz, 1H), 7.86 (d, J=8.5 Hz, 1H), 8.03 (dd, J$_1$=8.5 Hz, J$_2$=1.7 Hz, 1H), 8.10 (s, 1H), 8.60 (d, J=1.8 Hz, 1H), 9.43 (t, J=5.7 Hz, 1H), 10.99 (s, 1H), 12.83 (s, 1H), 14.41 (d, J=2.7 Hz, 1H) ppm.

HRMS (ESI$^-$) m/z for $C_{19}H_{13}Br_2N_4O_5S$ ([M−H]$^-$): calculated 565.9128, found 565.8969.

(Example 41) Synthesis of 2-(3,4-dichloro-N-isopropyl-5-methyl-1H-pyrrole-2-carboxamido)benzo[d]thiazole-6-carboxylic acid

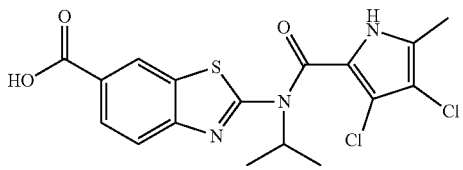 [SMILES: Cc1[nH]c(C(=O)N(c2nc3ccc(C(=O)O)cc3s2)C(C)C)c(Cl)c1Cl]

Exemplified Compound No. 41

Step 1: Synthesis of ethyl 2-bromobenzo[d]thiazole-6-carboxylate

To the solution of ethyl 2-aminobenzo[d]thiazole-6-carboxylate (8.0 g, 36.0 mmol) and CuBr$_2$ (16.07 g, 72.0 mmol) in acetonitrile (200 mL), tert-butyl nitrite (7.42 mL, 72.0 mmol) was added on ice bath. The reaction mixture was stirred at room temperature for 14 h. The solvent was removed under reduced pressure and to the residue ethyl acetate (200 mL) and NH$_4$Cl solution (200 mL) were added. The organic phase was washed with brine (100 mL) and NH$_4$Cl solution (100 mL), dried over Na$_2$SO$_4$, filtered and the solvent evaporated under reduced pressure. Yield: 8.0 g (78%); pale brown solid.

$^1$H NMR (400 MHz, DMSO-$d_6$): δ 1.36 (t, J=7.1 Hz, 3H), 4.37 (q, J=7.1 Hz, 2H), 8.10 (s, 2H), 8.82 (s, 1H) ppm.

Step 2: Synthesis of ethyl 2-(isopropylamino)benzo[d]thiazole-6-carboxylate

A solution of ethyl 2-bromobenzo[d]thiazole-6-carboxylate (1.00 g, 3.49 mmol) and isopropylamine (2.86 mL, 34.9 mmol) in THF (70 mL) was stirred at room temperature for 14 h. The solvent was removed under reduced pressure. Crude product was dissolved in ethyl acetate (100 mL) and washed successively with 1% citric acid (2×50 mL), saturated NaHCO$_3$ solution (50 mL) and brine (50 mL). Organic phase was dried over Na$_2$SO$_4$, filtered and the solvent removed under reduced pressure. Yield: 0.915 g (99.1%), yellow oil.

$^1$H NMR (400 MHz, DMSO-$d_6$): δ 1.22 (d, J=6.5 Hz, 6H), 1.32 (t, J=7.1 Hz, 3H), 3.96-4.11 (m, 1H), 4.28 (q, J=7.1 Hz, 2H), 7.41 (d, J=8.4 Hz, 1H), 7.81 (dd, J$_1$=8.4 Hz, J$_2$=1.8 Hz, 1H), 8.28 (d, J=1.6 Hz, 1H), 8.35 (d, J=7.3 Hz, 1H) ppm.

Step 3: Synthesis of 2-(isopropylamino)benzo[d]thiazole-6-carboxylic acid

To a solution of ethyl 2-(isopropylamino)benzo[d]thiazole-6-carboxylate (0.940 g, 3.56 mmol) in 1,4-dioxane (30 mL), 2 M NaOH (8.89 mL, 17.8 mmol) was added and the mixture was allowed to stir at room temperature for 14 h. The solvent was removed under reduced pressure and 1 M HCl was added until reaching pH=3. The precipitate was filtered off and dried. Yield: 0.749 g (89.1%); grey solid.

$^1$H NMR (400 MHz, DMSO-$d_6$): δ 1.22 (d, J=6.6 Hz, 6H), 4.02 (q, J=6.6 Hz, 1H), 7.39 (d, J=8.1 Hz, 1H), 7.79 (d, J=8.3 Hz, 1H), 8.13-8.45 (m, 2H), 12.62 (s, 1H) ppm.

Step 4: Synthesis of 4-methoxybenzyl 2-(isopropylamino)benzo[d]thiazole-6-carboxylate To a solution of 2-(isopropylamino)benzo[d]thiazole-6-carboxylic acid (0.568 g, 2.40 mmol) in dry DMF (10 mL), potassium carbonate (0.498 g, 3.61 mmol) and 4-methoxybenzyl chloride (0.451 mL, 2.88 mmol) were added and the mixture was allowed to stir at room temperature for 14 h. The solvent was removed under reduced pressure and to the residue ethyl acetate (30 mL) and water (30 mL) were added. The organic phase was dried over Na$_2$SO$_4$, filtered and solvent evaporated under reduced pressure. The crude product was recrystallized from ethyl acetate. Yield: 0.806 g (94.1%), white solid.

$^1$H NMR (400 MHz, DMSO-$d_6$) δ 1.22 (d, J=6.5 Hz, 6H), 3.76 (s, 3H), 4.02 (q, J=6.7 Hz, 1H), 5.25 (s, 2H), 6.92-7.02 (m, 2H), 7.31-7.50 (m, 3H), 7.82 (dd, J$_1$=8.4 Hz, J$_2$=1.8 Hz, 1H), 8.29 (d, J=1.8 Hz, 1H), 8.36 (d, J=7.3 Hz, 1H) ppm.

Step 5: Synthesis of 4-methoxybenzyl 2-(3,4-dichloro-N-isopropyl-5-methyl-1H-pyrrole-2-carboxamido)benzo[d]thiazole-6-carboxylate The same operation as in Example 1 (Step 1) was performed using 4-methoxybenzyl 2-(isopropylamino)benzo[d]thiazole-6-carboxylate (0.150 g, 0.42 mmol) obtained in Step 4. Crude product was purified by preparative TLC using dichloromethane/methanol (20:1) as eluent. Yield: 0.031 g (13.8%); white solid.

$^1$H NMR (400 MHz, CDCl$_3$) δ 1.56 (s, 6H), 2.30 (s, 3H), 3.82 (s, 3H), 5.03 (p, J=6.8 Hz, 1H), 5.31 (s, 2H), 6.90-6.95 (m, 2H), 7.37-7.43 (m, 2H), 7.81 (d, J=8.5 Hz, 1H), 8.10 (dd, J$_1$=8.6 Hz, J$_2$=1.7 Hz, 1H), 8.40 (d, J=1.6 Hz, 1H), 9.09 (s, 1H) ppm.

Step 6: Synthesis of 2-(3,4-dichloro-N-isopropyl-5-methyl-1H-pyrrole-2-carboxamido) benzo[d]thiazole-6-carboxylic acid The same operation as in Example 38 (Step 5) was performed using 4-methoxybenzyl 2-(3,4-dichloro-N-isopropyl-5-methyl-1H-pyrrole-2-carboxamido)benzo[d]thiazole-6-carboxylate (0.029 g, 0.055 mmol). Yield: 0.018 g (80.2%); white solid.

$^1$H NMR (400 MHz, DMSO-d$_6$) δ 1.51 (d, J=6.2 Hz, 6H), 2.23 (s, 3H), 4.96 (s, 1H), 7.83 (d, J=8.2 Hz, 1H), 7.97 (d, J=7.0 Hz, 1H), 8.53 (s, 1H), 12.53 (s, 1H) ppm.

HRMS (ESI$^+$) m/z for C$_{17}$H$_{16}$Cl$_2$N$_3$O$_3$S ([M+H]$^+$): calculated 412.0284, found 412.0279.

HPLC: t$_r$ 3.873 min (98.0% at 254 nm), method B.

(Example 42) Synthesis of 2-(3,4-dichloro-N-cyclopropyl-5-methyl-1H-pyrrole-2-carboxamido)benzo[d]thiazole-6-carboxylic acid

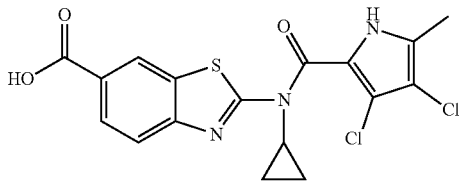 [SMILES: Cc1[nH]c(C(=O)N(c2nc3ccc(C(=O)O)cc3s2)C2CC2)c(Cl)c1Cl]

Exemplified Compound No. 42

Step 1: Synthesis of 4-methoxybenzyl 2-aminobenzo[d]thiazole-6-carboxylate

The same operation as in Example 41 (Step 4) was performed using 2-amino-benzo[d]thiazole-6-carboxylic acid (1.50 g, 7.7 mmol). Yield: 0.219 g (9.0%); white solid.

$^1$H NMR (400 MHz, DMSO-d$_6$) δ 3.76 (s, 3H), 5.26 (s, 2H), 6.93-6.99 (m, 2H), 7.40-7.48 (m, 3H), 7.88 (dd, J$_1$=8.5 Hz, J$_2$=1.8 Hz, 1H), 8.37 (d, J=1.8 Hz, 1H), 8.53 (s, 2H) ppm.

Step 2: Synthesis of 4-methoxybenzyl 2-bromobenzo[d]thiazole-6-carboxylate

The same operation as in Example 41 (Step 1) was performed using 4-methoxybenzyl 2-aminobenzo[d]thiazole-6-carboxylate (0.300 g, 0.95 mmol). The reaction mixture was stirred at room temperature only for 2 h. Yield: 0.354 g (98.1%); light brown solid.

$^1$H NMR (400 MHz, DMSO-d$_6$) δ 3.77 (s, 3H), 5.32 (s, 2H), 6.91-7.03 (m, 2H), 7.34-7.50 (m, 2H), 8.09 (d, J=1.2 Hz, 2H), 8.82 (d, J=1.3 Hz, 1H) ppm.

Step 3: Synthesis of 4-methoxybenzyl 2-(cyclopropylamino)benzo[d]thiazole-6-carboxylate The same operation as in Example 41 (Step 2) was performed using 4-methoxybenzyl 2-bromobenzo[d]thiazole-6-carboxylate (0.279 g, 0.74 mmol). Yield: 0.211 g (80.7%); white solid.

$^1$H NMR (400 MHz, DMSO-d$_6$) δ 0.55-0.64 (m, 2H), 0.79 (td, J$_1$=6.9 Hz, J$_2$=4.7 Hz, 2H), 2.73 (s, 1H), 3.76 (s, 3H), 5.26 (s, 2H), 6.93-7.00 (m, 2H), 7.39-7.51 (m, 3H), 7.82-7.88 (m, 1H), 8.38 (d, J=1.8 Hz, 1H), 8.77 (s, 1H) ppm.

Step 4: Synthesis of 4-methoxybenzyl 2-(3,4-dichloro-N-cyclopropyl-5-methyl-1H-pyrrole-2-carboxamido)benzo[d]thiazole-6-carboxylate The same operation as in Example 1 (Step 1) was performed using 4-methoxybenzyl 2-(cyclopropylamino)benzo[d]thiazole-6-carboxylate (0.201 g, 0.57 mmol). Yield: 0.092 g (30.6%); white solid.

$^1$H NMR (400 MHz, DMSO-d$_6$) δ 0.59-0.66 (m, 2H), 1.04 (q, J=6.9 Hz, 2H), 2.26 (s, 3H), 3.68 (tt, J$_1$=7.3 Hz, J$_2$=3.9 Hz, 1H), 3.77 (s, 3H), 5.31 (s, 2H), 6.95-7.01 (m, 2H), 7.43-7.47 (m, 2H), 7.87-7.93 (m, 1H), 8.02 (dt, J$_1$=8.6 Hz, J$_2$=2.1 Hz, 1H), 8.66-8.69 (m, 1H), 12.31 (s, 1H) ppm.

Step 5: Synthesis of 2-(3,4-dichloro-N-cyclopropyl-5-methyl-1H-pyrrole-2-carboxamido)benzo[d]thiazole-6-carboxylic acid The same operation as in Example 38 (Step 5) was performed using 4-methoxybenzyl 2-(3,4-dichloro-N-cyclopropyl-5-methyl-1H-pyrrole-2-carboxamido)benzo[d]thiazole-6-carboxylate (0.050 g, 0.094 mmol). Yield: 0.010 g (25.9%); white solid.

$^1$H NMR (400 MHz, DMSO-d$_6$) δ 0.63 (s, 2H), 1.04 (d, J=6.9 Hz, 2H), 2.27 (s, 3H), 7.89 (d, J=8.5 Hz, 1H), 8.00 (dd, J$_1$=8.6 Hz, J$_2$=1.8 Hz, 1H), 8.62 (d, J=1.8 Hz, 1H), 12.32 (s, 1H).

HRMS (ESI$^+$) m/z for C$_{17}$H$_{14}$Cl$_2$N$_3$O$_3$S ([M+H]$^+$): calculated 410.0127, found 410.0124.

(Example 43) Synthesis of 2-(3,4-dichloro-N-ethyl-5-methyl-1H-pyrrole-2-carboxamido)benzo[d]thiazole-6-carboxylic acid

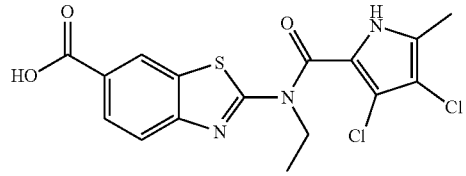 [SMILES: CCN(C(=O)c1[nH]c(C)c(Cl)c1Cl)c1nc2ccc(C(=O)O)cc2s1]

Exemplified Compound No. 43

Step 1: Synthesis of 4-methoxybenzyl 2-(ethylamino)benzo[d]thiazole-6-carboxylate The same operation as in Example 41 (Step 2) was performed using 4-methoxybenzyl 2-bromobenzo[d]thiazole-6-carboxylate (0.230 g, 0.61 mmol) obtained in Step 2 of the Example 42. Yield: 0.203 g (97.5%); white solid.

$^1$H NMR (400 MHz, DMSO-d$_6$) δ 1.21 (t, J=7.0 Hz, 3H), 3.41 (q, J=7.0 Hz, 2H), 3.76 (s, 3H), 5.25 (s, 2H), 6.92-7.01 (m, 2H), 7.42 (dt, J$_1$=8.5 Hz, J$_2$=2.3 Hz, 3H), 7.82 (dd, J$_1$=8.5 Hz, J$_2$=1.8 Hz, 1H), 8.30 (d, J=1.8 Hz, 1H), 8.42 (t, J=5.3 Hz, 1H) ppm.

Step 2: Synthesis of 4-methoxybenzyl 2-(3,4-dichloro-N-ethyl-5-methyl-1H-pyrrole-2-carboxamido)benzo[d]thiazole-6-carboxylate The same operation as in Example 1 (Step 1) was performed using 4-methoxybenzyl 2-(ethylamino)benzo[d]thiazole-6-carboxylate (0.180 g, 0.53 mmol). Yield: 0.078 g (28.6%); white solid.

$^1$H NMR (400 MHz, DMSO-$d_6$) δ 1.22 (t, J=7.0 Hz, 3H), 2.25 (s, 3H), 3.76 (s, 3H), 4.40 (q, J=7.0 Hz, 2H), 5.30 (s, 2H), 6.97-7.02 (m, 2H), 7.45 (d, J=8.7 Hz, 2H), 7.88-7.95 (m, 1H), 8.03 (dd, $J_1$=8.5 Hz, $J_2$=1.8 Hz, 1H), 8.68 (dd, $J_1$=1.7 Hz, $J_2$=0.4 Hz, 1H), 12.50 (s, 1H) ppm.

Step 3: Synthesis of 2-(3,4-dichloro-N-ethyl-5-methyl-1H-pyrrole-2-carboxamido)benzo[d]thiazole-6-carboxylic acid The same operation as in Example 38 (Step 5) was performed using 4-methoxybenzyl 2-(3,4-dichloro-N-ethyl-5-methyl-1H-pyrrole-2-carboxamido)benzo[d]thiazole-6-carboxylate (0.063 g, 0.12 mmol).

Yield: 0.013 g (26.9%); white solid.

$^1$H NMR (400 MHz, DMSO-$d_6$) δ 1.23 (t, J=6.9 Hz, 3H), 2.26 (s, 3H), 4.41 (q, J=6.9 Hz, 2H), 7.90 (d, J=8.5 Hz, 1H), 8.02 (dd, J=8.5, 1.6 Hz, 1H), 8.63 (d, J=1.5 Hz, 1H), 12.52 (s, 1H) ppm.

HRMS (ESI$^+$) m/z for $C_{16}H_{14}Cl_2N_3O_3S$ ([M+H]$^+$): calculated 398.0127, found 398.0125.

HPLC: $t_r$ 3.813 min (97.4% at 254 nm), method B.

(Example 44) Synthesis of 2-(3,4-dichloro-5-methyl-1H-pyrrole-2-carboxamido)-4-phenylbenzo[d]thiazole-6-carboxylic acid

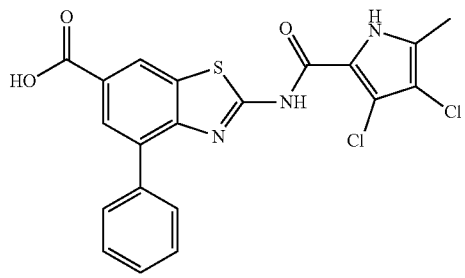 [SMILES: Cc1[nH]c(C(=O)Nc2nc3c(-c4ccccc4)cc(C(=O)O)cc3s2)c(Cl)c1Cl]

Exemplified Compound No. 44

Step 1: Synthesis of methyl 4-aminobenzoate

The same operation as in Example 5 (Step 1) was performed using 4-aminobenzoic acid (12.0 g, 87.5 mmol). Yield: 8.04 g (60.8%); pink crystals.

$^1$H NMR (400 MHz, DMSO-$d_6$) δ 3.74 (s, 3H), 3.92 (s, 2H), 6.57 (d, J=8.7 Hz, 2H), 7.64 (d, J=8.8 Hz, 2H).

Step 2: Synthesis of methyl 4-amino-3-bromobenzoate

To a solution of methyl 4-aminobenzoate (1.33 g, 8.79 mmol) in DMF (10 mL) N-bromosuccinimide (1.56 g, 8.79 mmol) was added and the reaction mixture stirred at room temperature overnight. The reaction mixture was poured in water (20 mL) and the product extracted with ethyl acetate (3×20 mL). Combined organic phases were washed with brine (20 mL), dried over $Na_2SO_4$, filtered and the solvent evaporated in vacuo. The crude product was purified with flash column chromatography using ethyl acetate/hexane (1:4) as eluent. Yield: 1.35 g (44.4%); white solid.

$^1$H NMR (400 MHz, DMSO-$d_6$) δ 3.76 (s, 3H), 6.21 (s, 2H), 6.80 (d, J=8.5 Hz, 1H), 7.65 (dd, J=8.5, 2.0 Hz, 1H), 7.89 (d, J=2.0 Hz, 1H).

Step 3: Synthesis of methyl 6-amino-[1,1'-biphenyl]-3-carboxylate

Methyl 4-amino-3-bromobenzoate (1.0 g, 4.35 mmol), phenylboronic acid (636 mg, 5.22 mmol) and $K_2CO_3$ (1.8 g, 13.0 mmol) were suspended in a mixture of toluene/ethanol/water (5:2:1, 60 mL) and flushed with argon for 5 minutes. Bis(triphenylphosphine)palladium(II) dichloride (153 mg, 0.217 mmol) was added and the reaction mixture stirred at 80° C. overnight. After cooling the reaction mixture was quenched with $NH_4Cl$ (10 mL) and the product extracted with ethyl acetate (3×15 mL). Combined organic phases were washed with brine (20 mL), dried over $Na_2SO_4$, filtered and the solvent evaporated in vacuo. The crude product was purified with flash column chromatography using ethyl acetate/hexane (1:4) as eluent. Yield: 0.98 mg (99.2%); transparent oil.

$^1$H NMR (400 MHz, DMSO-$d_6$) δ 3.75 (s, 3H), 5.68 (s, 2H), 6.79 (d, J=8.5 Hz, 1H), 7.35-7.43 (m, 3H), 7.45-7.51 (m, 2H), 7.57 (d, J=2.1 Hz, 1H), 7.66 (dd, J=8.5, 2.1 Hz, 1H).

Step 4: Synthesis of methyl 2-amino-4-phenylbenzo[d]thiazole-6-carboxylate

The same operation as in Example 5 (Step 3) was performed using methyl 6-amino-[1,1'-biphenyl]-3-carboxylate (800 mg, 3.52 mmol). The crude product was recrystallized from methanol. Yield: 714 mg (71.4%); yellow crystals.

$^1$H NMR (400 MHz, DMSO-$d_6$) δ 3.85 (s, 3H), 7.33-7.40 (m, 1H), 7.41-7.49 (m, 2H), 7.75 (dd, J=8.3, 1.3 Hz, 2H), 7.86 (d, J=1.8 Hz, 1H), 8.00 (s, 2H), 8.30 (d, J=1.8 Hz, 1H).

Step 5: Synthesis of methyl 2-(3,4-dichloro-5-methyl-1H-pyrrole-2-carboxamido)-4-phenylbenzo[d]thiazole-6-carboxylate The same operation as in Example 1 (Step 1) was performed using methyl 2-amino-4-phenylbenzo[d]thiazole-6-carboxylate (250 mg, 0.879 mmol) obtained in Step 4 above. Yield: 70 mg (17.3%); grey solid.

$^1$H NMR (400 MHz, DMSO-$d_6$) δ 2.26 (s, 3H), 3.91 (s, 3H), 7.41-7.47 (m, 1H), 7.49-7.56 (m, 2H), 7.77-7.83 (m, 2H), 8.02 (d, J=1.7 Hz, 1H), 8.68 (d, J=1.7 Hz, 1H), 12.01 (s, 1H), 12.33 (s, 1H).

Step 6: Synthesis of 2-(3,4-dichloro-5-methyl-1H-pyrrole-2-carboxamido)-4-phenylbenzo[d]thiazole-6-carboxylic acid The same operation as in Example 31 (Step 5) was performed using methyl 2-(3,4-dichloro-5-methyl-1H-pyrrole-2-carboxamido)-4-phenylbenzo[d]thiazole-6-carboxylate (50 mg, 0.109 mmol). After adding the additional 534 µL of 1M NaOH the second day, the reaction mixture was stirred for 2 more days at 50° C. The crude product was washed with methanol without heating. Yield: 35 mg (72.2%); beige solid.

$^1$H NMR (400 MHz, DMSO-$d_6$) δ 2.27 (s, 3H), 7.40-7.47 (m, 1H), 7.48-7.56 (m, 2H), 7.77-7.83 (m, 2H), 8.02 (d, J=1.7 Hz, 1H), 8.63 (d, J=1.7 Hz, 1H), 11.98 (s, 1H), 12.33 (s, 1H), 13.03 (s, 1H).

HRMS (ESI$^+$) m/z for $C_{20}H_{14}Cl_2N_3O_3S$ ([M+H]$^+$): calculated 446.0127, found 446.0118.

HPLC: $t_r$ 12.470 min (96.5% at 254 nm), method A.

(Example 45) Synthesis of 2-(4-bromo-3-chloro-5-methyl-1H-pyrrole-2-carboxamido) benzo[d]thiazole-6-carboxylic acid

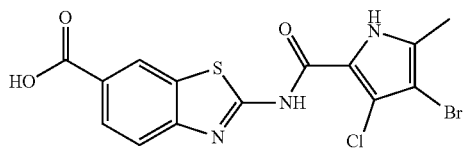 [SMILES: Cc1[nH]c(C(=O)Nc2nc3ccc(C(=O)O)cc3s2)c(Cl)c1Br]

Exemplified Compound No. 45

Step 1: Synthesis of ethyl 2-(4-bromo-3-chloro-5-methyl-1H-pyrrole-2-carboxamido)benzo[d]thiazole-6-carboxylate The same operation as in Example 1 (Step 1) was performed using ethyl 2-aminobenzo[d]thiazole-6-carboxylate (0.094 mg, 0.42 mmol). Yield: 0.121 mg (64.5%).

$^1$H NMR (400 MHz, DMSO-$d_6$) δ 1.35 (t, J=7.1 Hz, 3H), 2.28 (s, 3H), 4.35 (q, J=7.1 Hz, 2H), 7.83 (s, 1H), 8.03 (dd, J=8.5, 1.8 Hz, 1H), 8.66 (s, 1H), 11.95 (s, 1H), 12.43 (s, 1H) ppm.

Step 2: Synthesis of 2-(4-bromo-3-chloro-5-methyl-1H-pyrrole-2-carboxamido)benzo[d]thiazole-6-carboxylic acid The same operation as in Example 1 (Step 2) was performed using ethyl 2-(4-bromo-3-chloro-5-methyl-1H-pyrrole-2-carboxamido)benzo[d]thiazole-6-carboxylate (0.100 mg, 0.23 mmol). Yield: 0.080 mg (85.4%).

$^1$H NMR (400 MHz, DMSO-$d_6$) δ 2.28 (d, J=11.0 Hz, 3H), 7.74 (d, J=8.2 Hz, 1H), 7.99 (d, J=8.6 Hz, 1H), 8.56 (s, 1H), 12.53 (s, 2H) ppm.

HRMS (ESI$^+$) m/z for $C_{14}H_{10}BrClN_3O_3S$ ([M+H]$^+$): calculated 413.9309, found 413.9321.

The invention claimed is:

1. A compound of formula (I):

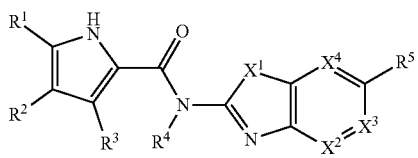

I wherein:
$R^1$, $R^2$, and $R^3$ are each independently selected from H, halogen, —CN, —CF$_3$, amino, methylamino, ethylamino, optionally substituted $C_{1-6}$ alkyl, optionally substituted $C_{1-6}$ alkoxy, and optionally substituted $C_{3-6}$ cycloalkyl; wherein two of $R^1$, $R^2$, and $R^3$ are halogen;

$R^4$ is (CH$_2$)$_{0-6}$-A wherein A is H, carboxyl, NR$^6$R$^7$ or is selected from optionally substituted monocyclic $C_{3-7}$ cycloalkyl, optionally substituted monocyclic $C_{3-7}$ cycloalkenyl, optionally substituted saturated or unsaturated monocyclic 3-7 membered heterocycle, optionally substituted saturated or unsaturated fused bicyclic 8-10 membered-heterocycle, optionally substituted $C_{6-10}$ aryl and optionally substituted 5-10 membered heteroaryl;

$R^5$ is (hydroxyimino)methyl, —CO—$C_{1-6}$ alkyl, —CO—$C_{2-6}$ alkenyl, —CO—$C_{2-6}$ alkynyl, carboxyl, —COO—$C_{1-6}$ alkyl, —CONR$^6$R$^7$, —OCONR$^6$R$^7$, —OCO—$C_{1-6}$ alkyl, —COO—$C_{1-6}$ alkyl-COO—$C_{1-6}$ alkyl, —CONHCH(CO$_2$R$^7$)R$^6$, —(CH$_2$)$_{0-6}$OH, —O—$C_{1-6}$ alkyl, hydroxyl-$C_{1-6}$ alkyl, heterocyclyl, aryl, —C(=NOR$^7$) $C_{1-6}$ alkyl, —C(=NOR$^7$)NR$^6$R$^7$, —S(O)$_p$NR$^6$R$^7$, —S(O)p-$C_{1-6}$ alkyl-CONHR$^7$, —C(O)NHS(O)p-$C_{1-6}$ alkyl, —C(O)NHS(O)p-aryl, —CH$_2$CH(COOR$^6$)OH, —$C_{1-6}$ alkyl-CH(NR$^6$R$^7$) COOR$^6$ or —$C_{1-6}$ alkyl-CH(NR$^6$R$^7$)CONR$^6$R$^7$), wherein any alkyl, alkenyl, alkynyl, heterocyclyl or aryl may be optionally substituted;

$R^6$ and $R^7$ are independently at each occurrence selected from H and optionally substituted $C_{1-6}$ alkyl;

or $R^6$ and $R^7$ may together with the nitrogen to which they are attached form a 5 or 6-membered heterocyclic ring, optionally substituted with 1 or 2 substituents independently selected from $C_{1-6}$ alkyl, $C_{2-6}$ alkenyl, $C_{2-6}$ alkynyl, hydroxyl, $C_{1-6}$ alkoxy, halogen, cyano, nitro, carboxyl, hydroxy-$C_{1-6}$ alkyl-, $C_{1-6}$ alkoxy-$C_{1-6}$ alkyl, halogen-$C_{1-6}$ alkyl-, difluoromethyl, trifluoromethyl, formyl, —CO—$C_{1-6}$ alkyl, —COO—$C_{1-6}$ alkyl, —C(O)NH$_2$, —C(O)NH—$C_{1-6}$ alkyl, —C(O)N [$C_{1-6}$ alkyl]$_2$, —SO$_2$NH$_2$, —SO$_2$NH—$C_{1-6}$ alkyl, —SO$_2$N [$C_{1-6}$ alkyl]$_2$ and —S(O) p-$C_{1-6}$ alkyl;

p is (independently at each occurrence) 0, 1 or 2;

$X^1$ is S, O or NH;

$X^2$, $X^3$ and $X^4$ are each independently selected from N or C—R$^8$;

$R^8$ is H, hydroxy, halogen, carboxyl, $C_{1-6}$ alkyl, $C_{2-6}$ alkenyl, $C_{2-6}$ alkynyl, (CH$_2$)$_m$O—$C_{1-6}$ alkyl, (CH$_2$)$_m$S—$C_{1-6}$ alkyl, (CH$_2$)$_m$S(=O)—$C_{1-6}$ alkyl, (CH$_2$)$_m$O (CH$_2$)$_m$—$C_{3-7}$ cycloalkyl, (CH$_2$)$_m$—$C_{3-7}$ cycloalkyl, (CH$_2$)$_m$O(CH$_2$)$_m$aryl, (CH$_2$)$_m$O(CH$_2$)$_m$-5-10-membered heterocycle, (CH$_2$)$_m$-5-10-membered heterocycle, halogen-$C_{1-6}$ alkyl, cyano or (CH$_2$)$_m$NR$^9$R$^{10}$, wherein each m is an integer independently selected from 0, 1, 2 and 3, and wherein any alkyl, alkenyl, alkynyl, cycloalkyl, heterocycle or aryl may be optionally substituted;

$R^9$ and $R^{10}$ are each independently selected from H or $C_{1-6}$ alkyl, $C_{3-6}$ cycloalkyl and 4-6-membered heterocyclyl, wherein any alkyl, cycloalkyl or heterocyclyl may be optionally substituted, or $R^9$ and $R^{10}$ join together to form an optionally substituted 4-6-membered heterocyclyl and where each m is an integer independently selected from 0, 1, 2 and 3;

or a pharmaceutically acceptable salt, racemate, diastereomer, enantiomer, ester, carbamate, sulphate, or phosphate thereof.

2. The compound of claim 1, wherein $R^1$ is methyl.

3. The compound of claim 1, wherein $R^2$ and $R^3$ are chloro.

4. The compound of claim 1, wherein $R^4$ is H or —$(CH_2)_{1-6}$-A.

5. The compound of claim 1, wherein $X^2$ is C—$R^8$, and $X^3$ and $X^4$ are CH.

6. The compound of claim 1, wherein $X^2$, $X^3$ and $X^4$ are CH.

7. The compound of claim 1, wherein $X^1$ is sulphur.

8. The compound of claim 1, wherein $R^5$ is carboxyl.

9. The compound of claim 1, wherein:
$R^1$ is methyl;
$R^2$ and $R^3$ are each independently selected from chloro, bromo or fluoro;
$R^4$ is hydrogen or —$(CH_2)_{1-6}$-A, wherein A is optionally substituted $C_{6-10}$ aryl or optionally substituted heterocyclyl;
$R^5$ is carboxyl;
$X^1$ is S;
$X^2$, $X^3$ and $X^4$ are CH.

10. The compound of claim 1, wherein:
$R^1$ is methyl;
$R^2$ and $R^3$ are each independently selected from chloro, bromo or fluoro;
$R^4$ is hydrogen;
$R^5$ is carboxyl;
$X^1$ is S or NH;
$X^2$ is C—$R^8$, wherein $R^8$ is selected from —O—$(CH_2)_{0-3}$—$CH_3$, fluoro, hydroxyl, optionally substituted —O—$(CH_2)_{0-3}$ aryl or optionally substituted —O—$(CH_2)_{0-3}$ heterocyclyl;
$X^3$ and $X^4$ are CH.

11. The compound of claim 1, wherein $R^1$ is optionally substituted $C_{1-6}$ alkyl.

12. The compound of claim 1, wherein $R^2$ and $R^3$ are halogen.

13. The compound of claim 1, wherein $R^1$ is optionally substituted $C_{1-6}$ alkyl, and $R^2$ and $R^3$ are halogen.

14. The compound of claim 1, wherein $R^1$ is methyl, and $R^2$ and $R^3$ are chloro.

15. The compound of claim 1, wherein
$R^1$ is methyl;
$R^2$ and $R^3$ are chloro;
$R^4$ is hydrogen;
$R^5$ is carboxyl or —COO—$C_{1-6}$ alkyl, wherein the alkyl may be optionally substituted;
$X^1$ is S;
$X^2$ is C—$R^8$, wherein $R^8$ is $(CH_2)_mO(CH_2)_m$-5-10-membered heterocycle or $(CH_2)_m$-5-10-membered heterocycle, wherein each m is an integer independently selected from 0, 1, 2 and 3, and wherein any heterocycle may be optionally substituted;
$X^3$ and $X^4$ are CH.

16. A compound selected from the group consisting of:
2-(3,4-dichloro-5-methyl-1H-pyrrole-2-carboxamido)benzo[d]thiazole-6-carboxylic acid,
2-(4,5-dibromo-1H-pyrrole-2-carboxamido)benzo[d]thiazole-6-carboxylic acid,
2-(4,5-dichloro-1H-pyrrole-2-carboxamido)benzo[d]thiazole-6-carboxylic acid,
2-(3,4-dichloro-5-methyl-1H-pyrrole-2-carboxamido)benzo[d]thiazole-5-carboxylic acid,
2-(3,4-dichloro-5-methyl-1H-pyrrole-2-carboxamido)-4-fluorobenzo[d]thiazole-6-carboxylic acid,
2-(4,5-dibromo-1H-pyrrole-2-carboxamido)-4-hydroxybenzo[d]thiazole-6-carboxylic acid,
2-(3,4-dichloro-5-methyl-1H-pyrrole-2-carboxamido)-4-hydroxybenzo[d]thiazole-6-carboxylic acid,
2-(3,4-dichloro-5-methyl-1H-pyrrole-2-carboxamido)-4-methoxybenzo[d]thiazole-6-carboxylic acid,
4-(benzyloxy)-2-(3,4-dichloro-5-methyl-1H-pyrrole-2-carboxamido)benzo[d]thiazole-6-carboxylic acid,
4-(2-((6-carboxy-2-(3,4-dichloro-5-methyl-1H-pyrrole-2-carboxamido)benzo[d]thiazol-4-yl)oxy)ethyl)morpholin-4-ium chloride,
2-((6-carboxy-2-(3,4-dichloro-5-methyl-1H-pyrrole-2-carboxamido)benzo[d]thiazol-4-yl)oxy)ethan-1-aminium chloride,
4-((4-carboxybenzyl)oxy)-2-(3,4-dichloro-5-methyl-1H-pyrrole-2-carboxamido)benzo[d]thiazole-6-carboxylic acid,
2-(3,4-dichloro-5-methyl-1H-pyrrole-2-carboxamido)-5-hydroxybenzo[d]thiazole-6-carboxylic acid,
7-chloro-2-(3,4-dichloro-5-methyl-1H-pyrrole-2-carboxamido)benzo[d]thiazole-6-carboxylic acid,
2-(N-benzyl-4,5-dibromo-1H-pyrrole-2-carboxamido)benzo[d]thiazole-6-carboxylic acid,
2-(N-benzyl-3,4-dichloro-5-methyl-1H-pyrrole-2-carboxamido)benzo[d]thiazole-6-carboxylic acid,
N-(6-(1H-tetrazol-5-yl)benzo[d]thiazol-2-yl)-3,4-dichloro-5-methyl-1H-pyrrole-2-carboxamide,
2-(3,4-dichloro-5-methyl-1H-pyrrole-2-carboxamido)benzo[d]thiazole-6-carboxamide,
2-(4,5-dibromo-1H-pyrrole-2-carboxamido)-N-hydroxybenzo[d]thiazole-6-carboxamide,
2-(3,4-dichloro-5-methyl-1H-pyrrole-2-carboxamido)-N-hydroxybenzo[d]thiazole-6-carboxamide,
3-(2-(4,5-dibromo-1H-pyrrole-2-carboxamido)benzo[d]thiazole-6-carboxamido)propanoic acid,
3-(2-(3,4-dichloro-5-methyl-1H-pyrrole-2-carboxamido)benzo[d]thiazole-6-carboxamido)propanoic acid,
(2-(3,4-dichloro-5-methyl-1H-pyrrole-2-carboxamido)benzo[d]thiazole-6-carbonyl)glycine,
4-((3-carboxybenzyl)oxy)-2-(3,4-dichloro-5-methyl-1H-pyrrole-2-carboxamido)benzo[d]thiazole-6-carboxylic acid,
4-(2-((6-((cyanomethyl)carbamoyl)-2-(3,4-dichloro-5-methyl-1H-pyrrole-2-carboxamido)benzo[d]thiazol-4-yl)oxy)ethyl)morpholin-4-ium chloride,
N-(cyanomethyl)-2-(3,4-dichloro-5-methyl-1H-pyrrole-2-carboxamido)benzo[d]thiazole-6-carboxamide,
4-(benzyloxy)-N-(cyanomethyl)-2-(3,4-dichloro-5-methyl-1H-pyrrole-2-carboxamido)benzo[d]thiazole-6-carboxamide,
4-(benzyloxy)-2-(3,4-dichloro-5-methyl-1H-pyrrole-2-carboxamido)benzo[d]thiazole-6-carboxamide,
N-(4-(benzyloxy)-6-(1H-tetrazol-5-yl)benzo[d]thiazol-2-yl)-3,4-dichloro-5-methyl-1H-pyrrole-2-carboxamide,
2-(3,4-dichloro-5-methyl-1H-pyrrole-2-carboxamido)-4-((3-fluorobenzyl)oxy)benzo[d]thiazole-6-carboxylic acid,
2-(3,4-dichloro-5-methyl-1H-pyrrole-2-carboxamido)-4-(thiophen-3-ylmethoxy)benzo[d]thiazole-6-carboxylic acid,
2-(3,4-dichloro-5-methyl-1H-pyrrole-2-carboxamido)-4-(thiophen-2-ylmethoxy)benzo[d]thiazole-6-carboxylic acid,
methyl(S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylate,
(S)-1-(2-(3,4-dichloro-5-methyl-1H-pyrrole-2-carboxamido)-6-(methoxycarbonyl)benzo[d]thiazol-4-yl)pyrrolidin-3-aminium chloride, (S)-4-(3-((tert-butoxycarbonyl)amino)pyrrolidin-1-yl)-2-(3,4-dichloro-5-methyl-1H-pyrrole-2-carboxamido)benzo[d]thiazole-6-carboxylic acid, (S)-1-(6-carboxy-2-(3,4-dichloro-5-methyl-1H-pyrrole-2-carboxamido)benzo[d]thiazol-4-yl)pyrrolidin-3-aminium chloride, 2-(3,4-dichloro-5-methyl-1H-pyrrole-2-carboxamido)-4-(pyrrolidin-1-yl)benzo[d]thiazole-6-carboxylic acid, 2-(4,5-dibromo-1H-pyrrole-2-carboxamido)-4-((5-hydroxy-4-oxo-1,4-dihydropyridin-2-yl)methoxy)benzo[d]thiazole-6-carboxylic acid, (5-hydroxy-4-oxo-4H-pyran-2-yl)methyl 2-(4,5-dibromo-1H-pyrrole-2-carboxamido)benzo[d]thiazole-6-carboxylate, (5-hydroxy-4-oxo-1,4-dihydropyridin-2-yl)methyl 2-(4,5-dibromo-1H-pyrrole-2-carboxamido)benzo[d]thiazole-6-carboxylate, 2-(3,4-dichloro-N-isopropyl-5-methyl-1H-pyrrole-2-carboxamido)benzo[d]thiazole-6-carboxylic acid, 2-(3,4-dichloro-N-cyclopropyl-5-methyl-1H-pyrrole-2-carboxamido)benzo[d]thiazole-6-carboxylic acid, 2-(3,4-dichloro-N-ethyl-5-methyl-1H-pyrrole-2-carboxamido)benzo[d]thiazole-6-carboxylic acid, 2-(3,4-dichloro-5-methyl-1H-pyrrole-2-carboxamido)-4-phenylbenzo[d]thiazole-6-carboxylic acid and 2-(4-bromo-3-chloro-5-methyl-1H-pyrrole-2-carboxamido)benzo[d]thiazole-6-carboxylic acid.

17. A pharmaceutical composition comprising a compound of claim 1 and a pharmaceutically acceptable excipient or carrier.

18. A pharmaceutical composition comprising a compound of claim 16 and a pharmaceutically acceptable excipient or carrier.

19. A method for treatment of a bacterial infection in a warm-blooded animal, comprising administering a therapeutically effective amount of a compound of claim 1 to the warm-blooded animal.

20. The method according to claim 19, wherein the warm-blooded animal is a human.

21. A method for treatment of a bacterial infection in a warm-blooded animal, comprising administering a therapeutically effective amount of a compound of claim 16 to the warm-blooded animal.

22. The method according to claim 21, wherein the warm-blooded animal is a human.

* * * * *